US010948497B2

(12) United States Patent
Kellum et al.

(10) Patent No.: US 10,948,497 B2
(45) Date of Patent: Mar. 16, 2021

(54) PROTEOMIC BIOMARKERS OF SEPSIS IN ELDERLY PATIENTS

(71) Applicant: University of Pittsburgh—of the Commonwealth System of Higher Education, Pittsburgh, PA (US)

(72) Inventors: John A. Kellum, Pittsburgh, PA (US); Zhiyun Cao, Chicago, IL (US); Derek Angus, Pittsburgh, PA (US); Sachin Purushottam Yende, Pittsburgh, PA (US); Rena Angilena Sowell Robinson, Pittsburgh, PA (US)

(73) Assignee: The University of Pittsburgh—the Commonwealth of Higher Education, Pittsburgh, PA (US)

( * ) Notice: Subject to any disclaimer, the term of this patent is extended or adjusted under 35 U.S.C. 154(b) by 142 days.

(21) Appl. No.: 16/154,344

(22) Filed: Oct. 8, 2018

(65) Prior Publication Data
US 2019/0265251 A1    Aug. 29, 2019

Related U.S. Application Data

(63) Continuation of application No. 14/392,122, filed as application No. PCT/US2014/043909 on Jun. 24, 2014, now Pat. No. 10,126,305.
(Continued)

(51) Int. Cl.
*G01N 35/00* (2006.01)
*G01N 33/48* (2006.01)
(Continued)

(52) U.S. Cl.
CPC ..... *G01N 33/6848* (2013.01); *G01N 2800/26* (2013.01)

(58) Field of Classification Search
CPC .......... G01N 33/6848; G01N 2800/26; G01N 35/00; G01N 33/48; G01N 15/06; G01N 33/00
See application file for complete search history.

(56) References Cited

U.S. PATENT DOCUMENTS 5,198,212 A * 3/1993 Polk, Jr. ............... A61K 38/217
424/85.5
5,705,188 A   1/1998 Junichi et al. ................ 424/450
(Continued)

FOREIGN PATENT DOCUMENTS

WO    WO 97/30731    8/1997

OTHER PUBLICATIONS

Abraham, et al., "Double-Blind Randomised Controlled Trial of Monoclonal Antibody to Human Tumour Necrosis Factor in Treatment of Septic Shock. NORASEPT II Study Group." *Lancet*, 351(9107):929-933 (1998).
(Continued)

*Primary Examiner* — Brian J. Sines
(74) *Attorney, Agent, or Firm* — Medlen & Carroll, LLP

(57) ABSTRACT

A proteomic expression platform to identify age-related sepsis risk is disclosed using patients with an intra-abdominal infection. A semi-quantitative plasma proteomics workflow was applied which incorporated tandem immuno affinity depletion, iTRAQ labeling, strong cation exchange fractionation, and nanoflow-liquid chromatography coupled to high resolution mass spectrometry. A protein profile was determined that exhibit statistically significant differences in expression levels amongst patients with severe sepsis as a function of age. Representative pathways that are differentially-expressed include, but are not limited to, acute phase
(Continued)

response, coagulation signaling, atherosclerosis signaling, lipid metabolism, and production of nitric oxide/reactive oxygen species.

25 Claims, 45 Drawing Sheets

Specification includes a Sequence Listing.

Related U.S. Application Data

(60) Provisional application No. 61/839,214, filed on Jun. 25, 2013.

(51) Int. Cl.
  *G01N 15/06* (2006.01)
  *G01N 33/00* (2006.01)
  *G01N 33/68* (2006.01)

(56) References Cited

U.S. PATENT DOCUMENTS

| | | | | |
|---|---|---|---|---|
| 5,993,811 | A | * | 11/1999 | Becker ............... A61P 37/00 424/130.1 |
| 6,251,598 | B1 | * | 6/2001 | di Giovine ........... C12Q 1/6883 435/6.18 |
| 6,660,267 | B1 | * | 12/2003 | Carroll ................ C07K 7/58 424/181.1 |
| 8,772,239 | B2 | * | 7/2014 | Tsuruta ................ A61P 7/00 514/14.7 |
| 10,126,305 | B2 | * | 11/2018 | Kellum .............. G01N 33/6848 |
| 2004/0197930 | A1 | | 10/2004 | Rosenfeld et al. ........... 436/510 |
| 2005/0148029 | A1 | | 7/2005 | Buechler et al. .............. 435/7.1 |
| 2007/0161125 | A1 | | 7/2007 | Rosenfeld et al. ........... 436/518 |
| 2009/0159793 | A1 | | 6/2009 | Hanas et al. ................... 250/282 |
| 2010/0190652 | A1 | | 7/2010 | Nagalla et al. .................. 506/7 |
| 2012/0077690 | A1 | * | 3/2012 | Singbartl ........... G01N 33/6893 506/9 |
| 2013/0323751 | A1 | * | 12/2013 | Singbartl ........... G01N 33/6893 435/7.4 |
| 2014/0162370 | A1 | | 6/2014 | Ling et al. ...................... 436/86 |
| 2017/0074868 | A1 | * | 3/2017 | Anderberg ......... G01N 33/5308 |

OTHER PUBLICATIONS

Abraham, et al., "Efficacy and Safety of Monoclonal Antibody to Human Tumor Necrosis Factor Alpha in Patients with Sepsis Syndrome. A Randomized, Controlled, Double-Blind, Multicenter Clinical Trial. TNF-Alpha MAb Sepsis Study Group." *JAMA*, 273(12):934-941 (1995).

Abraham, et al., "Efficacy and Safety of Tifacogin (Recombinant Tissue Factor Pathway Inhibitor) in Severe Sepsis: A Randomized Controlled Trial." *JAMA*, 290(2):238-247 (2003).

An, et al., "Sepsis: From Pattern to Mechanism and Back." *Critical Reviews in Biomedical Engineering*, 40(4):341-351 (2012).

Angus, et al., "E5 Murine Monoclonal Antiendotoxin Antibody in Gram-Negative Sepsis: A Randomized Controlled Trial. E5 Study Investigators." *JAMA*, 283(13):1723-1730 (2000).

Angus, et al., "Epidemiology of Severe Sepsis in the United States: Analysis of Incidence, Outcome, and Associated Costs of Care." *Crit Care Med*, 29(7):1303-1310 (2001).

Annane, et al., "Effect of Treatment with Low Doses of Hydrocortisone and Fludrocortisone on Mortality in Patients with Septic Shock." *Jama*, 288(7):862-871 (2002).

Annane, et al., "Corticosteroids for Severe Sepsis and Septic Shock: A Systematic Review and Meta-Analysis." *BMJ*, 329(7464):480 (2004).

Annane, et al., "Corticosteroids in the Treatment of Severe Sepsis and Septic Shock in Adults: A Systematic Review." *JAMA*, 301(22):2362-2375 (2009).

Balk, "Severe Sepsis and Septic Shock. Definitions, Epidemiology, and Clinical Manifestations." *Crit Care Clin*, 16(2):179-192 (2000).

Batzofin, et al., "The Use of Steroids in the Treatment of Severe Sepsis and Septic Shock." *Best Practice & Research Clinical Endocrinology & Metabolism*, 25(5):735-743 (2011).

Berbée, et al., "Apolipoprotein CI Enhances the Biological Response to LPS Via the CD14/TLR4 Pathway by LPS-Binding Elements in Both Its N- and C-Terminal Helix." *Journal of Lipid Research*, 51(7):1943-1952 (2010).

Berger and Chiolero, "Antioxidant Supplementation in Sepsis and Systemic Inflammatory Response Syndrome." *Crit Care Med*, 35(9 Suppl):S584-590 (2007).

Bernard, et al., "Efficacy and Safety of Recombinant Human Activated Protein C for Severe Sepsis." *N Engl J Med*, 344(10):699-709 (2001).

Bernard "Statins for Acutely Hospitalized Patients: Randomized Controlled Trials Are Long Overdue." *Crit Care*, 14(2):141 (2010).

Bernard and Bernard "The Immune Response: Targets for the Treatment of Severe Sepsis." *International Journal of Inflammation*, 2012:697592 (2012).

Berr, "Cognitive Impairment and Oxidative Stress in the Elderly: Results of Epidemiological Studies." *Biofactors*, 13(1-4):205-209 (2000).

Beutz, "Community-Acquired Pneumonia and Sepsis." *Clinics in Chest Medicine* 26(19-28) (2005).

Bjorkhem-Bergman, et al., "Statin Treatment and Mortality in Bacterial Infections—a Systematic Review and Meta-Analysis." *PLoS One*, 5(5):e10702 (2010).

Bo, et al., "Granulocyte-Colony Stimulating Factor (G-CSF) and Granulocyte-Macrophage Colony Stimulating Factor (Gm-CSF) for Sepsis: A Meta-Analysis." *Critical Care*, 15(1):R58 (2011).

Bone, et al., "A Second Large Controlled Clinical Study of E5, a Monoclonal Antibody to Endotoxin: Results of a Prospective, Multicenter, Randomized, Controlled Trial. The E5 Sepsis Study Group." *Crit Care Med*, 23(6):994-1006 (1995).

Brazil, "Macrophage LXRS Inhibit Atherosclerosis." *Nat Rev Drug Discov*, 1(11):840-840 (2002).

Brocklehurst, et al., "Treatment of Neonatal Sepsis with Intravenous Immune Globulin." *New England Journal of Medicine*, 365(13):1201-1211 (2011).

Bruunsgaard, et al., "Impaired Production of Proinflammatory Cytokines in Response to Lipopolysaccharide (LPS) Stimulation in Elderly Humans." *Clinical and Experimental Immunology*, 118(2):235-241 (1999).

Cao, et al., "Additions to the Human Plasma Proteome Via a Tandem Mars Depletion ITRAQ-Based Workflow." *International Journal of Proteomics*, 2013:8 (2013).

Capp, et al., "Effective Antibiotic Treatment Prescribed by Emergency Physicians in Patients Admitted to the Intensive Care Unit with Severe Sepsis or Septic Shock: Where Is the Gap?". *J Emerg Med*, 41(6):573-580 (2011).

Carrigan, et al., "Toward Resolving the Challenges of Sepsis Diagnosis." *Clin Chem*, 50(8):1301-1314 (2004).

Carvalho and Trotta, "[Advances in Sepsis Diagnosis and Treatment]." *J Pediatr (Rio J)*, 79 Suppl 2:S195-204 (2003).

Casserly, et al., "Evaluating the Use of Recombinant Human Activated Protein C in Adult Severe Sepsis: Results of the Surviving Sepsis Campaign." *Crit Care Med*, 40(5):1417-1426 (2012).

Chai, et al., "Rxr Agonists Inhibit High-Glucose-Induced Oxidative Stress by Repressing Pkc Activity in Human Endothelial Cells." *Free Radic Biol Med*, 44(7):1334-1347 (2008).

Chen, et al., "Role of Retinoid-X Receptor-Alpha in the Suppression of Rat Bile Acid Coenzyme a-Amino Acid N-Acyltransferase in Liver During Sepsis." *Shock*, 28(1):65-70 (2007).

Christensen, et al., "Preadmission Statin Use and One-Year Mortality among Patients in Intensive Care—a Cohort Study." *Crit Care*, 14(2):R29 (2010).

Christoffersen and Nielsen "Apolipoprotein M—a New Biomarker in Sepsis." *Critical Care*, 16(3):126-126 (2012).

Cohen, "The Immunopathogenesis of Sepsis." *Nature*, 420(6917):885-891 (2002).

Cohen and Carlet, "Intersept: An International, Multicenter, Placebo-Controlled Trial of Monoclonal Antibody to Human Tumor Necro-

(56) References Cited

OTHER PUBLICATIONS sis Factor-Alpha in Patients with Sepsis. International Sepsis Trial Study Group." *Crit Care Med*, 24(9):1431-1440 (1996).
Cohen, et al., "Coagulation and Activation of Inflammatory Pathways in the Development of Functional Decline and Mortality in the Elderly." *Am J Med*, 114(3):180-187 (2003).
Cronin, et al., "Corticosteroid Treatment for Sepsis: A Critical Appraisal and Meta-Analysis of the Literature." *Crit Care Med*, 23(8):1430-1439 (1995).
Cunha, "Antibiotic Treatment of Sepsis." *Med Clin North Am*, 79(3):551-558 (1995).
Davis, "Improved Diagnostic Approaches to Infection/Sepsis Detection." *Expert Review of Molecular Diagnostics*, 5(2):193-207 (2005).
Dellinger et al., "Surviving Sepsis Campaign: International Guidelines for Management of Severe Sepsis and Septic Shock: 2012." *Crit Care Med*, 41(2):580-637 (2013A).
Dellinger et al., "Surviving Sepsis Campaign: International Guidelines for Management of Severe Sepsis and Septic Shock: 2012." *Crit Care Med*, 41(2):580-637 (2013B).
Diefenbach, et al., "Requirement for Type 2 NO Synthase for IL-12 Signaling in Innate Immunity." *Science*, 284(5416):951-955 (1999).
Docke, et al., "Monocyte Deactivation in Septic Patients: Restoration by IFN-Gamma Treatment." *Nat Med*, 3(6):678-681 (1997).
Downie, et al., "Community-Acquired Neonatal and Infant Sepsis in Developing Countries: Efficacy of Who's Currently Recommended Antibiotics—Systematic Review and Meta-Analysis." *Arch Dis Child*, 98(2):146-154 (2013).
Dremsizov, et al., "Severe Sepsis in Community-Acquired Pneumonia." *CHEST*, 129(4):968-978 (2006).
El-Nawawy, et al., "Intravenous Polyclonal Immunoglobulin Administration to Sepsis Syndrome Patients: A Prospective Study in a Pediatric Intensive Care Unit." *J Trop Pediatr*, 51(5):271-278 (2005).
Fink, "Adoptive Immunotherapy of Gram-Negative Sepsis: Use of Monoclonal Antibodies to Lipopolysaccharide." *Crit Care Med*, 21(2 Suppl):S32-39 (1993).
Fulop, Role of Immunosenescence in Infections and Sepsis in the Elderly. In Fulop (Ed.), *Handbook on Immunosenescence* (pp. 965-977). Springer Netherlands, (2009).
Girard and Ely, "Bacteremia and Sepsis in Older Adults." *Clin Geriatr Med*, 23(3):633-647, viii (2007).
Goronzy and Weyand "Understanding Immunosenescence to Improve Responses to Vaccines." *Nat Immunol*, 14(5):428-436 (2013).
Greenman, et al., "A Controlled Clinical Trial of E5 Murine Monoclonal IgM Antibody to Endotoxin in the Treatment of Gram-Negative Sepsis. The Xoma Sepsis Study Group." *Jama*, 266(8):1097-1102 (1991).
Grolleau-Julius, et al., "Mechanisms of Murine Dendritic Cell Antitumor Dysfunction in Aging." *Cancer Immunology, Immunotherapy*, 58(12):1935-1939 (2009).
Gustot, "Multiple Organ Failure in Sepsis: Prognosis and Role of Systemic Inflammatory Response." *Curr Opin Crit Care*, 17(2):153-159 (2011).
Hackam, et al., "Statins and Sepsis in Patients with Cardiovascular Disease: A Population-Based Cohort Analysis." *The Lancet*, 367(9508):413-418 (2006).
Harbarth, et al., "Inappropriate Initial Antimicrobial Therapy and Its Effect on Survival in a Clinical Trial of Immunomodulating Therapy for Severe Sepsis." *Am J Med*, 115(7):529-535 (2003).
Hotchkiss, "The Pathophysiology and Treatment of Sepsis." *New England Journal of Medicine*, 348(2):138-150 (2003).
Hotchkiss, et al., "Immunosuppression in Sepsis: A Novel Understanding of the Disorder and a New Therapeutic Approach." *Lancet Infect Dis*, 13(3):260-268 (2013).
Ibsen and Perner, "Perioperative Treatment of Patients with Sepsis." *Current Opinion in Anesthesiology*, 26(3):348-353 (2013).
Janda, et al., "The Effect of Statins on Mortality from Severe Infections and Sepsis: A Systematic Review and Meta-Analysis." *Journal of Critical Care*, 25(4):656.e657-656.e622 (2010).

Joannidis, "Continuous Renal Replacement Therapy in Sepsis and Multisystem Organ Failure." *Semin Dial*, 22(2):160-164 (2009).
Joseph, et al., "Synthetic LXR Ligand Inhibits the Development of Atherosclerosis in Mice." *Proc Natl Acad Sci USA*, 99(11):7604-7609 (2002).
Kale, et al., "The Effects of Age on Inflammatory and Coagulation-Fibrinolysis Response in Patients Hospitalized for Pneumonia." *PLoS One*, 5(11):e13852 (2010).
Kalenka, et al., "Changes in the Serum Proteome of Patients with Sepsis and Septic Shock." *Anesth Analg*, 103(6):1522-1526 (2006).
Kaplan, et al., "Hospitalized Community-Acquired Pneumonia in the Elderly: Age- and Sex-Related Patterns of Care and Outcome in the United States." *Am J Respir Crit Care Med*, 165(6):766-772 (2002).
Karolkiewicz, et al., "Oxidative Stress and Antioxidant Defense System in Healthy, Elderly Men: Relationship to Physical Activity." *The Aging Male*, 6(2):100-105 (2003).
Karumbi, et al., "Topical Umbilical Cord Care for Prevention of Infection and Neonatal Mortality." *Pediatr Infect Dis J*, 32(1):78-83 (2013).
Kaspereit, et al., "The Effect of Fibrinogen Concentrate Administration on Coagulation Abnormalities in a Rat Sepsis Model." *Blood Coagul Fibrinolysis*, 15(1):39-43 (2004).
Kattan, et al., "Apolipoprotein E-Mediated Immune Regulation in Sepsis." *J Immunol*, 181(2):1399-1408 (2008).
Kellum, et al., "Understanding the Inflammatory Cytokine Response in Pneumonia and Sepsis: Results of the Genetic and Inflammatory Markers of Sepsis (GenIMS) Study." *Arch Intern Med*, 167(15):1655-1663 (2007).
Khovidhunkit, et al., "Effects of Infection and Inflammation on Lipid and Lipoprotein Metabolism: Mechanisms and Consequences to the Host." *J Lipid Res*, 45(7):1169-1196 (2004).
Kolls, "Oxidative Stress in Sepsis: A Redox Redux." *Journal of Clinical Investigation*, 116(4):860-863 (2006).
Kreymann, et al., "Use of Polyclonal Immunoglobulins as Adjunctive Therapy for Sepsis or Septic Shock." *Crit Care Med*, 35(12):2677-2685 (2007).
Kumar, et al., "Duration of Hypotension before Initiation of Effective Antimicrobial Therapy Is the Critical Determinant of Survival in Human Septic Shock." *Crit Care Med*, 34(6):1589-1596 (2006).
Kumaraswamy, et al., "Decreased Plasma Concentrations of Apolipoprotein M in Sepsis and Systemic Inflammatory Response Syndromes." *Crit Care*, 16(2):R60 (2012).
Kurokawa, et al., "Apoptosis Inhibitor of Macrophage (AIM) Is Required for Obesity-Associated Recruitment of Inflammatory Macrophages into Adipose Tissue." *Proc Natl Acad Sci USA*, 108(29):12072-12077 (2011).
Lacorte, et al., "Activation of CAAT Enhancer-Binding Protein Delta (C/EBPdelta) by Interleukin-1 Negatively Influences Apolipoprotein C-III Expression." *J Biol Chem*, 272(38):23578-23584 (1997).
Larrede, et al., "Stimulation of Cholesterol Efflux by LXR Agonists in Cholesterol-Loaded Human Macrophages Is ABCA1-Dependent but ABCG1-Independent." *Arterioscler Thromb Vasc Biol*, 29(11):1930-1936 (2009).
Laupland, et al., "Polyclonal Intravenous Immunoglobulin for the Treatment of Severe Sepsis and Septic Shock in Critically Ill Adults: A Systematic Review and Meta-Analysis." *Crit Care Med*, 35(12):2686-2692 (2007).
Leone, et al., "Ventilator-Associated Pneumonia: Breaking the Vicious Circle of Antibiotic Overuse." *Crit Care Med*, 35(2):379-385 (2007).
Levy, et al., "2001 SCCM/ESICM/ACCP/ATS/SIS International Sepsis Definitions Conference." *Intensive Care Med*, 29(4):530-538 (2003).
Lin, et al., "Serum Thrombomodulin Level Relates to the Clinical Course of Disseminated Intravascular Coagulation, Multiorgan Dysfunction Syndrome, and Mortality in Patients with Sepsis." *Crit Care Med*, 36(3):683-689 (2008).
Macdonald, et al., "Oxidative Stress and Gene Expression in Sepsis." *Br J Anaesth*, 90(2):221-232 (2003).
Mangelsdorf and Evans, "The RXR Heterodimers and Orphan Receptors." *Cell*, 83(6):841-850 (1995).

(56) References Cited

OTHER PUBLICATIONS

Markovitz, et al., "A Retrospective Cohort Study of Prognostic Factors Associated with Outcome in Pediatric Severe Sepsis: What Is the Role of Steroids?" *Pediatr Crit Care Med*, 6(3):270-274 (2005).
Martin, et al., "The Epidemiology of Sepsis in the United States from 1979 through 2000." *New England Journal of Medicine*, 348(16):1546-1554 (2003).
Martin, et al., "The Effect of Age on the Development and Outcome of Adult Sepsis." *Crit Care Med*, 34(1):15-21 (2006).
Masia, et al., "Serum Concentrations of Lipopolysaccharide-Binding Protein as a Biochemical Marker to Differentiate Microbial Etiology in Patients with Community-Acquired Pneumonia." *Clin Chem*, 50(9):1661-1664 (2004).
McCloskey, et al., "Treatment of Septic Shock with Human Monoclonal Antibody Ha-1a: A Randomized, Double-Blind, Placebo-Controlled Trial." *Annals of Internal Medicine*, 121(1):1-5 (1994).
McDonald, et al., "Aging Is Associated with Impaired Thrombus Resolution in a Mouse Model of Stasis Induced Thrombosis." *Thromb Res*, 125(1):72-78 (2010).
Meisel, et al., "Granulocyte-Macrophage Colony-Stimulating Factor to Reverse Sepsis-Associated Immunosuppression: A Double-Blind, Randomized, Placebo-Controlled Multicenter Trial." *Am J Respir Crit Care Med*, 180(7):640-648 (2009).
Micek, et al., "Pseudomonas Aeruginosa Bloodstream Infection: Importance of Appropriate Initial Antimicrobial Treatment." *Antimicrob Agents Chemother*, 49(4):1306-1311 (2005).
Myhre, et al., "Liver X Receptor Is a Key Regulator of Cytokine Release in Human Monocytes." *Shock*, 29(4):468-474 (2008).
Nadel, et al., "Drotrecogin Alfa (Activated) in Children with Severe Sepsis: A Multicentre Phase III Randomised Controlled Trial." *Lancet*, 369(9564):836-843 (2007).
Niederman, "De-Escalation Therapy in Ventilator-Associated Pneumonia." *Curr Opin Crit Care*, 12(5):452-457 (2006).
Opal, et al., "The Immunopathogenesis of Sepsis in Elderly Patients." *Clin Infect Dis*, 41 Suppl 7:S4-512 (2005).
Patel and Balk, "Systemic Steroids in Severe Sepsis and Septic Shock." *Am J Respir Crit Care Med*, 185(2):133-139 (2012).
Phetteplace, et al., "*Escherichia coli* Sepsis Increases Hepatic Apolipoprotein B Secretion by Inhibiting Degradation." *Lipids*, 35(10):1079-1085 (2000).
Podnos, et al., "Intra-Abdominal Sepsis in Elderly Persons." *Clin Infect Dis*, 35(1):62-68 (2002).
Póvoa, et al., "C-Reactive Protein, an Early Marker of Community-Acquired Sepsis Resolution: A Multi-Center Prospective Observational Study." *Critical Care*, 15(4):R169-R169 (2011).
Proulx, et al., "Delays in the Administration of Antibiotics Are Associated with Mortality from Adult Acute Bacterial Meningitis." *Qjm*, 98(4):291-298 (2005).
Qiu, et al., "The Evolving Experience with Therapeutic TNF Inhibition in Sepsis: Considering the Potential Influence of Risk of Death." *Expert opinion on investigational drugs*, 20(11):1555-1564 (2011).
Ranieri, et al., "Drotrecogin Alfa (Activated) in Adults with Septic Shock." *New England Journal of Medicine*, 366(22):2055-2064 (2012).
Ren, et al., "The Alterations of Mouse Plasma Proteins During Septic Development." *J Proteome Res*, 6(7):2812-2821 (2007).
Rice and Bernard, "Therapeutic Intervention and Targets for Sepsis." *Annual Review of Medicine*, 56(1):225-248 (2005).
Rice, et al., "A Randomized, Double-Blind, Placebo-Controlled Trial of Tak-242 for the Treatment of Severe Sepsis." *Crit Care Med*, 38(8):1685-1694 (2010).
Rivers, et al., "Early Biomarker Activity in Severe Sepsis and Septic Shock and a Contemporary Review of Immunotherapy Trials: Not a Time to Give up, but to Give It Earlier." *Shock*, 39(2):127-137 (2013).
Ross, et al., "Multiplexed Protein Quantitation in *Saccharomyces cerevisiae* Using Amine-Reactive Isobaric Tagging Reagents." *Mol Cell Proteomics*, 3(12):1154-1169 (2004).

Sadeghi, et al., "Phenotypic and Functional Characteristics of Circulating Monocytes of Elderly Persons." *Experimental Gerontology*, 34(8):959-970 (1999).
Salomao, et al., "TLR Signaling Pathway in Patients with Sepsis." *Shock*, 30 Suppl 1:73-77 (2008).
Shen, et al., "Sepsis Plasma Protein Profiling with Immunodepletion, Three-Dimensional Liquid Chromatography Tandem Mass Spectrometry, and Spectrum Counting." *J Proteome Res*, 5(11):3154-3160 (2006).
Soares, et al., "Differential Proteomics of the Plasma of Individuals with Sepsis Caused by Acinetobacter Baumannii." *J Proteomics*, 73(2):267-278 (2009).
Sprung, et al., "Hydrocortisone Therapy for Patients with Septic Shock." *New England Journal of Medicine*, 358(2):111-124 (2008).
Stephensen, et al., "Disruption of Rxra Gene in Thymocytes and T Lymphocytes Modestly Alters Lymphocyte Frequencies, Proliferation, Survival and T Helper Type 1/Type 2 Balance." *Immunology*, 121(4):484-498 (2007).
Sunder-Plassmann, et al., "Disseminated Intravascular Coagulation and Decrease in Fibrinogen Levels Induced by Vincristine/Prednisolone Therapy of Lymphoid Blast Crisis of Chronic Myeloid Leukemia." *Ann Hematol*, 62(5):169-173 (1991).
Sureda, et al., "Antiapoptotic Drugs: A Therapautic Strategy for the Prevention of Neurodegenerative Diseases." *Curr Pharm Des*, 17(3):230-245 (2011).
Takeuchi, et al., "Retinoid X Receptor Agonists Modulate Foxp3(+) Regulatory T Cell and Th17 Cell Differentiation with Differential Dependence on Retinoic Acid Receptor Activation." *J Immunol*, 191(7):3725-3733 (2013).
Thongboonkerd, et al., "Altered Plasma Proteome During an Early Phase of Peritonitis-Induced Sepsis." *Clin Sci (Lond)*, 116(9):721-730 (2009).
Tschaikowsky, et al., "Lipopolysaccharide-Binding Protein for Monitoring of Postoperative Sepsis: Complemental to C-Reactive Protein or Redundant?" *PLoS One*, 6(8):e23615 (2011).
Turgeon, et al., "Meta-Analysis: Intravenous Immunoglobulin in Critically Ill Adult Patients with Sepsis." *Ann Intern Med*, 146(3):193-203 (2007).
Turnbull, et al., "Effects of Aging on the Immunopathological Response to Sepsis." *Crit Care Med*, 37(3):1018-1023 (2009).
Turnidge, "Impact of Antibiotic Resistance on the Treatment of Sepsis." *Scand J Infect Dis*, 35(9):677-682 (2003).
Van 't Veer and van der Poll, "Keeping Blood Clots at Bay in Sepsis." *Nat Med*, 14(6):606-608 (2008).
Venet, et al., "Assessment of Plasmatic Immunoglobulin G, A and M Levels in Septic Shock Patients." *Int Immunopharmacol*, 11(12):2086-2090 (2011).
Villar, et al., "Serum Lipopolysaccharide Binding Protein Levels Predict Severity of Lung Injury and Mortality in Patients with Severe Sepsis." *PLoS One*, 4(8):e6818 (2009).
Vincent and Sakr, "SOFA So Good for Predicting Long-Term Outcomes." *Resuscitation*, 83(5):537-538 (2006).
Ward, et al., "Manipulation of the Complement System for Benefit in Sepsis." *Crit Care Res Pract*, 2012:427607 (2012).
Ware, et al., "Significance of Von Willebrand Factor in Septic and Nonseptic Patients with Acute Lung Injury." *Am J Respir Crit Care Med*, 170(7):766-772 (2004).
Warren, et al., "Caring for the Critically Ill Patient. High-Dose Antithrombin III in Severe Sepsis: A Randomized Controlled Trial." *Jama*, 286(15):1869-1878 (2001).
Welty-Wolf, et al., "Proinflammatory Cytokines Increase in Sepsis after Anti-Adhesion Molecule Therapy." *Shock*, 13(5):404-409 (2000).
Westerterp, et al., "Apolipoprotein C-I Is Crucially Involved in Lipopolysaccharide-Induced Atherosclerosis Development in Apolipoprotein E-Knockout Mice." *Circulation*, 116(19):2173-2181 (2007).
Westerterp, et al., "Apolipoprotein CI Aggravates Atherosclerosis Development in Apoe-Knockout Mice Despite Mediating Cholesterol Efflux from Macrophages." *Atherosclerosis*, 195(1):e9-16 (2007).
Wick and Grubeck-Loebenstein, "The Aging Immune System: Primary and Secondary Alterations of Immune Reactivity in the Elderly." *Exp Gerontol*, 32(4-5):401-413 (1997).

(56) References Cited

OTHER PUBLICATIONS

Wilson, et al., "Nano-Lc in Proteomics: Recent Advances and Approaches." *Bioanalysis*, 7(14):1799-1815 (2015).
Wong, et al., "A Multibiomarker-Based Outcome Risk Stratification Model for Adult Septic Shock." *Crit Care Med*, 42(4):781-789 (2014).
Wu, et al., "High-Density Lipoproteins in Sepsis and Septic Shock: Metabolism, Actions, and Therapeutic Applications." *Shock*, 21(3):210-221 (2004).
Yamakawa, et al., "Treatment Effects of Recombinant Human Soluble Thrombomodulin in Patients with Severe Sepsis: A Historical Control Study." *Critical Care*, 15(3):R123-R123 (2011).
Yamamoto, et al., "Aging Accelerates Endotoxin-Induced Thrombosis: Increased Responses of Plasminogen Activator Inhibitor-1 and Lipopolysaccharide Signaling with Aging." *The American Journal of Pathology*, 161(5):1805-1814 (2002).
Zhao and Dahlman-Wright "Liver X Receptor in Cholesterol Metabolism." *J Endocrinol*, 204(3):233-240 (2010).
Ziegler, et al., "Treatment of Gram-Negative Bacteremia and Septic Shock with Ha-1a Human Monoclonal Antibody against Endotoxin. A Randomized, Double-Blind, Placebo-Controlled Trial. The Ha-1a Sepsis Study Group." *N Engl J Med*, 324(7):429-436 (1991).
Zweigner, et al., "High Concentrations of Lipopolysaccharide-Binding Protein in Serum of Patients with Severe Sepsis or Septic Shock Inhibit the Lipopolysaccharide Response in Human Monocytes." *Blood*, 98(13):3800-3808 (2001).
Brun, et al., "Exposure to Bacterial Cell Wall Products Triggers an Inflammatory Phenotype in Hepatic Stellate Cells." *American Journal of Physiology-Gastrointestinal and Liver Physiology*, 289(3):G571-G578 (2005).
Cao, et al., "Proteomics Reveals Age-Related Differences in the Host Immune Response to Sepsis." *Journal of proteome research*, 13(2):422-432 (2013).
Goldblum, et al., "Bacterial Lipopolysaccharide Induces Actin Reorganization, Intercellular Gap Formation, and Endothelial Barrier Dysfunction in Pulmonary Vascular Endothelial Cells: Concurrent F-Actin Depolymerization and New Actin Synthesis." *Journal of cellular physiology*, 157(1):13-23 (1993).
Reade, et al., "Differences in Immune Response May Explain Lower Survival among Older Men with Pneumonia." *Crit Care Med*, 37(5):1655 (2009).
Su, et al., "Identification of Novel Biomarkers for Sepsis Prognosis Via Urinary Proteomic Analysis Using iTRAQ Labeling and 2D-LC-MS/MS." *PLoS One*, 8(1):e54237 (2013).
Wang, et al., "Downregulation of Liver X Receptor-A in Mouse Kidney and HK-2 Proximal Tubular Cells by LPS and Cytokines." *Journal of lipid research*, 46(11):2377-2387 (2005).
Wang, et al., "Inhibition of Clathrin/Dynamin-Dependent Internalization Interferes with LPS-Mediated TRAM-TRIF-Dependent Signaling Pathway." *Cellular immunology*, 274(1):121-129 (2012).
Feng, et al., "Cleavage of Rip3 Inactivates Its Caspase-Independent Apoptosis Pathway by Removal of Kinase Domain." *Cell Signal*, 19(10):2056-2067 (2007).

Kasof, et al., "The Rip-Like Kinase, Rip3, Induces Apoptosis and NF-KappaB Nuclear Translocation and Localizes to Mitochondria." *FEBS Lett*, 473(3):285-291 (2000).
Li, et al., "The RIP1/RIP3 Necrosome Forms a Functional Amyloid Signaling Complex Required for Programmed Necrosis." And supplemental information. *Cell*, 150(2):339-350 (2012).
Sun, et al., "RIP3, a Novel Apoptosis-Inducing Kinase." *J Biol Chem*, 274(24):16871-16875 (1999).
Tait, et al., "Widespread Mitochondrial Depletion Via Mitophagy Does Not Compromise Necroptosis." *Cell Rep*, 5(4):878-885 (2013).
Yang, et al., "RIP3 beta and RIP3 Gamma, Two Novel Splice Variants of Receptor-Interacting Protein 3 (Rip3), Downregulate Rip3-Induced Apoptosis." *Biochem Biophys Res Commun*, 332(1):181-187 (2005).
Almirall, et al., "Contribution of C-Reactive Protein to the Diagnosis and Assessment of Severity of Community-Acquired Pneumonia." *Chest*, 125(4):1335-1342 (2004).
Andaluz-Ojeda, et al., "A Combined Score of Pro- and Anti-Inflammatory Interleukins Improves Mortality Prediction in Severe Sepsis." *Cytokine*, 57(3):332-336 (2012).
Anderson and Anderson "The Human Plasma Proteome: History, Character, and Diagnostic Prospects." *Mol Cell Proteomics*, 1(11):845-867 (2002).
Donadello, et al., "Supar as a Prognostic Biomarker in Sepsis." *BMC Med*, 10:2 (2012).
Gamez-Diaz, et al., "Diagnostic Accuracy of HMGB-1, s-TREM-1, and CD64 as Markers of Sepsis in Patients Recently Admitted to the Emergency Department." *Acad Emerg Med*, 18(8):807-815 (2011).
Gong, et al., "Serum Proteome Alteration of Severe Sepsis in the Treatment of Continuous Renal Replacement Therapy." *Nephrol Dial Transplant*, 24(10):3108-3114 (2009).
Grion, et al., "Lipoproteins and CETP Levels as Risk Factors for Severe Sepsis in Hospitalized Patients." *Eur J Clin Invest*, 40(4):330-338 (2010).
Kibe, et al., "Diagnostic and Prognostic Biomarkers of Sepsis in Critical Care." *J Antimicrob Chemother*, 66 Suppl 2:ii33-40 (2011).
Moore, et al., "A Pilot Study Assessing the Prognostic Value of Ck18 and nDNA Biomarkers in Severe Sepsis Patients." *Clin Drug Investig*, 32(3):179-187 (2012).
Schulte, et al., "Circulating Levels of Peroxiredoxin 4 as a Novel Biomarker of Oxidative Stress in Patients with Sepsis." *Shock*, 35(5):460-465 (2011).
Ware, et al., "Plasma Biomarkers of Oxidant Stress and Development of Organ Failure in Severe Sepsis." *Shock*, 36(1):12-17 (2011).
Cao, Zhiyun, "Understanding Immunosenescence in Aging-Related Diseases With Quantitative Proteomics." CaoA: Doctoral Dissertation, University of Pittsburgh, CaoB: Publication Year: 2014.
Cao, Zhiyun, "Understanding Immunosenescence in Aging-Related Diseases With Quantitative Proteomics." CaoA: Doctoral Dissertation, University of Pittsburgh, CaoB: Publication Year: 2014, publication date 2014a.

\* cited by examiner

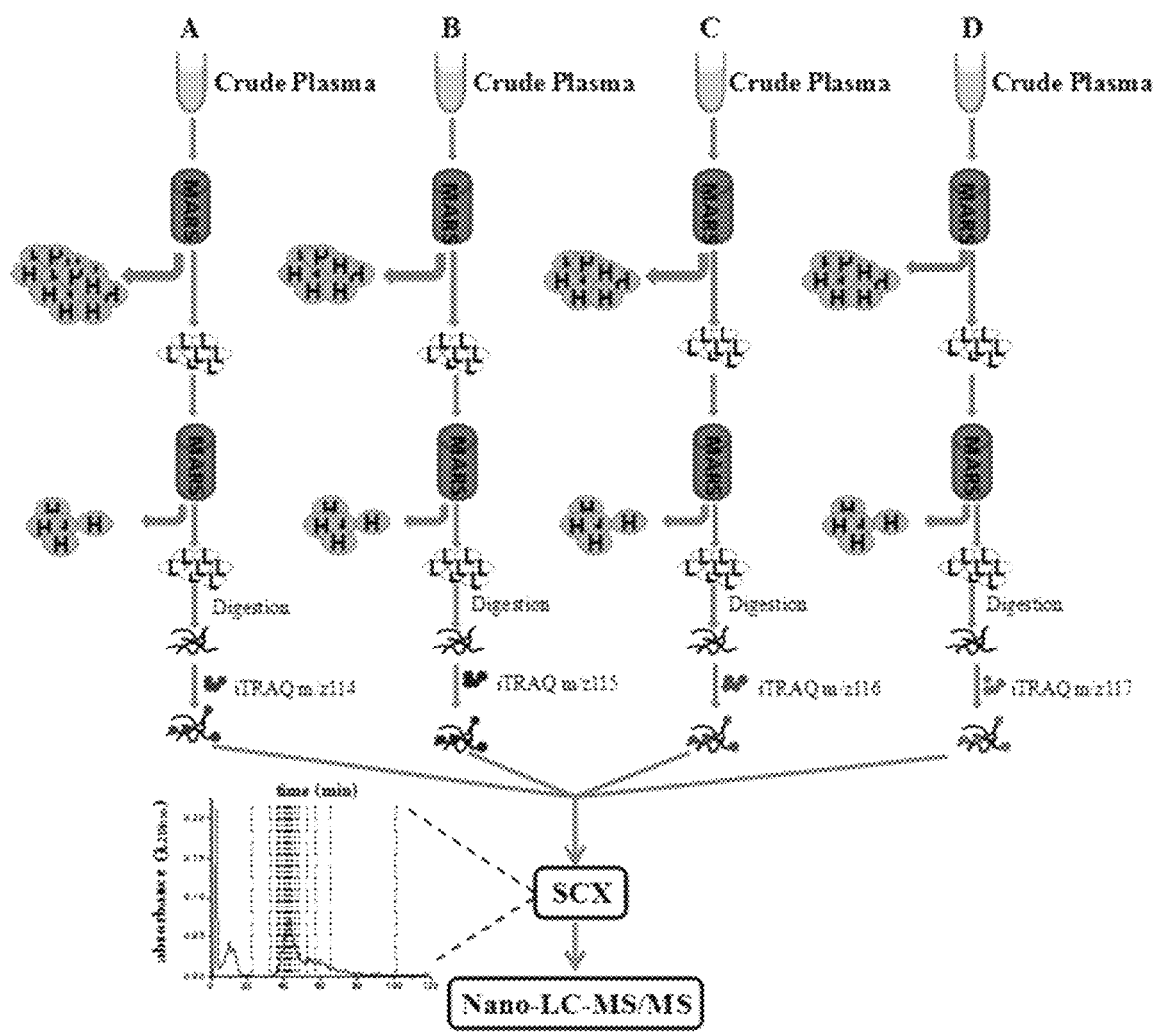
FIG 1A - D

Figures 2A - B

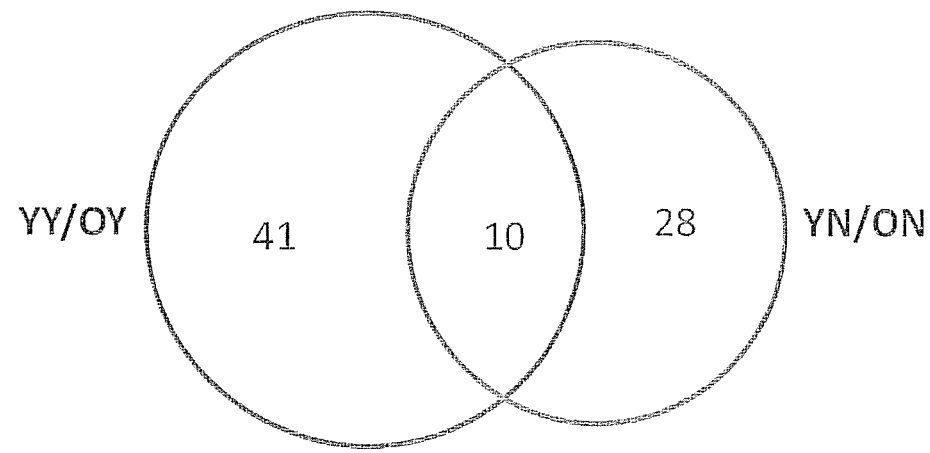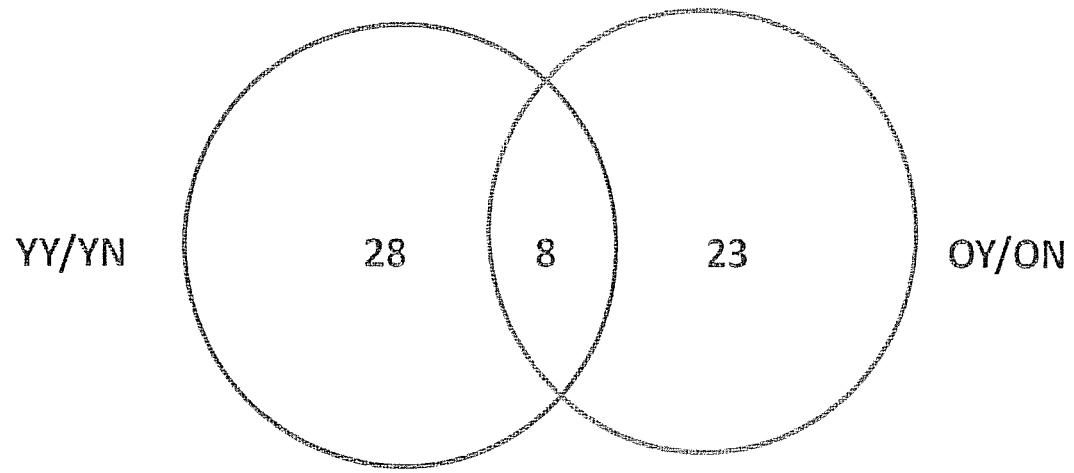
Figure 3

```
SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Asp Leu Ala Thr Val Tyr Val Asp Val Leu Lys
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Ala Glu Phe Gln Asp Ala Leu Glu Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3
```

```
Tyr Tyr Thr Tyr Leu Ile Met Asn Lys
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Gly Trp Val Thr Asp Gly Phe Ser Ser Leu Lys
1               5                   10
```

US 10,948,497 B2

PROTEOMIC BIOMARKERS OF SEPSIS IN ELDERLY PATIENTS

STATEMENT OF GOVERNMENTAL SUPPORT

This invention was made with government support awarded by the National Institute of General Medical Sciences, National Institutes of Health (grant number R01 GM61992). The government has certain rights in the invention.

FIELD OF THE INVENTION

The present invention is related to the field of sepsis. In particular, the invention identifies differences in global protein expression that are either age-related and/or outcome-related. These differences represent biomarkers to guide risk potential, therapy, monitoring and diagnosis.

BACKGROUND

Sepsis is a systemic infection that leads to immune dyshomeostasis, organ failure, and in severe cases morbidity. Cohen J, "The immunopathgenesis of sepsis" *Nature* 420:885-891 (2002). Approximately 750,000 people develop sepsis annually commonly after an initial diagnosis of community-acquired pneumonia (CAP). Angus et al., "Epidemiology of severe sepsis in the United States: analysis of incidence, outcome, and associated costs of care" *Crit Care Med* 29:1303-1310 (2001). Recently it has been reported that mortality in sepsis patients increases with age, although there is no direct correlation in the expression levels of key cytokines and transcription factors. Martin et al., "The effect of age on the development and outcome of adult sepsis" *Crit Care Med* 34:15-21 (2006).

What is needed in the art is a quantitative proteomics platform in order to identify age- and outcome-related differences in global protein expression in plasma obtained from sepsis patients.

SUMMARY

The present invention is related to the field of sepsis. In particular, the invention identifies differences in global protein expression that are either age-related and/or outcome-related. These differences represent biomarkers to guide risk potential, therapy, monitoring and diagnosis.

In one embodiment, the present invention contemplates a method, comprising: a) providing; i) at least one biological sample derived from an elderly patient suspected of having an infection; ii) at least one peptide isolated from said at least one biological sample, wherein said at least one isolated peptide comprises at least one isobaric tag for relative and absolute quantitation (iTRAQ) reporter ion; iii) a system comprising a liquid chromatography column and a mass spectrometer; and iv) a control proteomic pathway expression profile; b) contacting said at least one iTRAQ-peptide with said system to create at least one iTRAQ-peptide analysis spectrum; c) processing said at least one iTRAQ-peptide analysis spectrum to create a sepsis proteomic pathway expression profile, wherein said sepsis proteomic pathway expression profile comprises at least one over-expressed protein pathway as compared to said control proteomic pathway expression profile; and d) diagnosing said patient with severe sepsis upon identification of said over-expressed protein pathway. In one embodiment, the over-expressed protein pathway is a liver retinoid X receptor activation pathway. In one embodiment, the liver retinoid X receptor activation pathway is about ten-fold over-expressed as compared to said control proteomic pathway expression profile. In one embodiment, the over-expressed protein pathway is an acute phase response signaling pathway. In one embodiment, the acute phase response signaling pathway is about eight-fold over-expressed as compared to said control proteomic pathway expression profile. In one embodiment, the over-expressed protein pathway is an atherosclerosis signaling pathway. In one embodiment, the atherosclerosis signaling pathway is about seven-fold over-expressed as compared to said control proteomic pathway expression profile. In one embodiment, the over-expressed protein pathway is an interleukin-2 signaling pathway. In one embodiment, the interleukin-2 signaling pathway is about seven-fold over-expressed as compared to said control proteomic pathway expression profile. In one embodiment, the over-expressed protein pathway is a nitric oxide/oxygen reactive species pathway. In one embodiment, the nitric oxide/oxygen reactive species pathway is about seven-fold over-expressed as compared to said control proteomic pathway expression profile. In one embodiment, the over-expressed protein pathway is a clathrin-mediated endocytosis signaling pathway. In one embodiment, the clathrin-mediated endocytosis signaling pathway is about seven-fold over-expressed as compared to said control proteomic pathway expression profile. In one embodiment, the over-expressed protein pathway is an lipopolysacharride/interleukin-1 retinoid X receptor inhibition pathway. In one embodiment, the lipopolysacharride/interleukin-1 retinoid X receptor inhibition pathway is about three-fold over-expressed as compared to said control proteomic pathway expression profile. In one embodiment, the over-expressed protein pathway is an farnesoid X receptor activation pathway. In one embodiment, the farnesoid X receptor activation pathway is about two-fold over-expressed as compared to said control proteomic pathway expression profile. In one embodiment, the over-expressed protein pathway is a hepatic stellate cell activation pathway. In one embodiment, the hepatic stellate cell activation pathway is about two-fold over-expressed as compared to said control proteomic pathway expression profile. In one embodiment, the over-expressed protein pathway is an actin cytoskeleton signaling pathway. In one embodiment, the actin cytoskeleton signaling pathway is about two-fold over-expressed as compared to said control proteomic pathway expression profile.

In one embodiment, the present invention contemplates a method, comprising: a) providing; i) at least one biological sample derived from a young patient suspected of having an infection; ii) at least one peptide isolated from said at least one biological sample, wherein said at least one isolated peptide comprises at least one isobaric tag for relative and absolute quantitation (iTRAQ) reporter ion; iii) a system comprising a liquid chromatography column and a mass spectrometer; and iv) a control proteomic pathway expression profile; b) contacting said at least one iTRAQ-peptide with said system to create at least one iTRAQ-peptide analysis spectrum; c) processing said at least one iTRAQ-peptide analysis spectrum to create a sepsis proteomic pathway expression profile, wherein said sepsis proteomic pathway expression profile comprises at least one over-expressed protein pathway as compared to said control proteomic pathway expression profile; and d) diagnosing said patient with severe sepsis upon identification of said over-expressed protein pathway. In one embodiment, the over-expressed protein pathway is a liver retinoid X receptor activation pathway. In one embodiment, the liver retinoid X receptor pathway is about sixteen-fold over-expressed as compared to said control proteomic pathway expression profile. In one embodiment, the over-expressed protein pathway is an acute phase response signaling pathway. In one embodiment, the acute phase response signaling pathway is about sixteen-fold over-expressed as compared to said control proteomic pathway expression profile. In one embodiment, the over-expressed protein pathway is an atherosclerosis signaling pathway. In one embodiment, the atherosclerosis signaling pathway is about ten-fold over-expressed as compared to said control proteomic pathway expression profile. In one embodiment, the over-expressed protein pathway is an interleukin-2 signaling pathway. In one embodiment, the interleukin-2 signaling pathway is about ten-fold over-expressed as compared to said control proteomic pathway expression profile. In one embodiment, the over-expressed protein pathway is a nitric oxide/oxygen reactive species pathway. In one embodiment, the nitric oxide/oxygen reactive species pathway is about ten-fold over-expressed as compared to said control proteomic pathway expression profile. In one embodiment, the over-expressed protein pathway is a clathrin-mediated endocytosis signaling pathway. In one embodiment, the clathrin-mediated endocytosis signaling pathway is about eleven-fold over-expressed as compared to said control proteomic pathway expression profile. In one embodiment, the over-expressed protein pathway is a blood factor coagulation pathway. In one embodiment, the blood factor coagulation is about seven-fold over-expressed as compared to said control proteomic pathway expression profile. In one embodiment, the over-expressed protein pathway is an extrinsic prothrombin activation pathway. In one embodiment, the extrinsic prothrombin activation pathway is about five-fold over-expressed as compared to said control proteomic pathway expression profile. In one embodiment, the over-expressed protein pathway is an intrinsic prothrombin activation pathway. In one embodiment, the intrinsic prothrombin activation pathway is about five-fold over-expressed as compared to said control proteomic pathway expression profile. In one embodiment, the over-expressed protein pathway is a farnesoid X receptor activation pathway. In one embodiment, the farnesoid X receptor activation pathway is about five-fold over-expressed as compared to said control proteomic pathway expression profile. In one embodiment, the over-expressed protein pathway is an lipopolysaccharide/interleukin-1 retinoid X receptor inhibition pathway. In one embodiment, the lipopolysaccharide/interleukin-1 retinoid X receptor inhibition pathway is about six-fold over-expressed as compared to said control proteomic pathway expression profile.

In one embodiment, the present invention contemplates a method, comprising: a) providing; i) at least one biological sample derived from at least one patient suspected of having an infection; ii) at least one peptide isolated from said at least one biological sample, wherein said at least one isolated peptide comprises at least one isobaric tag for relative and absolute quantitation (iTRAQ) reporter ion; and iii) a system comprising a liquid chromatography column and a mass spectrometer; b) contacting said at least one iTRAQ-peptide with said system to create at least one iTRAQ-peptide analysis spectrum; c) processing said at least one iTRAQ-peptide analysis spectrum to create a first proteomic pathway expression profile and a second proteomic expression profile, wherein said first proteomic pathway expression profile comprises at least one differentially expressed protein pathway as compared to said second proteomic pathway expression profile; and d) diagnosing said patient with severe sepsis upon identification of said differentially expressed protein pathway. In one embodiment, the differentially expressed proteomic pathway comprises an acute phase response pathway. In one embodiment, the acute phase response pathway is differentially expressed by a ratio ranging between 8:1-16:1. In one embodiment, the differentially expressed proteomic pathway comprises a blood factor coagulation pathway. In one embodiment, the blood factor coagulation pathway is differentially expressed by a ratio ranging between 4:1-5:1. In one embodiment, the differentially expressed proteomic pathway comprises a lipid metabolism pathway. In one embodiment, the lipid metabolism pathway is differentially expressed by a ratio ranging between 6:1-10:1. In one embodiment, the differentially expressed proteomic pathway comprises an interleukin pathway. In one embodiment, the interleukin pathway is differentially over-expressed by a ratio ranging between 2:1-10:1. In one embodiment, the differentially expressed proteomic pathway comprises a nitric oxide/reactive oxygen species pathway. In one embodiment, the nitric oxide/reactive oxygen species pathway is differentially over-expressed by a ratio ranging between 7:1-10:1. In one embodiment, the at least one patient is an elderly patient without severe sepsis. In one embodiment, the at least one patient is a young patient without severe sepsis. In one embodiment, the at least one patient is an elderly patient with severe sepsis. In one embodiment, the at least one patient is a young patient with severe sepsis. In one embodiment, the infection comprises community acquired pneumonia. In one embodiment, the method further comprises treating each of said at least one patient differentially based upon said at least one sepsis proteomic expression profile.

In one embodiment, the present invention contemplates a method for age-related sepsis treatment, comprising: a) providing; i) an older patient exhibiting at least one sepsis symptom and differentially expressing at least one protein pathway as compared to a younger patient; and ii) a pharmaceutical compound that interacts with a specific drug target of said at least one differentially expressed protein pathway; b) administering said pharmaceutical compound to said patient under conditions such that said at least one sepsis symptom is reduced. In one embodiment, the at least one differentially expressed protein pathway comprises a hepatic stellate cell activation pathway. In one embodiment, the at least one differentially expressed protein pathway comprises an actin cytoskeleton signaling pathway. In one embodiment, the method further comprises a combination treatment of said pharmaceutical compound with a conventional sepsis treatment. In one embodiment, the conventional sepsis treatment is selected from the group consisting of antibiotics, inflammatory mediator inhibitors, steroids, proinflammatory cytokine inhibitors, statins, coagulation cascade inhibitors and immunostimulators. In one embodiment, the older patient ranges in age between 70-85 years old. In one embodiment, the younger patient ranges in age between 50-65 years old.

In one embodiment, the present invention contemplates a method for age-related sepsis treatment, comprising: a) providing; i) a younger patient exhibiting at least one sepsis symptom and differentially expressing at least one protein pathway as compared to an older patient; and ii) a pharmaceutical compound that interacts with a specific drug target of said at least one differentially expressed protein pathway; b) administering said pharmaceutical compound to said patient under conditions such that said at least one sepsis symptom is reduced. In one embodiment, the at least one differentially expressed protein pathway comprises a blood factor coagulation pathway. In one embodiment, the at least one differentially expressed protein pathway comprises an extrinsic prothrombin activation pathway. In one embodiment, the at least one differentially expressed protein pathway comprises an intrinsic prothrombin activation pathway. In one embodiment, the method further comprises a combination treatment of said pharmaceutical compound with a conventional sepsis treatment. In one embodiment, the conventional sepsis treatment is selected from the group consisting of antibiotics, inflammatory mediator inhibitors, steroids, proinflammatory cytokine inhibitors, statins, coagulation cascade inhibitors and immunostimulators. In one embodiment, the younger patient ranges in age between 50-65 years old. In one embodiment, the older patient ranges in age between 70-85 years old.

In one embodiment, the present invention contemplates a method, comprising: a) providing; i) at least one peptide isolated from at least one sepsis biological sample, wherein said at least one isolated peptide comprises at least one isobaric tag for relative and absolute quantitation (iTRAQ) reporter ion; and iii) a system comprising a liquid chromatography column and a mass spectrometer; b) contacting said at least one iTRAQ-peptide with said system to create at least one iTRAQ-peptide analysis spectrum; and c) processing said at least one iTRAQ-peptide analysis spectrum to create a first proteomic pathway expression profile and a second proteomic expression profile, wherein said first proteomic pathway expression profile comprises at least one differentially expressed protein pathway as compared to said second proteomic pathway expression profile. In one embodiment, the differentially expressed proteomic pathway comprises an acute phase response pathway. In one embodiment, the acute phase response pathway is differentially expressed by a ratio ranging between 8:1-16:1. In one embodiment, the differentially expressed proteomic pathway comprises a blood factor coagulation pathway. In one embodiment, the blood factor coagulation pathway is differentially expressed by a ratio ranging between 4:1-5:1. In one embodiment, the differentially expressed proteomic pathway comprises a lipid metabolism pathway. In one embodiment, the lipid metabolism pathway is differentially expressed by a ratio ranging between 6:1-10:1. In one embodiment, the differentially expressed proteomic pathway comprises an interleukin pathway. In one embodiment, the interleukin pathway is differentially over-expressed by a ratio ranging between 2:1-10:1. In one embodiment, the differentially expressed proteomic pathway comprises a nitric oxide/reactive oxygen species pathway. In one embodiment, the nitric oxide/reactive oxygen species pathway is differentially over-expressed by a ratio ranging between 7:1-10:1.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" as used herein, in the context of any of any assay measurements refers to +/−5% of a given measurement.

The term "substitute for" as used herein, refers to the switching the administration of a first compound or drug to a subject for a second compound or drug to the subject.

The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing (e.g., autoantibody testing) to obtain further information on which to base a diagnosis.

The term "isobaric tag for relative and absolute quantitation (iTRAQ)" refers to a non-gel-based technique used to quantify proteins from different sources in a single experiment. It uses isotope-coded covalent tags, iTRAQ is used in proteomics to study quantitative changes in the proteome. Ross et al., "Multiplexed protein quantitation in *Sacharomyces cerevisiae* using amine-reactive isobaric tagging reagents" *Molecular & Cellular Proteomics* 3: 1154-1169 (2004). iTRAQ is based on the covalent labeling of the N-terminus and side chain amines of peptides from protein digestions with tags of varying mass. For example, two such reagents include, but are not limited to a 4-plex and an 8-plex, which can be used to label all peptides from different samples/treatments. These samples are then pooled and usually fractionated by nano liquid chromatography and analyzed by tandem mass spectrometry (MS/MS). A database search is then performed using the fragmentation data to identify the labeled peptides and hence the corresponding proteins. The fragmentation of the attached tag generates a low molecular mass reporter ion that can be used to relatively quantify the peptides and the proteins from which they originated (e.g., an iTRAQ-peptide analysis spectrum).

The term "infection" as used herein, refers to an invasion of a host organism's body tissues by disease-causing organisms, their multiplication, and the reaction of host tissues to these organisms and the toxins they produce. Infectious diseases, also known as transmissible diseases or communicable diseases, comprise clinically evident illness (i.e., characteristic medical signs and/or symptoms of disease) resulting from the infection, presence and growth of pathogenic biological agents in an individual host organism. For example, infection by a virus may result in acquired community pneumonia that can develop into sepsis.

The term "community-acquired pneumonia (CAP)" as used herein, refers to a type of pneumonia (any of several lung diseases) acquired infectiously from normal social contact (that is, in the community) as opposed to being acquired during hospitalization (hospital-acquired pneumonia). In community-acquired pneumonia, individuals who have not recently been hospitalized develop an infection of the lungs (pneumonia). CAP is a common illness and can affect people of all ages. CAP often causes problems such as difficulty breathing, fever, chest pains, and a cough and sometime develops into sepsis. CAP occurs because the areas of the lung that absorb oxygen (alveoli) from the atmosphere become filled with fluid and cannot work effectively.

The term "liquid chromatography" as used herein, refers a set of laboratory techniques for the separation of mixtures generally using a column (e.g., a liquid chromatography column). A mixture of compounds may be dissolved in a "liquid", which carries the mixture through a column comprising a stationary phase matrix. The various compounds of the mixture travel at different speeds, causing them to separate.

The term "mass spectrometer" as used herein, refers to a mass spectrometer comprising three components such as an ion source, a mass analyzer, and a detector. The ionizer converts a portion of the sample into ions. There is a wide variety of ionization techniques, depending on the phase (solid, liquid, gas) of the sample and the efficiency of various ionization mechanisms for the unknown species. An extraction system removes ions from the sample, which are then trajected through the mass analyzer and onto the detector. The differences in masses of the fragments allows the mass analyzer to sort the ions by their mass-to-charge ratio. The detector measures the value of an indicator quantity and thus provides data for calculating the abundances of each ion present. Some detectors also give spatial information, e.g., a multichannel plate.

The term "tandem mass spectrometer" as used herein, refers to a type of mass spectrometer that is capable of multiple rounds of mass spectrometry, usually separated by some form of molecule fragmentation. For example, one mass analyzer can isolate one peptide from many entering a mass spectrometer. A second mass analyzer then stabilizes the peptide ions while they collide with a gas, causing them to fragment by collision-induced dissociation (CID). A third mass analyzer then sorts the fragments produced from the peptides. Tandem MS can also be done in a single mass analyzer over time, as in a quadrapole ion trap. There are various methods for fragmenting molecules for tandem MS, including collision-induced dissociation (CID), electron capture dissociation (ECD), electron transfer dissociation (ETD), infrared multiphoton dissociation (IRMPD), blackbody infrared radiative dissociation (BIRD), electron-detachment dissociation (EDD) and surface-induced dissociation (SID). An important application using tandem mass spectrometry is in protein identification.

The term "proteomics" as used herein, refers to a large-scale study of proteins, particularly their structures and functions. A proteome may comprise an entire set of proteins produced or modified by an organism or system within that organism. Such organismic systems may comprise specific protein pathways whose participating proteins/peptides are co-regulated. While proteomics generally refers to the large-scale experimental analysis of proteins, it is often specifically used in support of protein purification and mass spectrometry analysis.

The term "proteomic pathway expression profile" as used herein, refers to an analysis of protein expression on a large scale. Proteomic expression analysis helps identify proteins that are differentially expressed in different biological samples-such as diseased vs. healthy tissue, or tissue from a young patient vs. an elderly patient. If a protein is found only in a tissue sample from an elderly patient then it can be a useful drug target or diagnostic marker. Proteins with same or similar expression profiles may also be functionally related. There are technologies such as 2D-PAGE and mass spectrometry that are used in expression proteomics. Two or more different proteomic pathway expression profiles may be compared for differential protein pathway expression. For example, a simple ratio calculation of the processed data from an iTRAQ analysis can determine whether one protein is over/under-expressed. In most cases herein, a ratio is determined between a sepsis proteomic pathway expression profile (e.g., where the biological sample is derived from a subject suspected of having an infection) and a control proteomic pathway expression profile (e.g., where the biological sample is derived from a subject that is not suspected of having a medical condition).

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc) to a binding partner under conditions such that the binding partner becomes unresponsive to its natural ligands. Inhibitory compounds may include, but are not limited to, small organic molecules, antibodies, and proteins/peptides.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60/a, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchioalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis). cDNA (in solution or bound to a solid support) and the like.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1A-D illustrates one embodiment for a parallel blood plasma workflow schematic using four iTRAQ reporter ions in Multiple Affinity Removal System (MARS) columns in preparation for nanoscale liquid chromatography coupled to tandem mass spectrometry (Nano-LC-MS/MS) analysis. Exemplary iTRAQ Reporter Ions-Column A: iTRAQ_14 ($I_{114}$); Column B: iTRAQ_115 ($I_{115}$); Column C: iTRAQ_116 ($I_{116}$); Column D: iTRAQ_117 ($I_{117}$).

FIG. 2A: Solid Line: Accumulation of identified proteins (773) of which 726 proteins were identified. Bars:

FIG. 2B: Data demonstrating the relative stability of spectral counts over the course of the ten Nano-LC-MS/MS experiments.

FIG. 3 presents Venn diagrams depicting the differences and overlap between the various subject populations.

FIG. 10A: A MARS-depleted human plasma chromatogram.

FIG. 10B: A tandem MARS-depleted human plasma chromatogram.

FIG. 14A: Conventional MS spectra.

FIG. 14B: CID MS/MS spectra and analysis.

FIG. 14C; HCD MS/MS spectra and analysis.

FIG. 14D: Control spectra showing the reporter ion ratios ($I_{114}:I_{115}:I_{116}:I_{117}$=1:3.44:2.62:1.45).

FIG. 16A: Tissue necrosis factor (TNF)

FIG. 16B: Interleukin 6 (IL-6)

FIG. 16C: Interleukin 10 (IL-10).

FIG. 17A: A CID spectra and analysis.

FIG. 17B: A HCD spectra and analysis.

FIG. 18A: A CID spectra and analysis.

FIG. 18B: A HCD spectra and analysis.

FIG. 19A: Peptide ratio distribution.

FIG. 19B: Protein ratio distribution.

FIG. 20A: A CID spectra and analysis.

FIG. 20B: A HCD spectra and analysis.

FIG. 21 A-B presents representative Nano-LC-MS/MS data for a peptide fragment (D(iTRAQ)LATVYVDVLK(iTRAQ)+2H)$^{2+}$ (SEQ ID NO: 1) of apolipoprotein A-1. Spectral Counts=1734; Unique peptides=24.

FIG. 22A: LC chromatograms for individual SCX fractions analyzed in triplicate.

FIG. 22B: Exemplary mass spectra of peptides eluted from SCX fraction 7 ($t_r$=57.20 min with m/z 748.8046);

FIG. 22C: Exemplary mass spectra of peptides eluted from SCX fraction 6 ($t_r$=37.26 min with m/z 742.9010).

FIG. 22D: Exemplary CID MS/MS of peptides eluted from SCX fraction 7.

FIG. 22E: Exemplary CID MS/MS of peptides eluted from SCX fraction 6.

FIG. 22F: Exemplary HCD MS/MS of peptides eluted from SCX fraction 7 (inset: low m/z region).

FIG. 22G: Exemplary HCD MS/MS of peptides eluted from SCX fraction 6 (inset: low m/z region).

FIG. 24A: C-reactive protein,

FIG. 24B: Fibrinogen alpha chain.

FIG. 24C: Apolipoprotein C111.

DETAILED DESCRIPTION

Figure 2A:
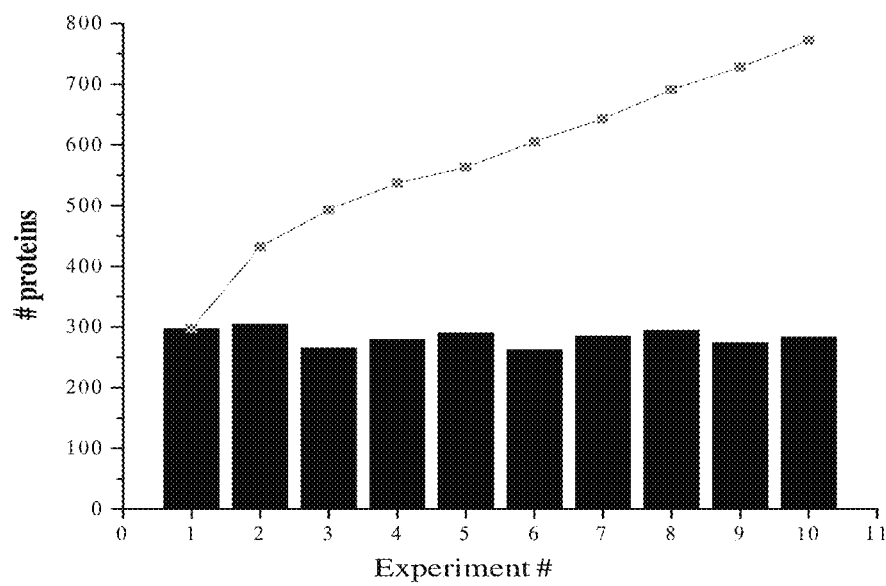
FIG. 2A-B shows exemplary data over the course often (10) Nano-LC-MS/MS experiments.
Figure 2B:
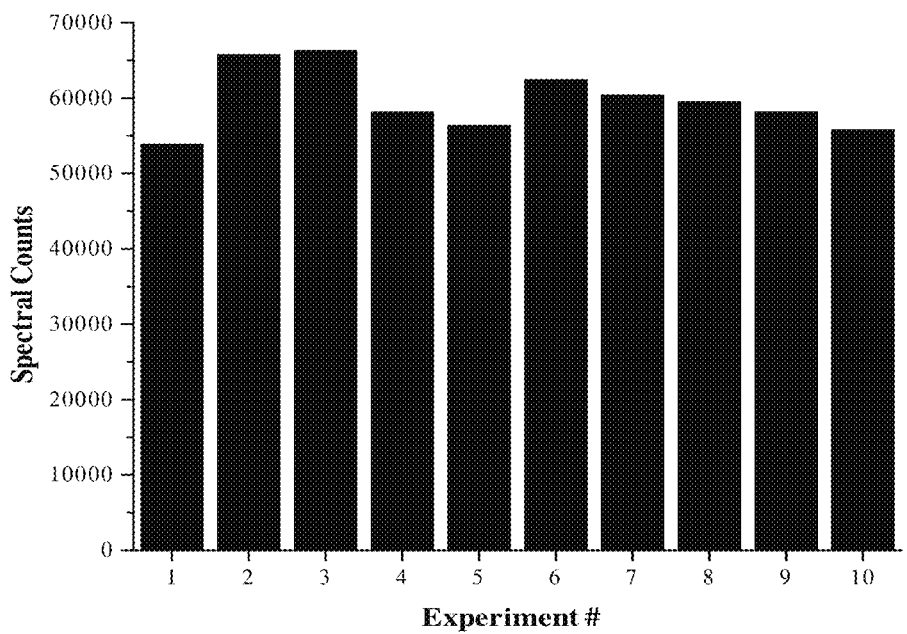
Figure 4:
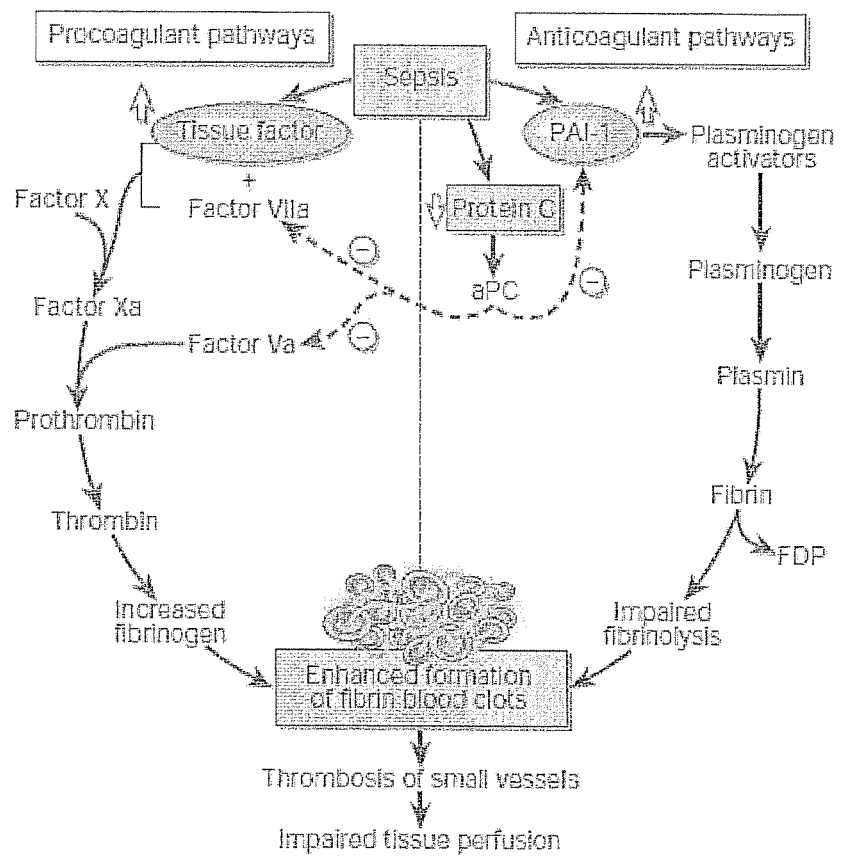
FIG. 4 presents a present understanding of a physiological process of thrombosis initiated by sepsis.
Figure 5:
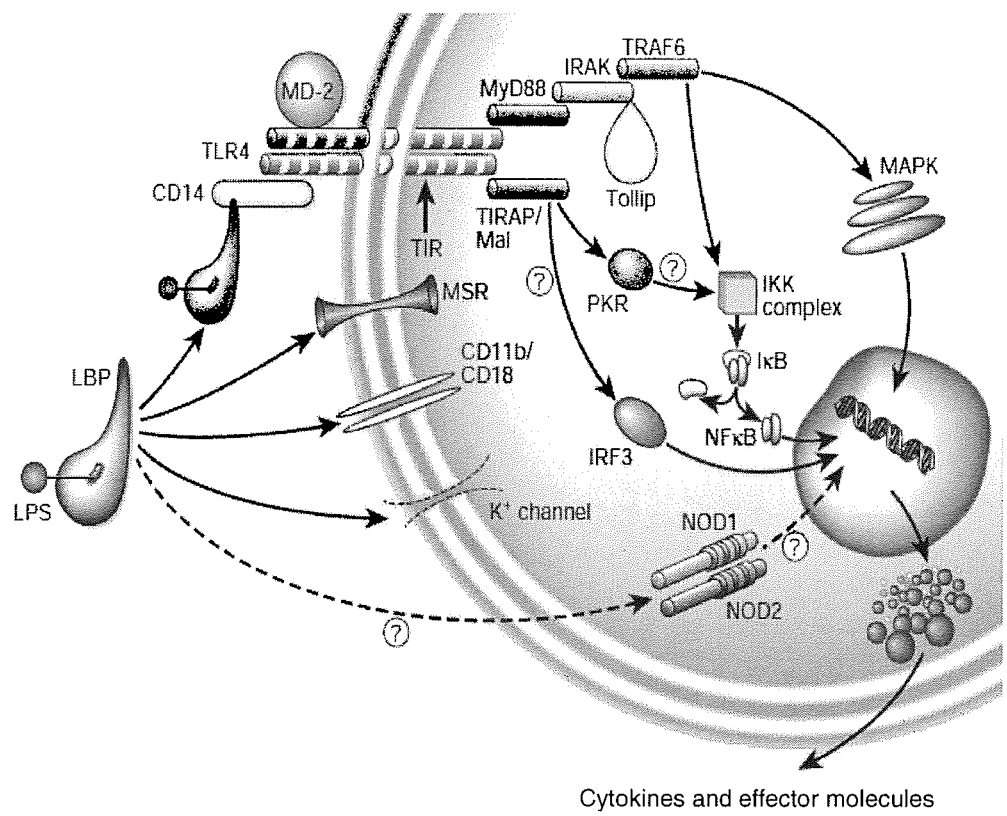
FIG. 5 presents a present understanding of a cytokine regulation pathway.
Figure 6:
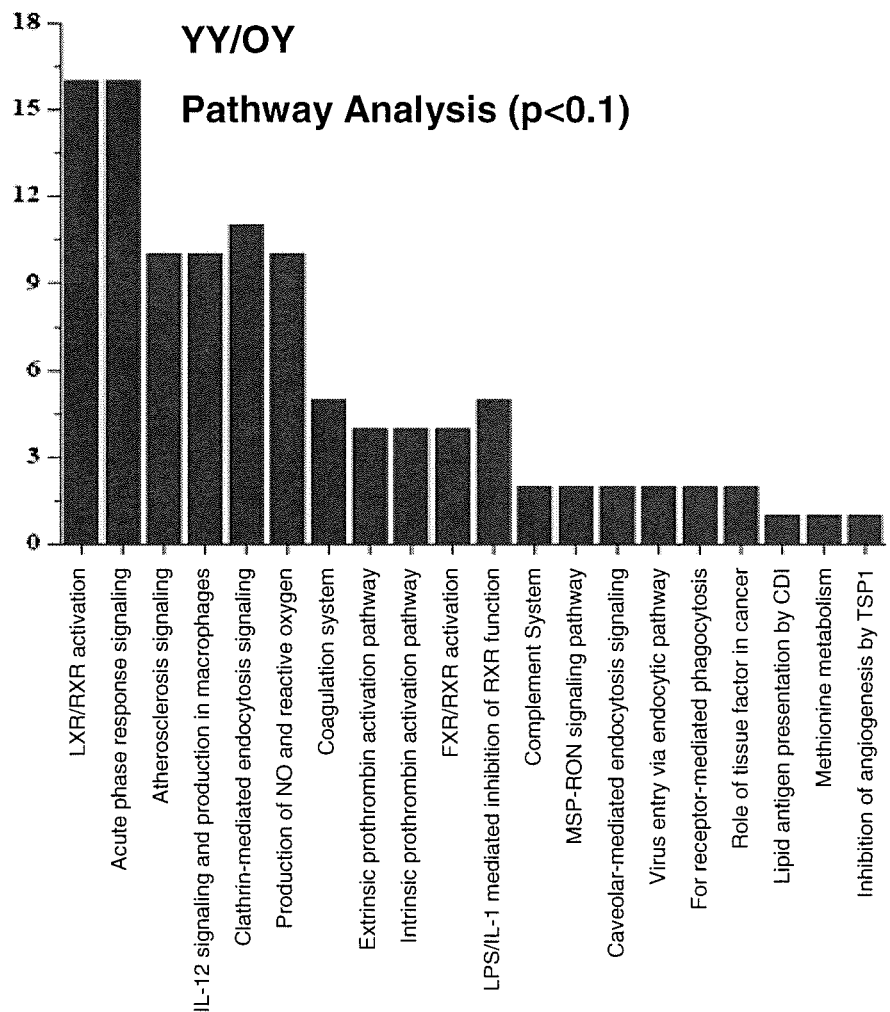
FIG. 6 presents exemplary data showing differentially expressed pathways between the YY/OY subject populations.
Figure 7:
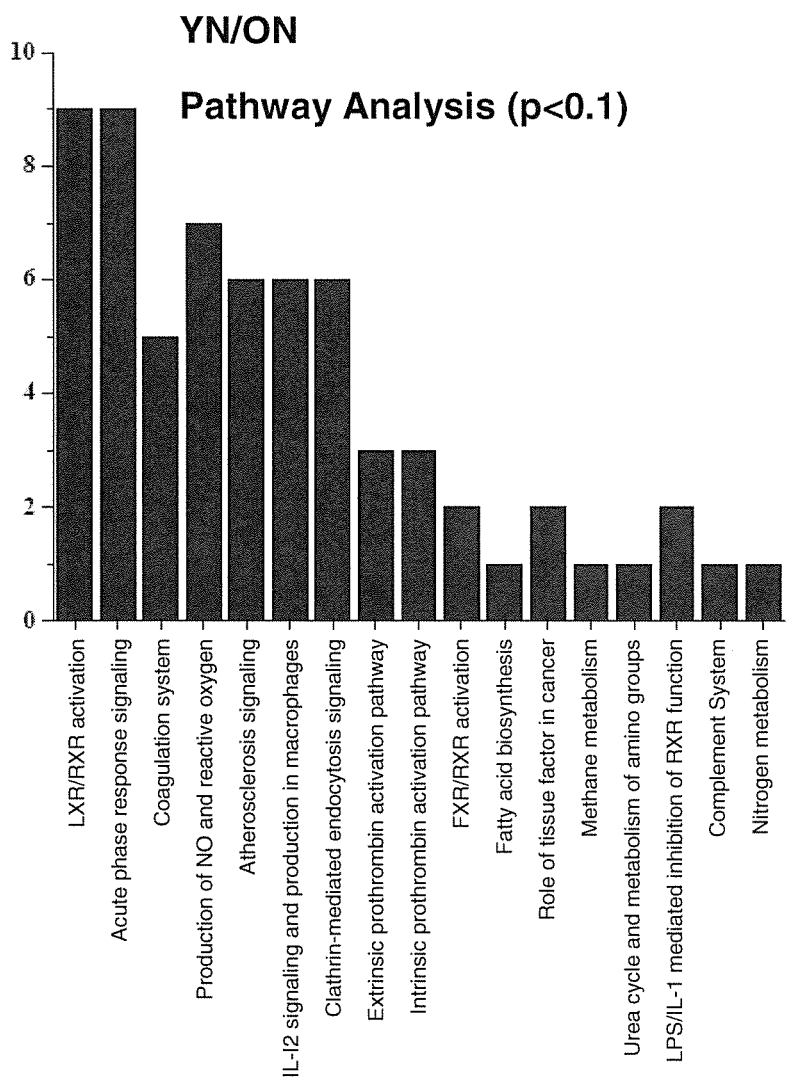
FIG. 7 presents exemplary data showing differentially expressed pathways between the YN/ON subject populations.
Figure 8:
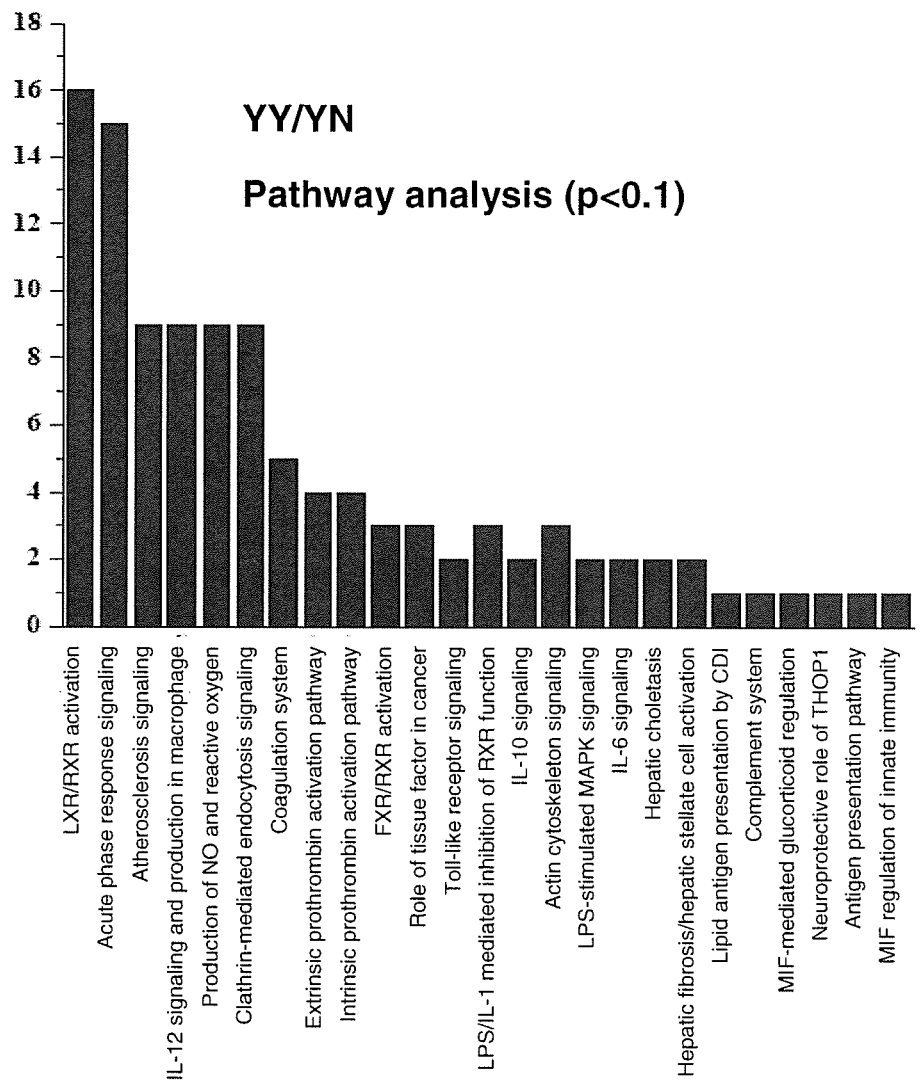
FIG. 8 presents exemplary data showing differentially expressed pathways between the YY/YN subject populations.
Figure 9:
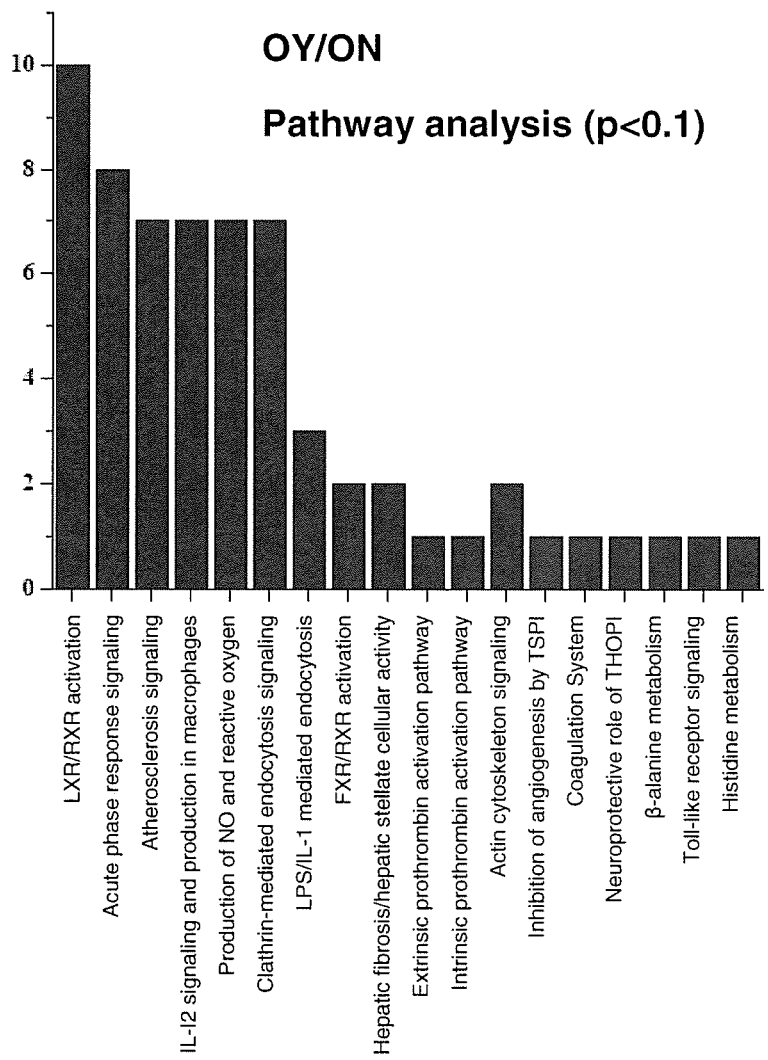
FIG. 9 presents exemplary data showing differentially expressed pathways between the OY/ON subject populations.

The present invention is related to the field of sepsis. In particular, the invention identifies differences in global protein expression that are either age-related and/or outcome-related. These differences represent biomarkers to guide risk potential, therapy, monitoring and diagnosis.

In one embodiment, the present invention contemplates a method for producing a sepsis proteomic expression profile comprising MARS-sample depletion, iTRAQ reporter ions, SCX protein fractionation and nano-LC-MS/MS. In one embodiment, the method generates highly reproducible data with 90% of RSD smaller than 0.25.

I. Sepsis

Sepsis is believed to be a systematic inflammatory state triggered by infection. Other conditions including, but not limited to, multiple organ failure and hypoperfusion (e.g., hypotension, decreased urine output) in combination with sepsis can result in severe sepsis. Dellinger et al., "Surviving Sepsis Campaign: International Guidelines for Management of Severe Sepsis and Septic Shock: 2012" *Critical Care Medicine* 41:580-637 (2013). One of the leading causes of sepsis is community-acquired pneumonia (CAP). Kale et al., "The effects of age on inflammatory and coagulation-fibrinolysis response in patients hospitalized for pneumonia" *PLoS ONE* 5:e13852 (2010); Dremsizov et al., "Severe sepsis in community-acquired pneumonia" *Chest* 129:968-978 (2006); and Beutz et al., "Community-acquired pneumonia and sepsis" *Clinics In Chest Medicine* 26:19-28 (2005). The presence and severity of organ failure is one of the most important determinants of mortality following sepsis. Severe sepsis affects ~750,000 persons annually in the United States and is one of the most common causes of death in intensive care units. Vincent et al., "SOFA so good for predicting long-term outcomes" *Resuscitation* 83:537-538 ((2012)); Carrigan et al., "Toward resolving the challenges of sepsis diagnosis" *Clinical Chemistry* 50:1301-1314 ((2004); Davis, B. H., "Improved diagnostic approaches to infection/sepsis detection" *Expert Review of Molecular Diagnostics* 5:193-207 (2005); Levy et al., "2001 SCCM/ESICM/ACCP/ATS/SIS International Sepsis Definitions Conference" *Critical Care Medicine* 31:1250-1256 (2003); Balk, R. A., "Severe sepsis and septic shock: definitions, epidemiology, and clinical manifestations" *Critical Care Clinics* 16:179-192 (2000); Martin et al., "The epidemiology of sepsis in the United States from 1979 through 2000" *New England Journal of Medicine* 348:1546-1554 (2003); Cohen, J., "The immunopathogenesis of sepsis" *Nature* 420:885-891 (2002).

It has been reported that the incidence of severe sepsis and mortality rate increases sharply after the age of 65. Angus et al., "Epidemiology of severe sepsis in the United States: Analysis of incidence, outcome, and associated costs of care" *Critical Care Medicine* 29:1303-1310 (2001); and Martin et al., "The effect of age on the development and outcome of adult sepsis" *Critical Care Medicine* 34:15-21 (2006. For example, CAP patients ≥85 years old have a 2.8-fold increased risk of severe sepsis and a 17-fold increased mortality rate compared to patients ≤50 years old. The notable age-related differences in severe sepsis risk may be explained in part by immunosenescence underlying chronic disease. Immunosenesence is manifested in the elderly through decreased numbers of T cells, impaired B-cell function, increased apoptosis of neutrophils, and reduced bactericidal response of macrophages. Opal et al., "The immunopathogenesis of sepsis in elderly patients" *Clinical Infectious Diseases* 41:S504-5512 (2005); and Wick et al., "The aging immune system: primary and secondary alterations of immune reactivity in the elderly" *Experimental Gerontology* 32:401-413 (1997).

Most of the above studies that examined age-related differences in immune response using animal models and humans have largely focused on either the adaptive immune response or select pathways (inflammatory, coagulation, and fibrinolysis markers) in the innate immune response. A comprehensive assessment of differences in the immune response has not been conducted. Trials testing immunomodulating therapies for sepsis in broad populations have failed to consistently improve outcomes of sepsis patients. Hotchkiss et al., "The pathophysiology and treatment of sepsis" *New England Journal of Medicine* 348:138-150 (2003). An alternative approach is to personalize sepsis therapies based on host characteristics, such as age. To further the development of such a personalized approach, a better understanding of the differences in immune response due to age is necessary.

In sepsis, blood pressure generally drops resulting in shock. Major organs and body systems, including the kidneys, liver, lungs, and central nervous system, stop working properly because of poor blood flow. A change in mental status and very fast breathing may be the earliest signs of sepsis. In general, symptoms of sepsis can include, but are not limited to, chills, confusion or delirium, fever or low body temperature (hypothermia), light-headedness due to low blood pressure, rapid heartbeat, shaking, skin rash, warm skin, bruising and/or bleeding.

II. Nanoscale Liquid Chromatography Coupled to Tandem Mass Spectrometry

Nanoscale liquid chromatography coupled to tandem mass spectrometry (nano LC-MS/MS) has been widely implemented in the field of proteomics. In fact, its sensitivity has advantages over conventional LC-MS/MS that allow the analysis of peptide mixtures in sample-limited situations (e.g., proteolytically digested proteins isolated by two-dimensional gel electrophoresis). Technical challenges, associated with low flow rates of the chromatographic separation, make this technology still difficult to run routinely. Some a nano LC-MS/MS setups allow several weeks of continuous operation for the analysis of peptides derived by enzymatic digestion of either purified proteins or moderately complex protein mixtures. Gaspari et al., "Nano LC-MS/MS: a robust setup for proteomic analysis" *Methods Mol Biol.* 790:115-126 (2011).

A preparation pathway for Nano-LC-MS/MS is outlined. See, FIG. 1A-D. In general, an experimental design was followed that identified the patient's age (e.g., young (Y), old (O)) in conjunction with the presence or absence of sepsis (e.g., sepsis (Y), no sepsis (N). One exemplary experimental design is outlined. See, Table 1.

TABLE 1

Experimental design and iTRAQ quantitation channel assignment

| | reporter ion__114 | reporter ion__115 | reporter ion__116 | reporter ion__117 |
|---|---|---|---|---|
| 1st Experiment | YY[a] | YN[b] | OY[c] | ON[d] |
| 2nd Experiment | YY[a] | YN[b] | OY[c] | ON[d] |
| 3rd Experiment | YY[a] | YN[b] | OY[c] | ON[d] |
| 4th Experiment | YY[a] | YN[b] | OY[c] | ON[d] |
| 5th Experiment | YN[b] | OY[c] | ON[d] | YY[a] |
| 6th Experiment | YN[b] | OY[c] | ON[d] | YY[a] |
| 7th Experiment | YN[b] | OY[c] | ON[d] | YY[a] |
| 8th Experiment | OY[c] | ON[d] | YY[a] | YN[b] |
| 9th Experiment | OY[c] | ON[d] | YY[a] | YN[b] |
| 10th Experiment | OY[c] | ON[d] | YY[a] | YN[b] |

[a] subjects who are at the age of 50-65 and with severe sepsis;

[b] subjects who are at the age of 50-65 and without severe sepsis;

[c] subjects who are at the age of 70-85 and with severe sepsis;

[d] subjects who are at the age of 70-85 and without severe sepsis.

One optimized workflow was applied to plasma derived from four groups of sepsis patients. The four groups were: 1) 10 survivors at 60-65 years with severe sepsis, 2) 10 non-survivors at 60-65 years with severe sepsis, 3) 10 survivors >80 years with severe sepsis and 4) 10 non-survivors >80 years with severe sepsis. See, Table 2.

TABLE 2

Subject Profile For Determining Age-Related Outcomes In Sepsis

| Younger Sepsis Patients | | Older Sepsis Patients | |
|---|---|---|---|
| Survivor (10 Subjects) | Death (10 Subjects) | Survivor (10 Subjects) | Death (10 Subjects) |

Samples from the four groups were analyzed with the optimized workflow blindly.

Figure 10A:
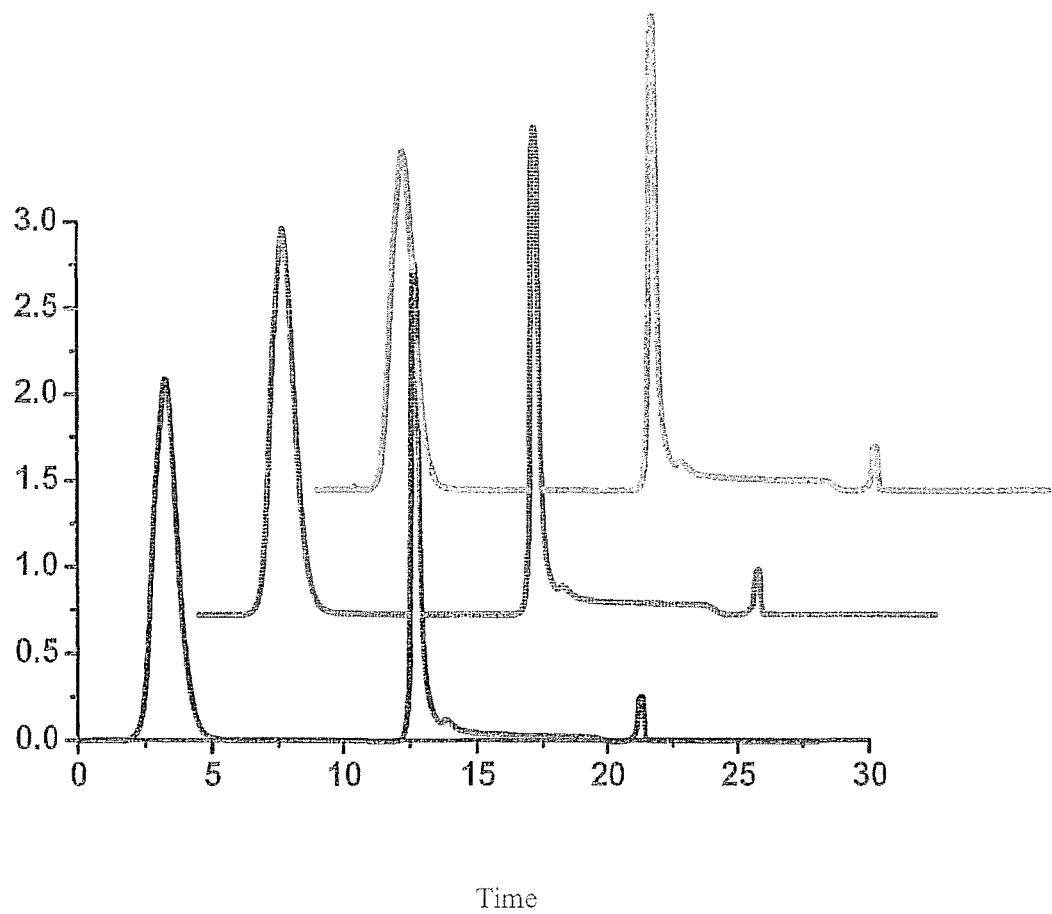
FIG. 10A-B presents exemplary data, in triplicate, showing the reproducibility of Nano-LC-MS/MS.
Figure 10B:
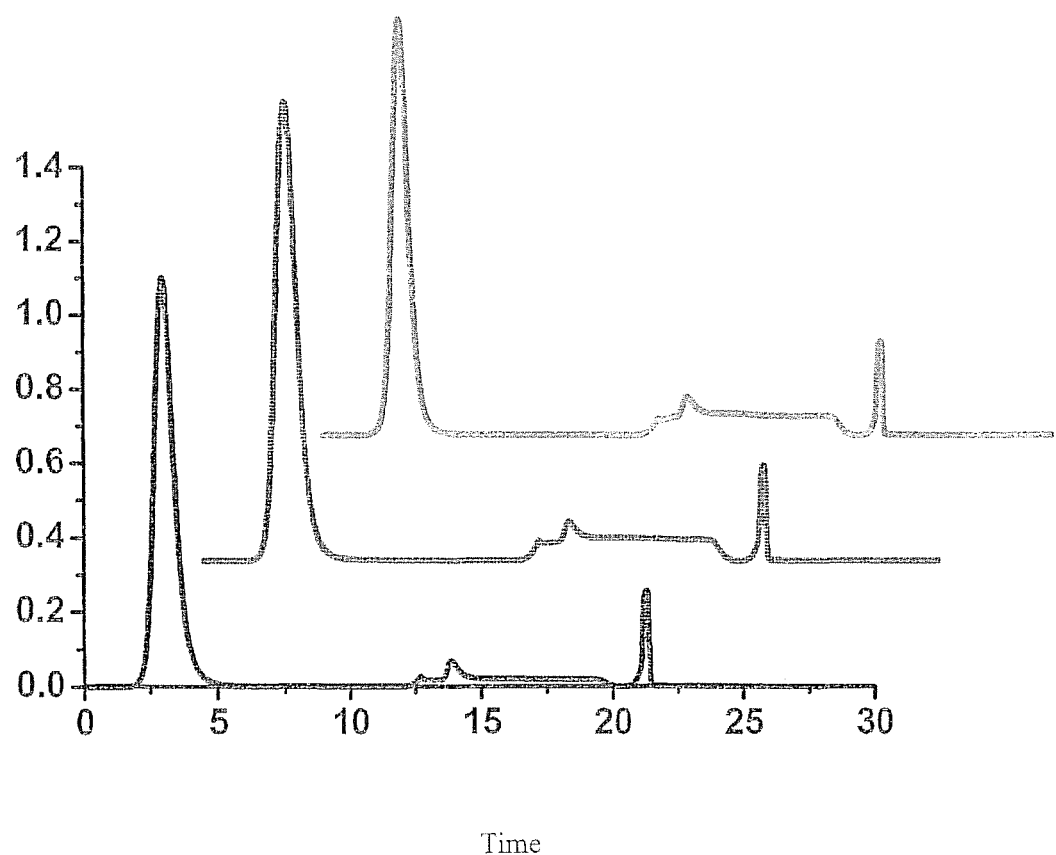
Figure 11:
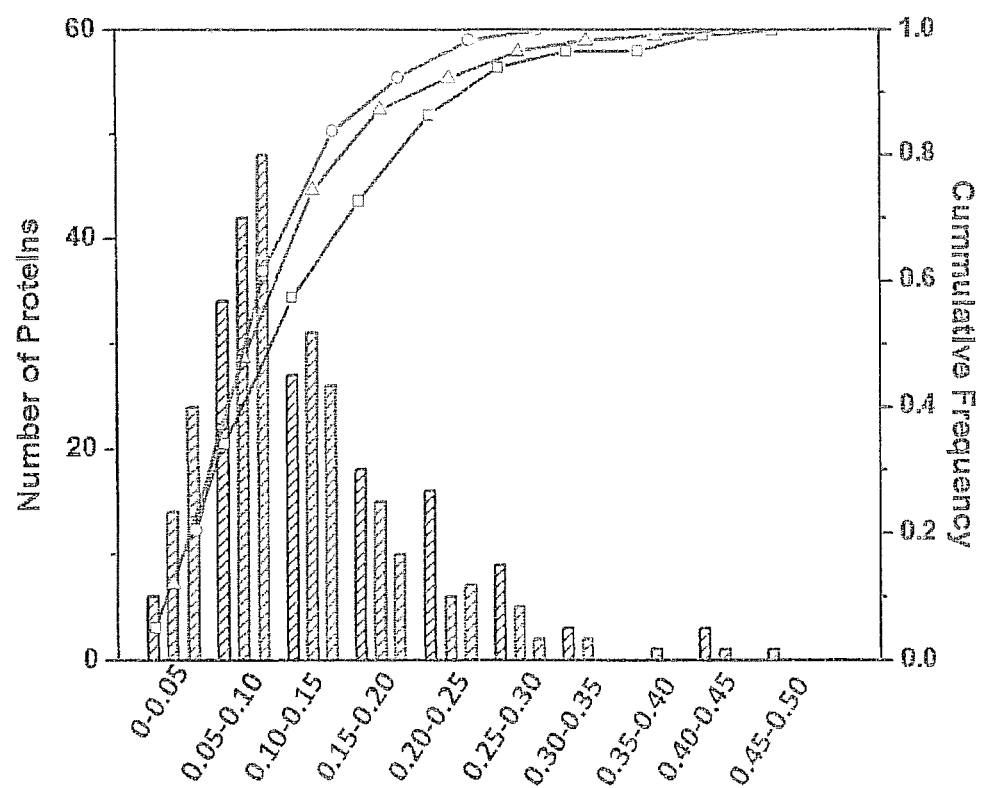
FIG. 11 presents exemplary data showing the reproducibility of the workflow using four plasma samples from CAP patients that were prepared and analyzed with the iTRAQ workflow. Across the triplicate sample sets, 90% of the quantified proteins had a RSD smaller than 0.25. Blue Cross-Hatched Bar: $I_{115}/I_{114}$ protein number, Orange Cross-Hatched Bar: $I_{116}/I_{114}$ protein number, and Green Cross-Hatched Bar: $I_{117}/I_{114}$ protein number. Blue Squares: $I_{115}/I_{114}$ cumulative frequency. Orange Squares: $I_{16}/I_{114}$ cumulative frequency. Green Squares: $I_{117}/I_{114}$ cumulative frequency.
Figure 12:
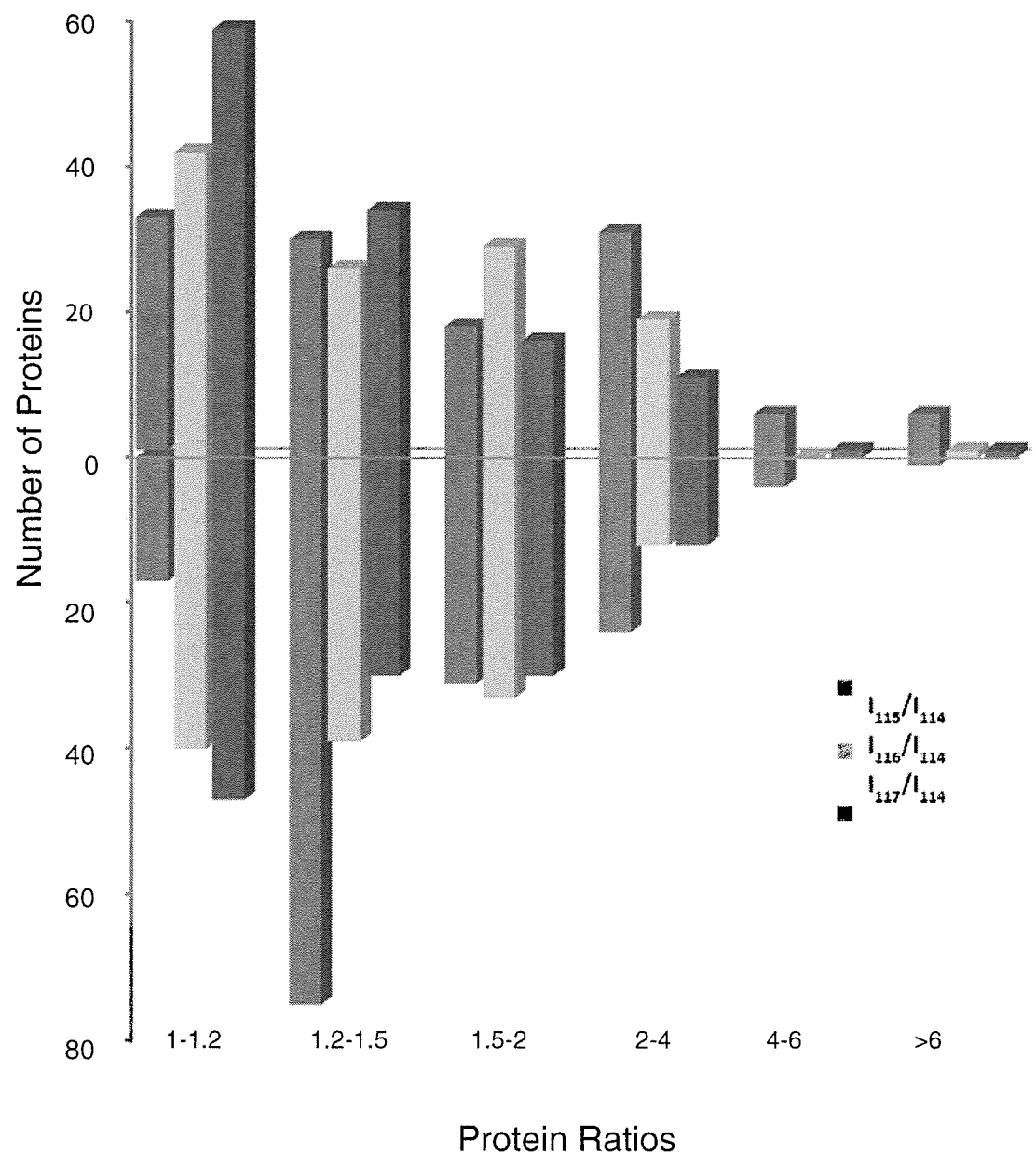
FIG. 12 presents exemplary data showing a distribution of protein ratios across four plasma samples as described in FIG. 11. Blue Bars: $I_{115}/I_{114}$; Green Bars: $I_{116}/I_{114}$; Red Bars: $I_{117}/I_{114}$.
Figure 13:
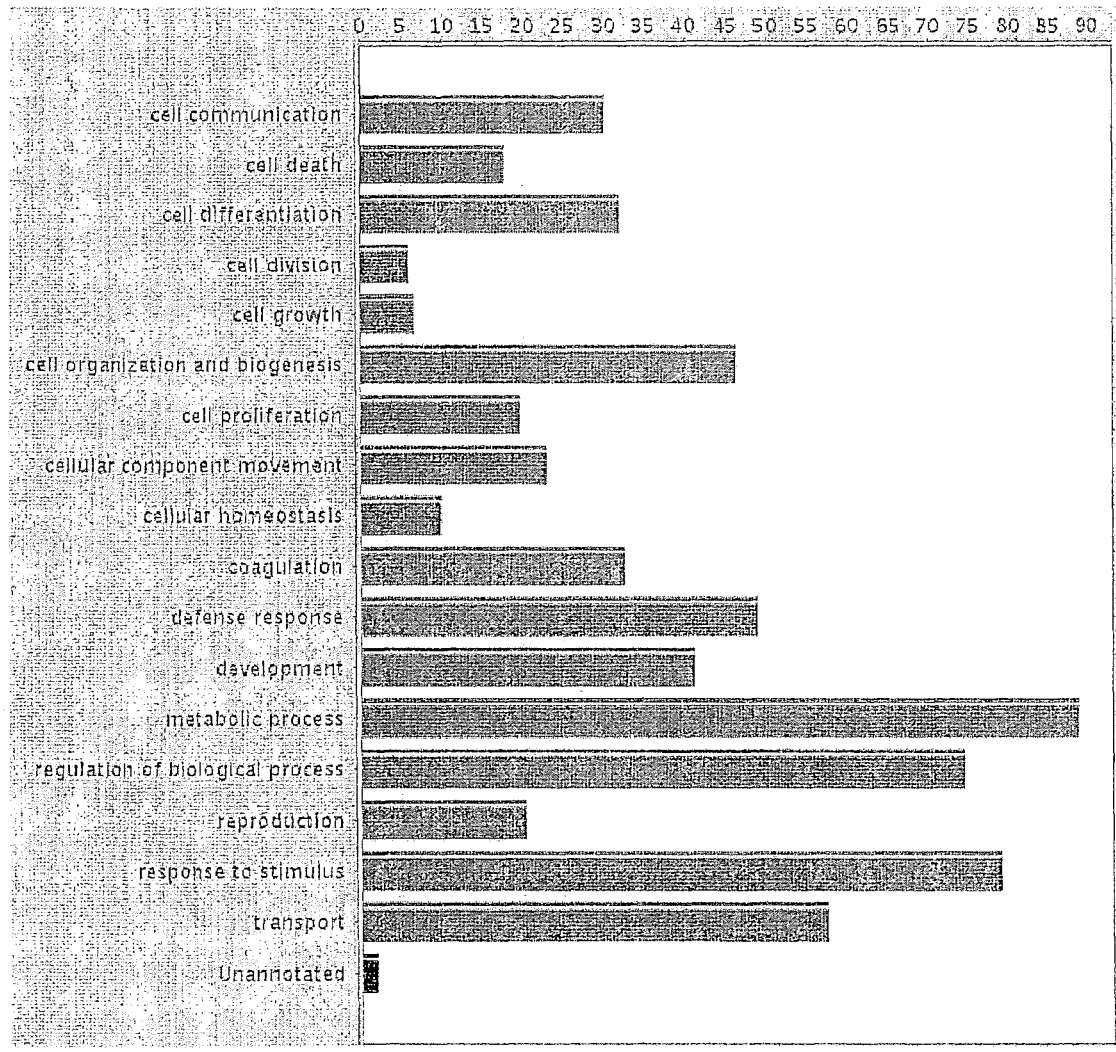
FIG. 13 presents the identification of over-expressed protein pathways based upon the quantified protein ratios.
Figure 14A:
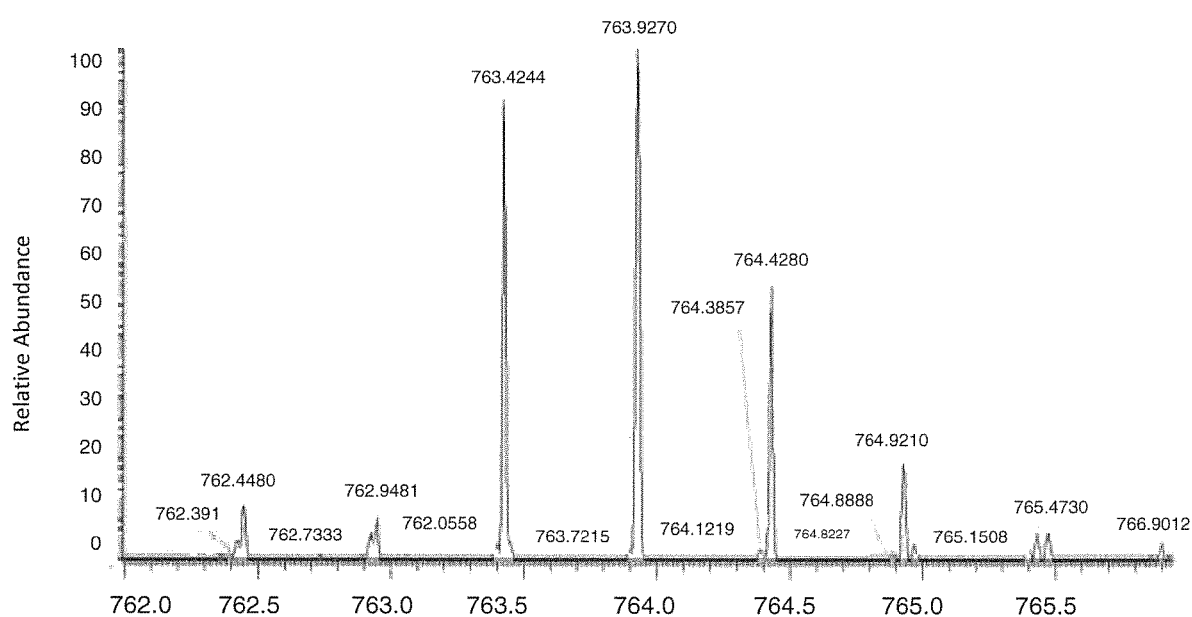
FIG. 14A-D presents exemplary MS/MS spectrum data of the fragmentation pattern of the peptide D(iTRAQ)LATVYVDVLK(iTRAQ) (z=+2, m/z+763.4244) (SEQ ID NO: 1) from apoliprotein A-1 showing how protein ratios were obtained based on the corresponding peptide ratios as the same peptides from four different samples cannot be differentiated on MS level. Consequently, peptide identification and peptide quantitation were based on MS/MS spectrum obtained from CID and HCD fragmentation, respectively. Protein identification: CID MS/MS. Protein Quantitation: HCD MS/MS.
Figure 14B:
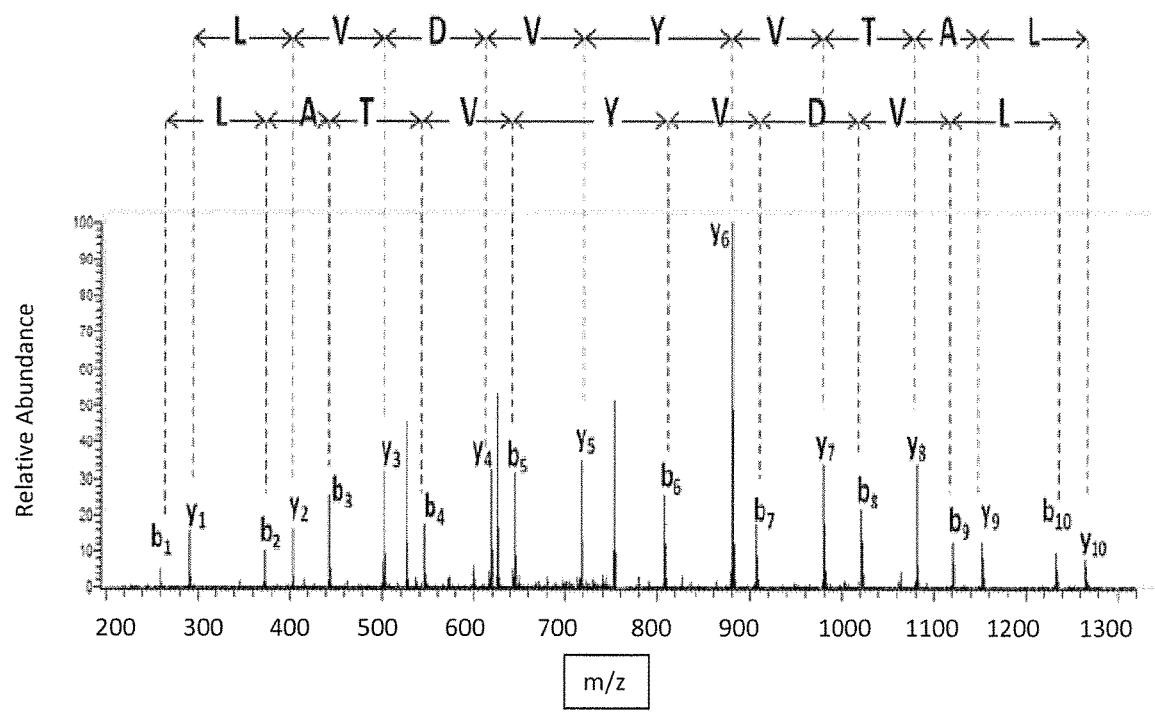
Figure 14C:
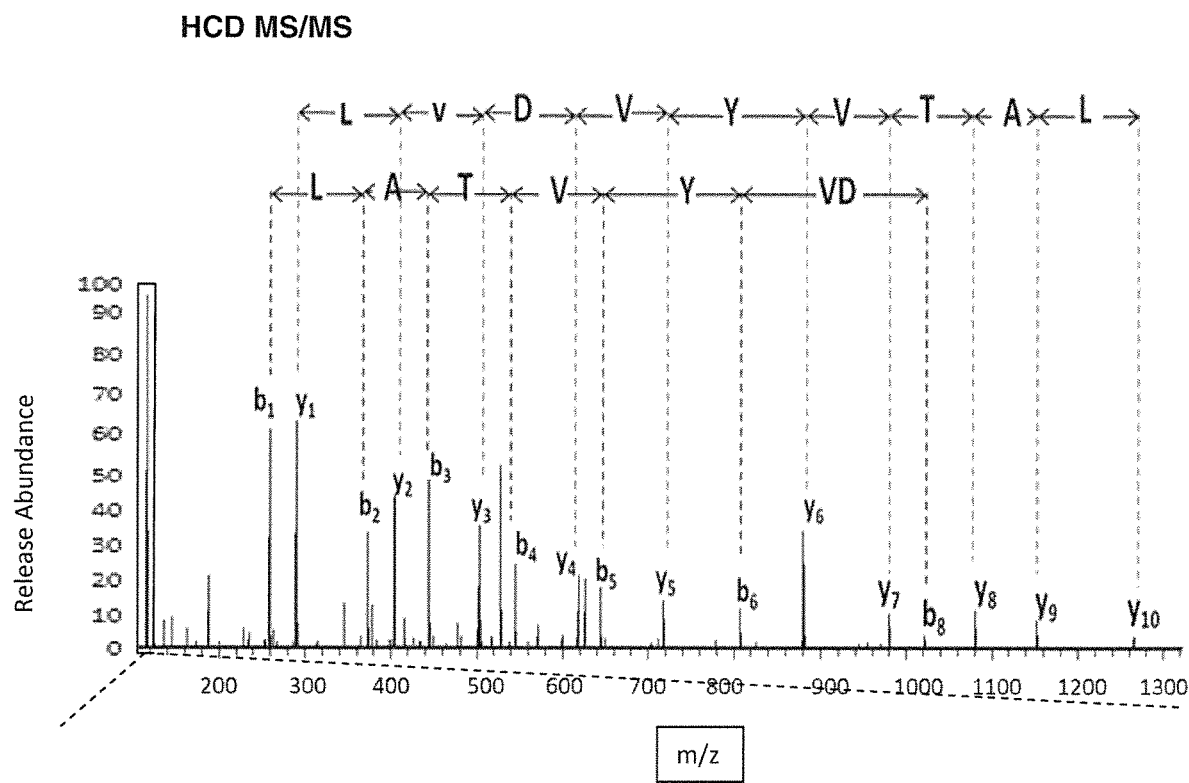
Figure 14D:
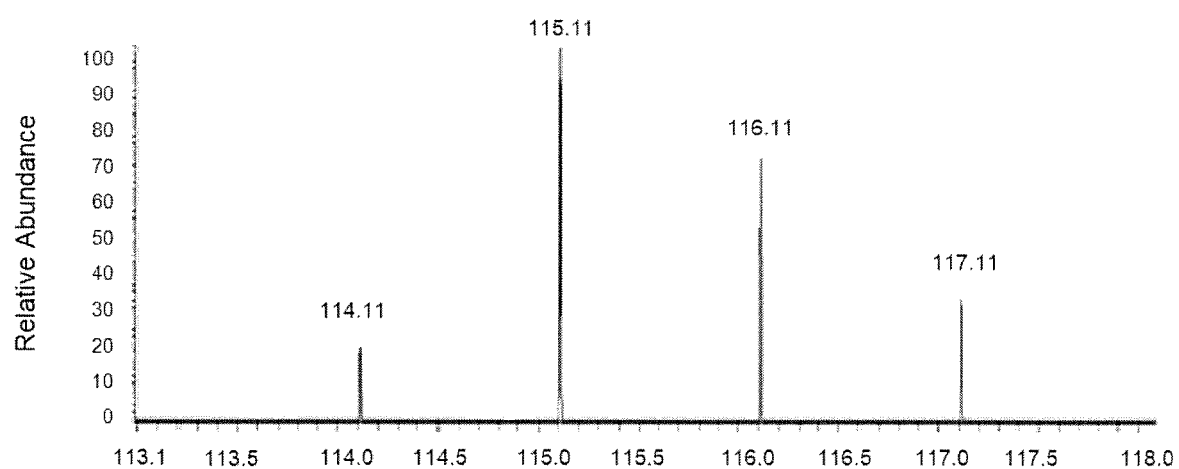
Figure 15A:
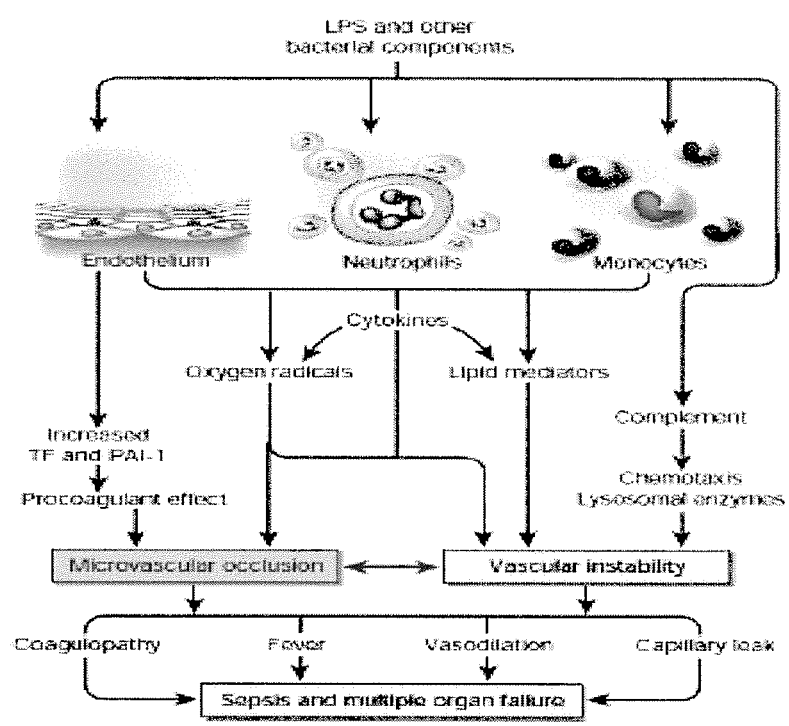
FIG. 15A presents conventional understanding of a sepsis pathway. Cohen J., *Nature* 420:885-891 (2002).
Figure 15B:
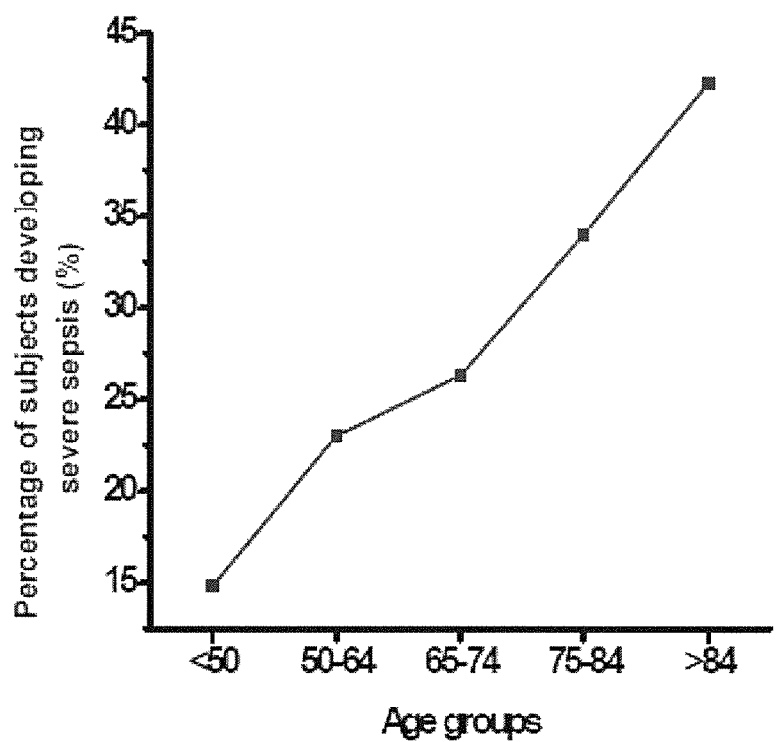
FIG. 15B presents a representative distribution of the relationship between age and severe sepsis. Kale et al., PLoS one 5:e13852 (2010).
Figure 16A:
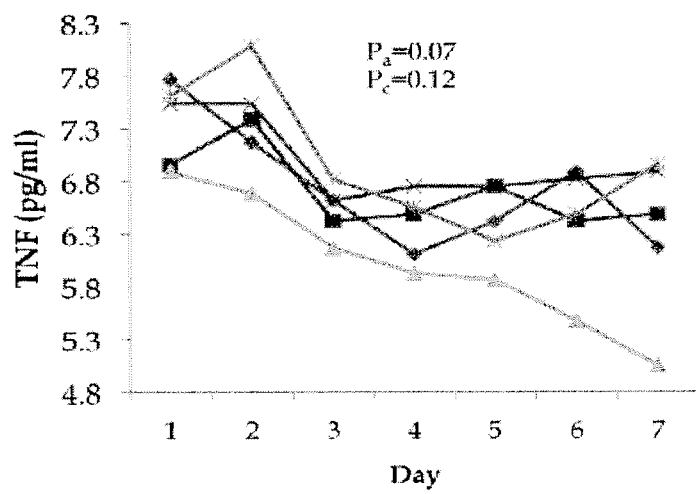
FIG. 16A-C presents representative data showing sepsis-induced cytokine patterns as a function of age. Blue Diamonds: <50 years. Red Squares: 50-64 years. Green Triangles: 65-74 years. Purple Crosses: 75-84 years. Blue Crosses: >85 years.
Figure 16B:
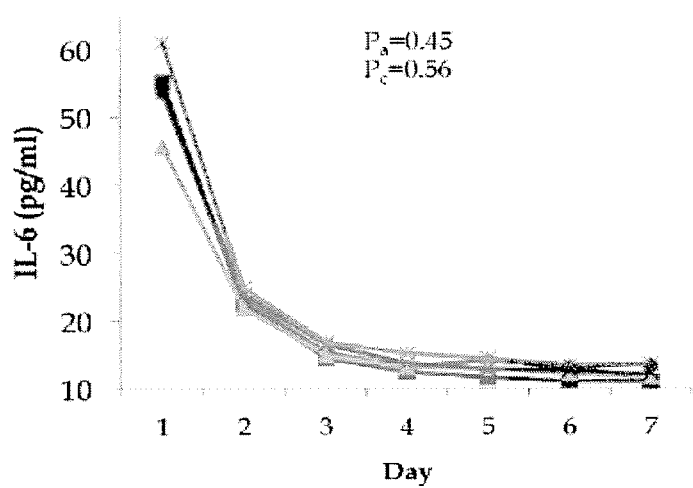
Figure 16C:
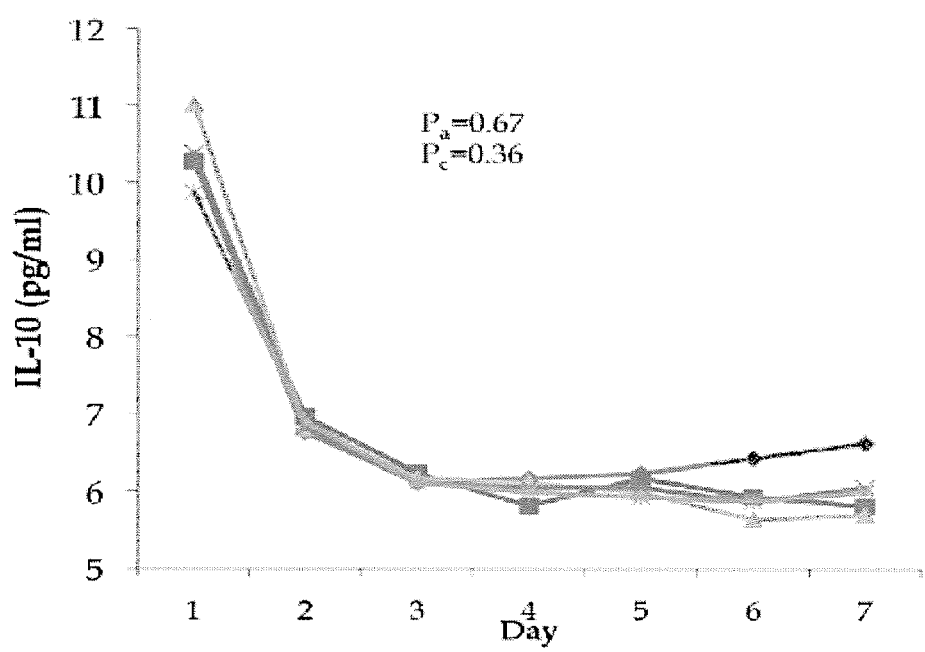
Figure 17A:
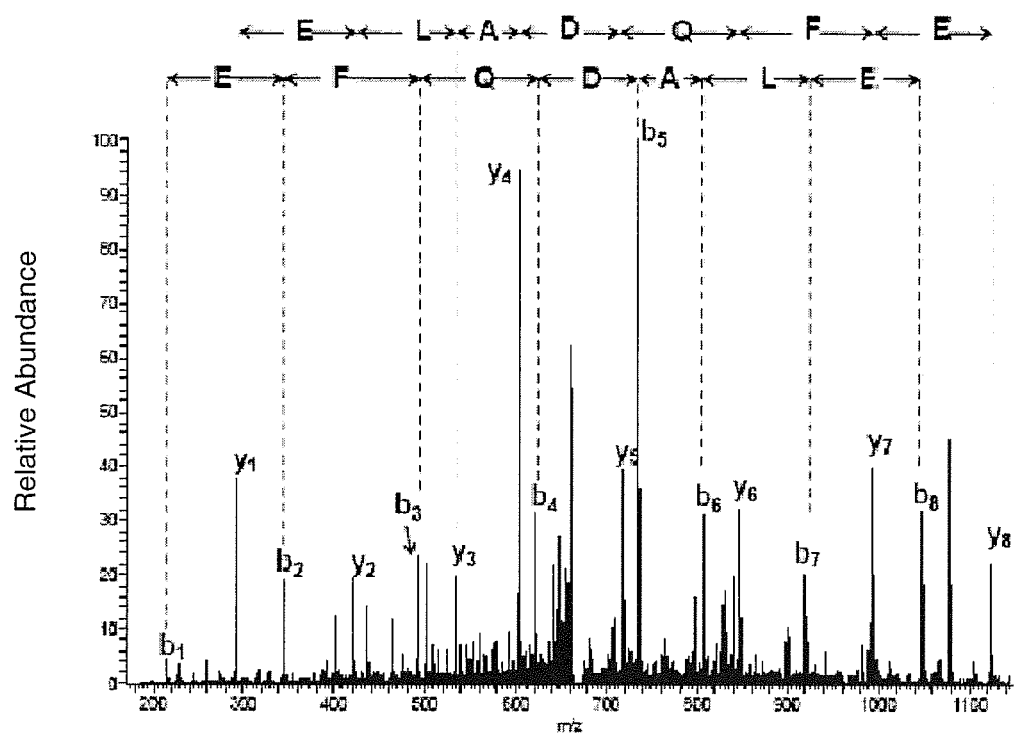
FIG. 17A-B presents representative Nano-LC-MS/MS data for a peptide fragment (A(iTRAQ)EFQDALEK(iTRAQ)+2H)$^{2+}$ (SEQ ID NO: 2) of Complement C4. Spectral Counts=450; Unique peptides=59.
Figure 17B:
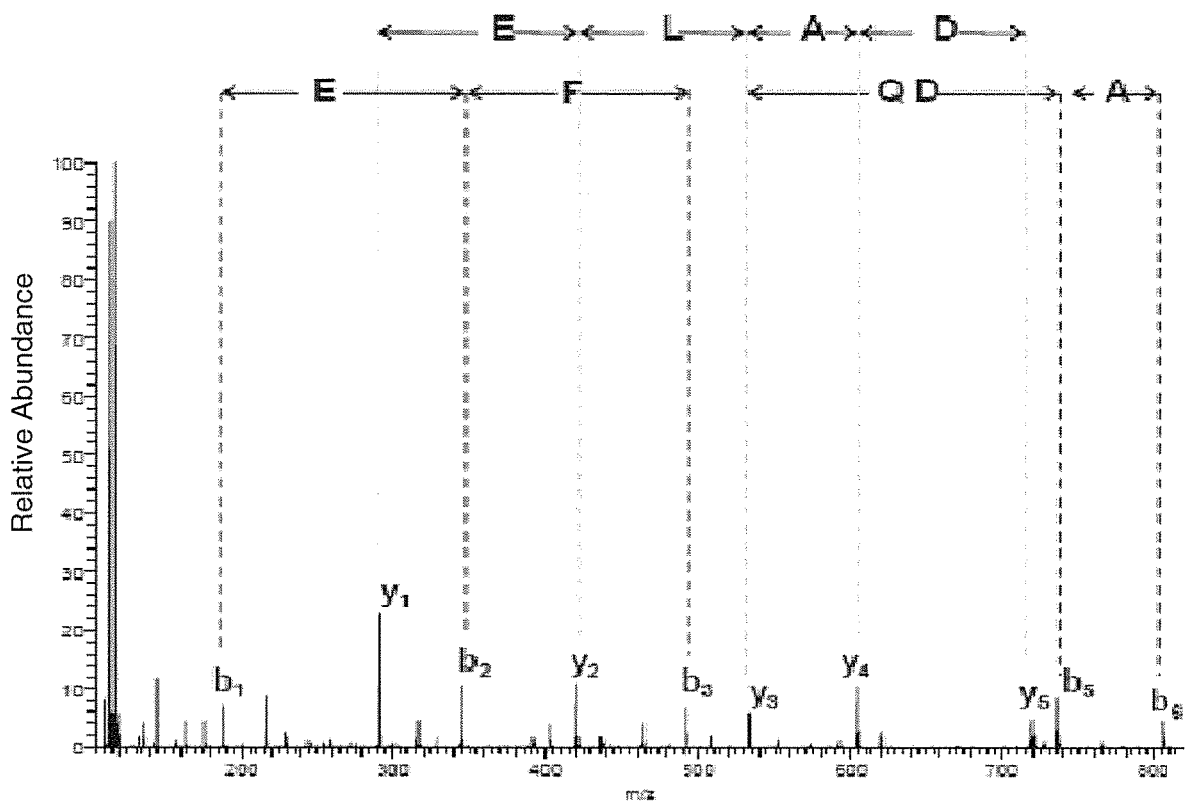
Figure 18A:
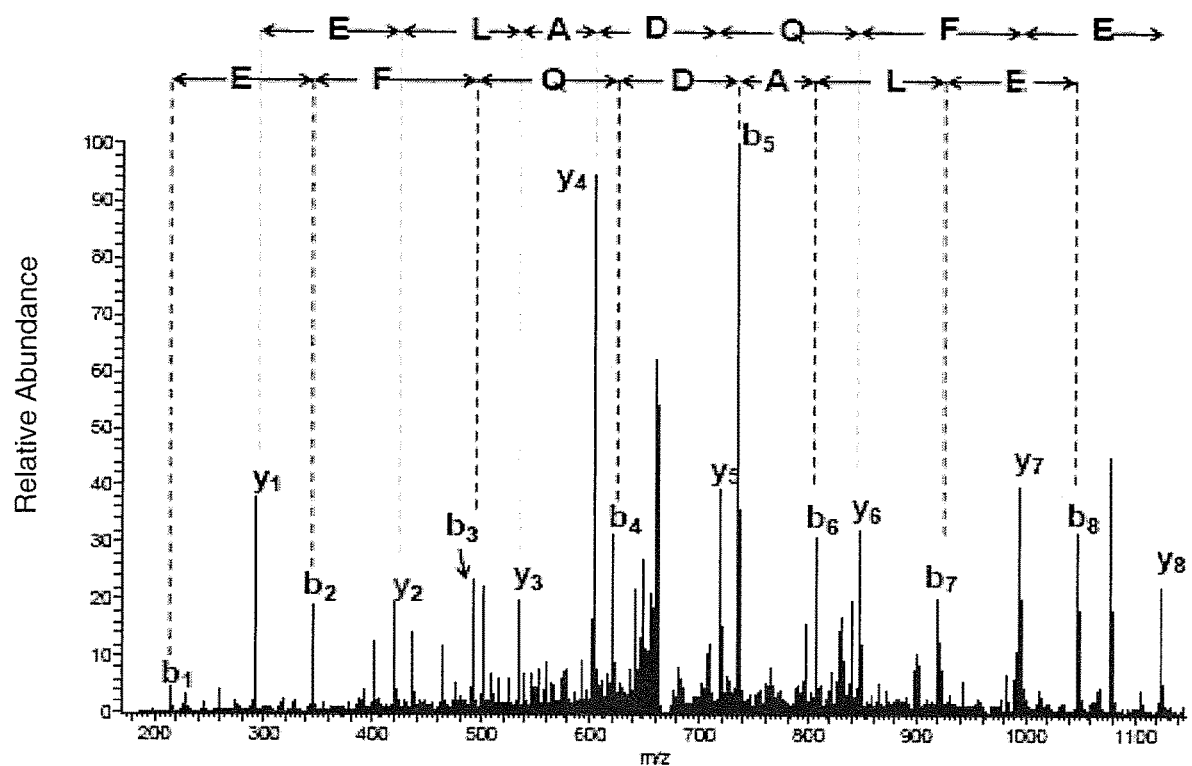
FIG. 18A-B presents representative Nano-LC-MS MS data for a peptide fragment (A(iTRAQ)EFQDALEK(iTRAQ)+2H)$^{2+}$ (SEQ ID NO: 2) of Complement C4. Spectral Count=450; Unique peptides=59, Ratio 117/114=1.14±0.38.
Figure 18B:
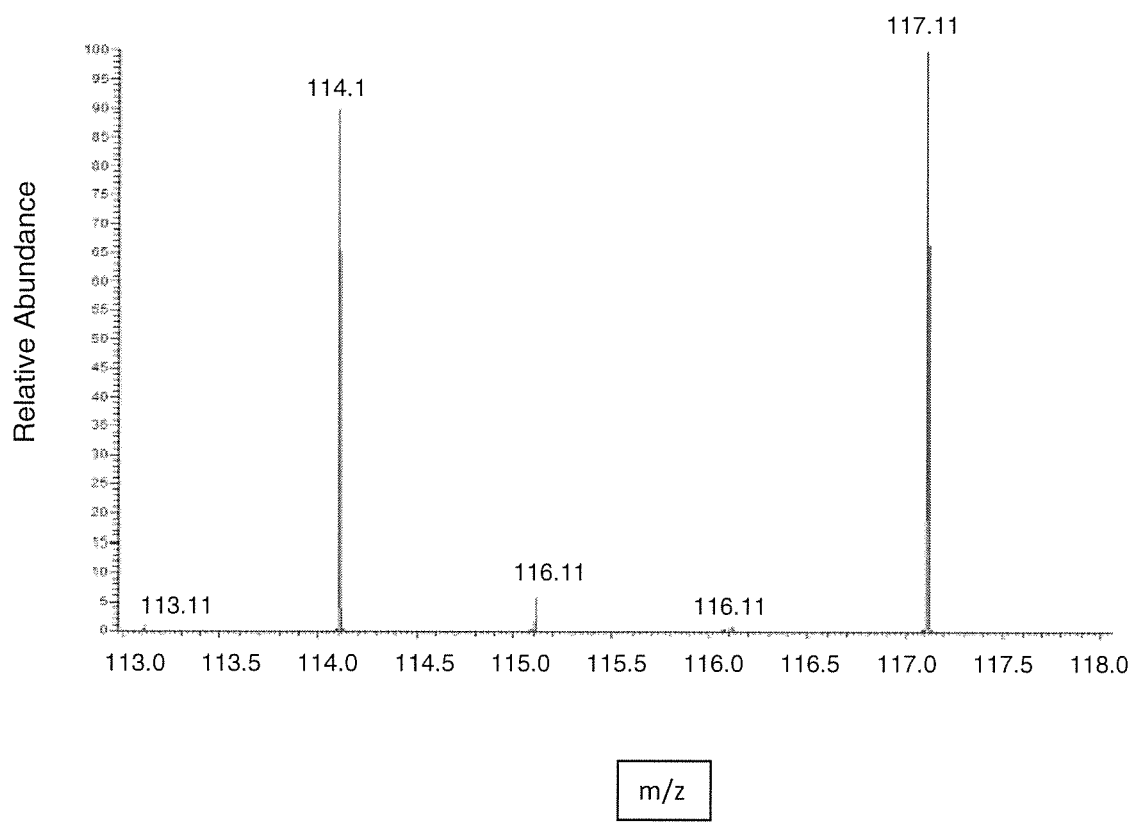
Figure 19:
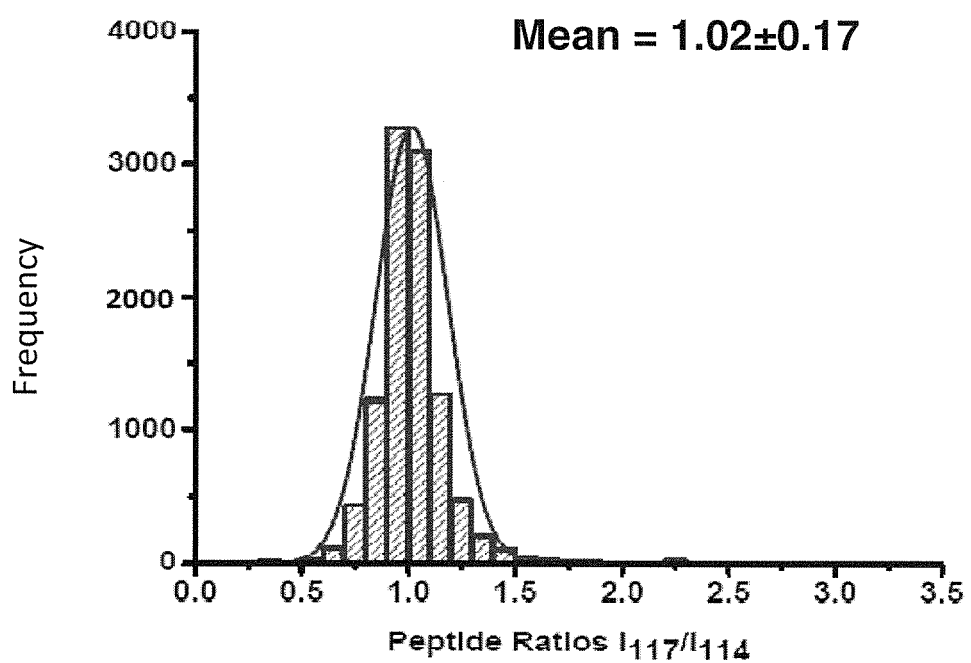
FIG. 19A-B presents exemplary data showing the reliability of Nano-LC-MS/MS quantitation (HCD) by peptide-to-protein inferencing of Complement C4 data in FIGS. 17 and 18.
Figure 19B:
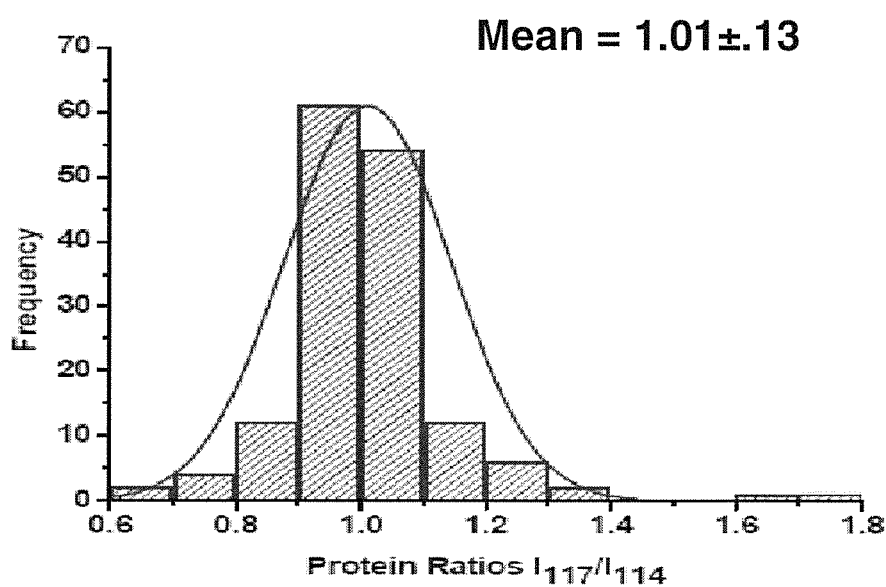
Figure 20A:
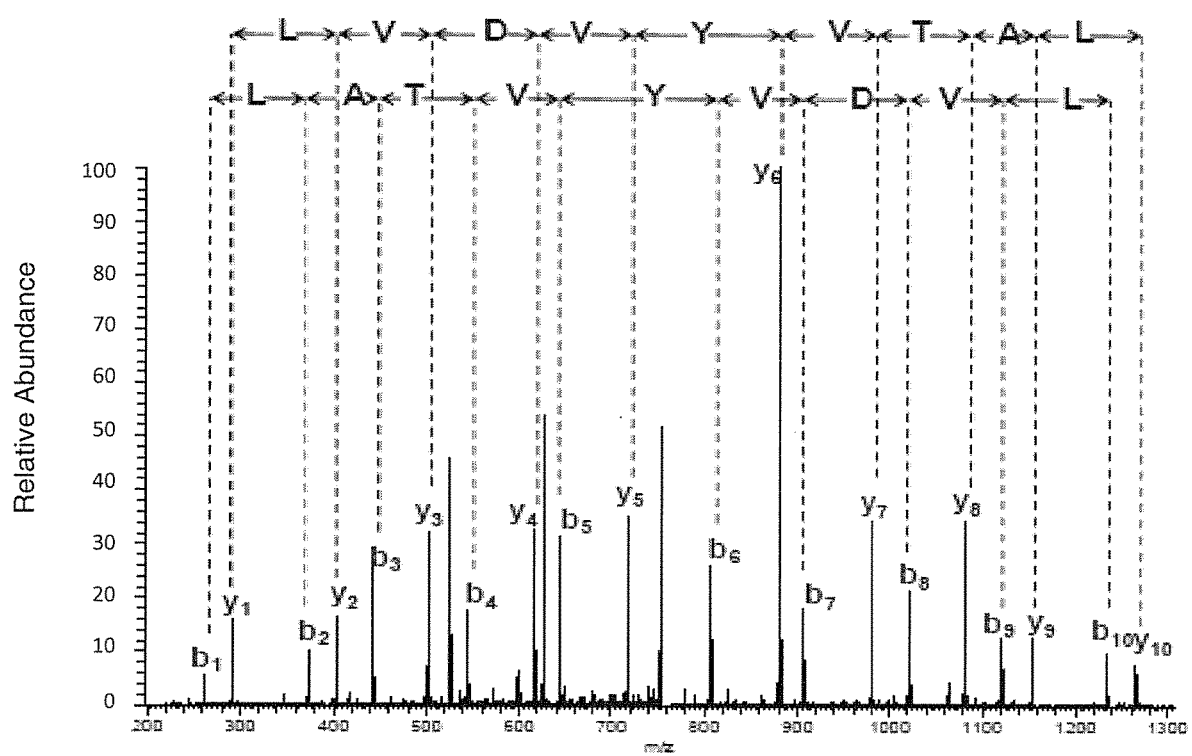
FIG. 20A-B presents representative Nano-LC-MS MS data for a peptide fragment (D(iTRAQ)LATVYVDVLK(iTRAQ)+2H)$^{2+}$ (SEQ ID NO: 1) of apolipoprotein A-1. Spectral Counts=1734; Unique peptides=24.
Figure 20B:
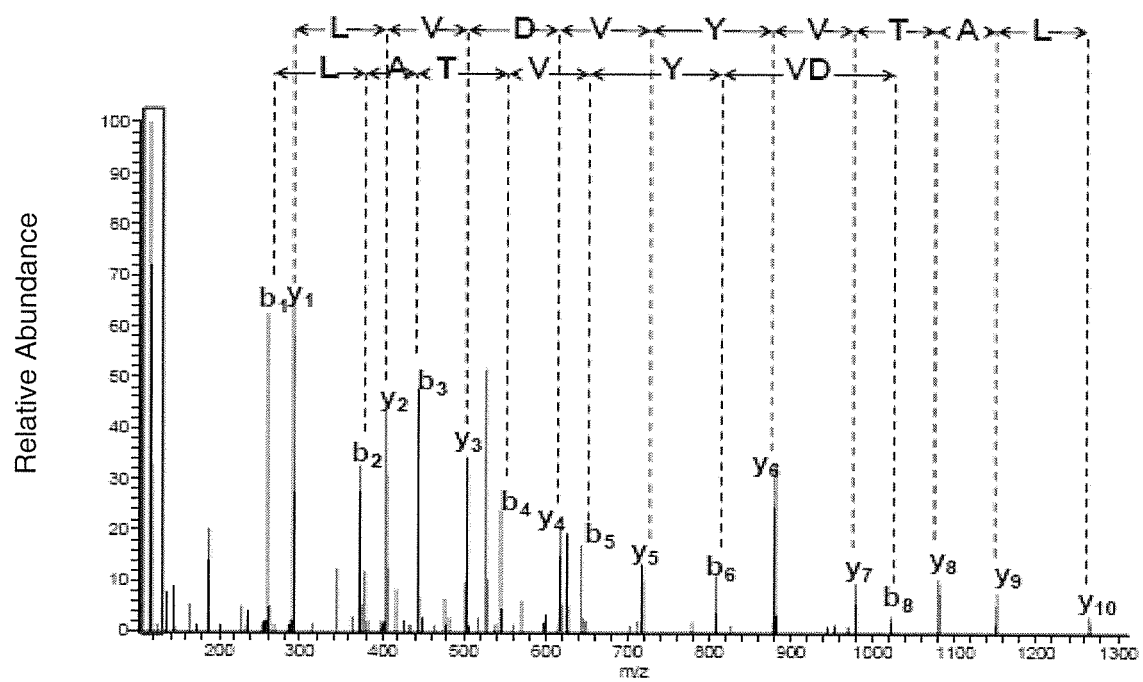
Figure 21A:
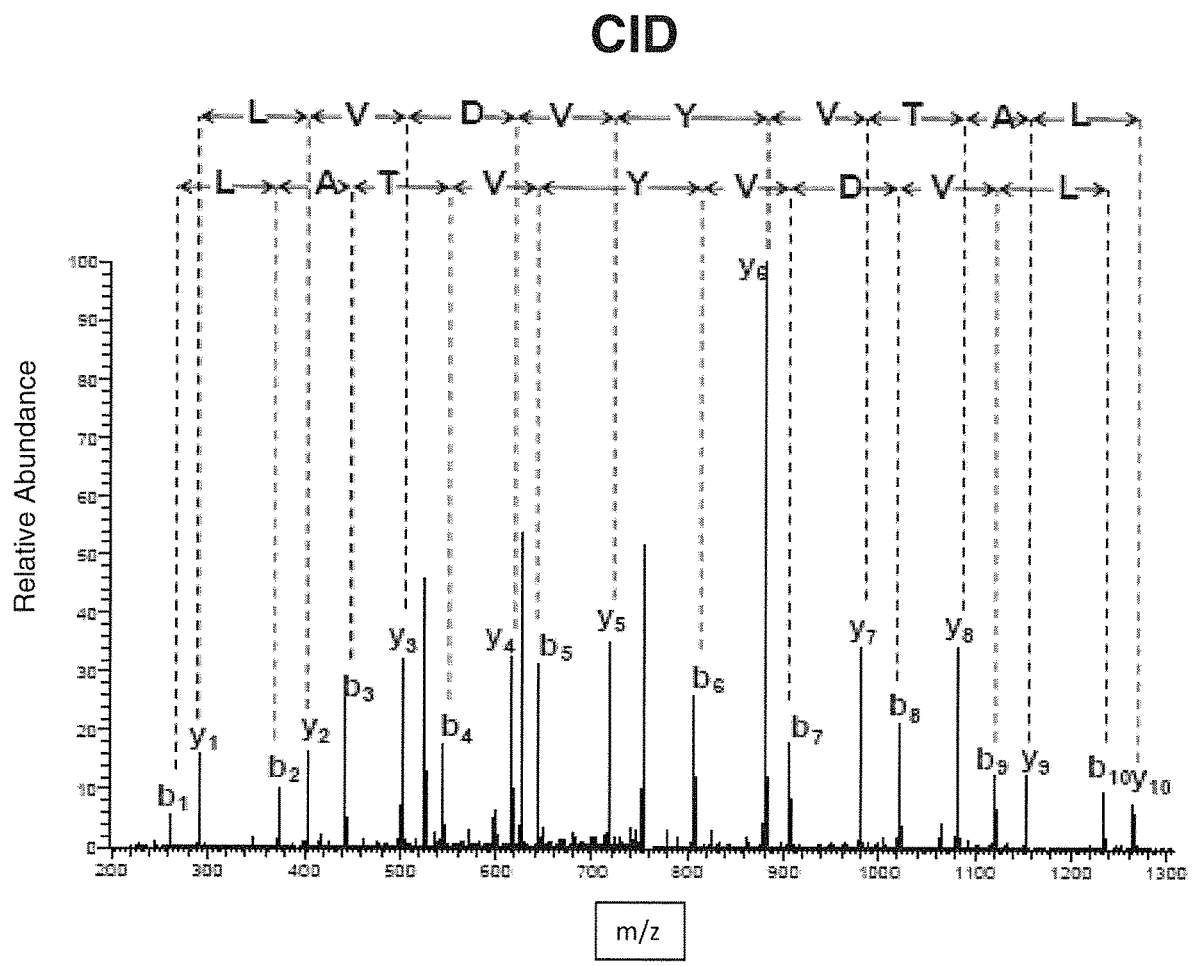
FIG. 21A: A CID spectra and analysis.
Figure 21B:
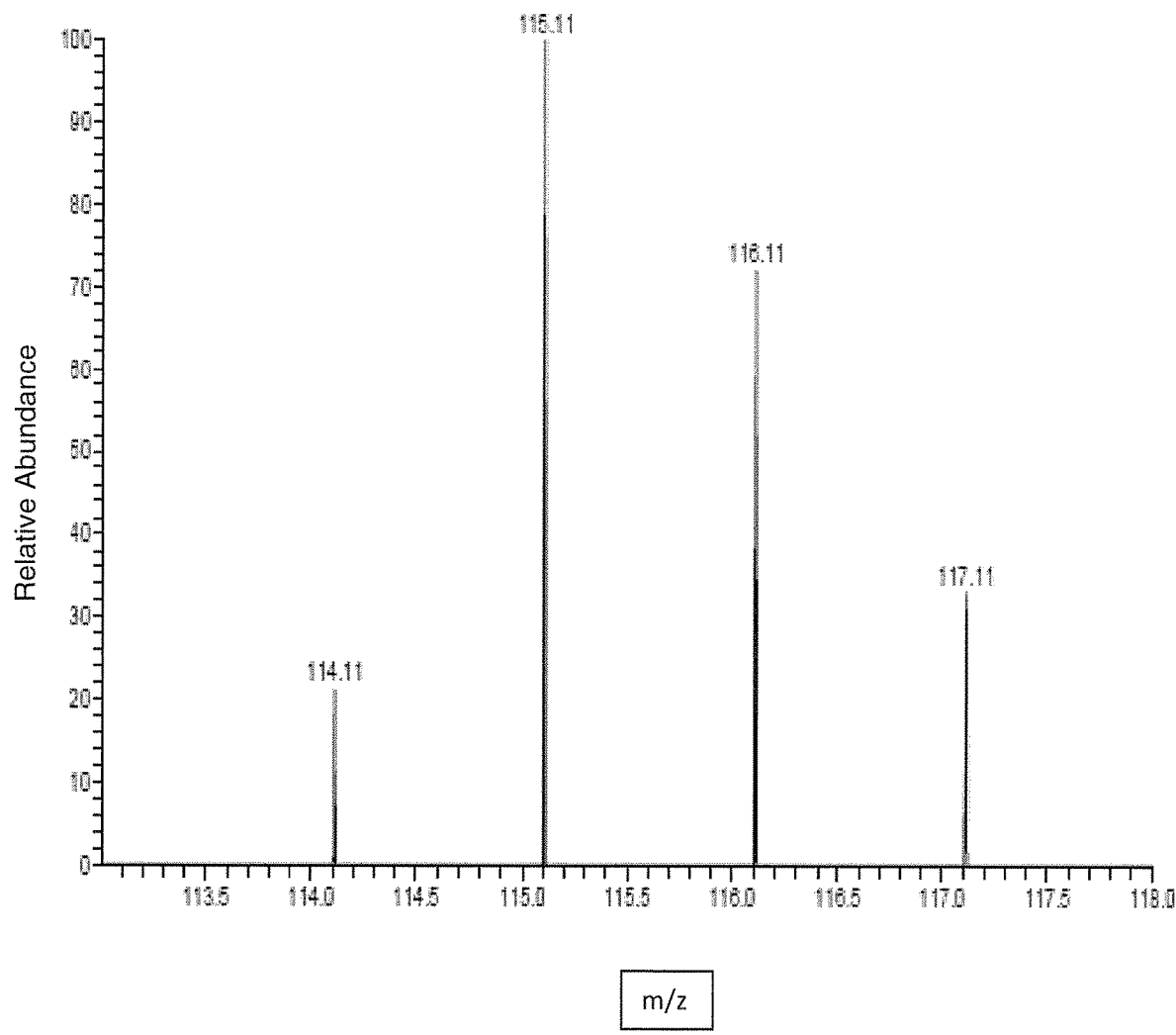
FIG. 21B: A HCD spectra and analysis.

Chromatograms obtained from MARS depletion and tandem MARS-depletion were shown to be reproducible (i.e., the relative standard deviation of unbound peaks and bound peaks were 1.6% and 0.4%, respectively.). See, FIGS. 10A and 10B.

III. Sepsis Biomarker Identification

This invention includes the identification of more than eighty human plasma proteins which may have the potential to serve as biomarkers for the diagnosis of sepsis in elderly patients. See, Table 3.

TABLE 3

Protein Level Ratios Comparing Elderly Patients
With and Without Severe Sepsis
(OY/ON): Proteins were quantified in at least six experiments
(≥1.30 or ≤0.77; Coefficient Variance ≤ 0.55)

| Acc No. | Protein Name | Mean | SD |
|---|---|---|---|
| P02741 | C-reactive protein | 0.521 | 0.221 |
| P02671 | Fibrinogen alpha chain | 0.597 | 0.129 |
| P02751 | Fibronectin | 0.624 | 0.314 |
| P07996 | Thrombospondin-1 | 0.645 | 0.335 |
| P02649 | Apolipoprotein E | 0.646 | 0.170 |
| P01011 | Alpha-1-antichymotrypsin | 0.683 | 0.183 |
| Q9Y6R7 | IgGFc-binding protein | 0.700 | 0.259 |
| Q9BXR6 | Complement factor H-related protein 5 | 0.716 | 0.181 |
| Q86UD1 | Out at first protein homolog | 0.742 | 0.193 |
| P08779 | Keratin, type I cytoskeletal 16 | 0.754 | 0.355 |
| P02775 | Platelet basic protein | 0.758 | 0.211 |
| P18428 | Lipopolysaccharide-binding protein | 0.762 | 0.321 |
| Q96PD5 | N-acetylmuramoyl-L-alanine amidase | 1.347 | 0.393 |
| Q15431 | Synaptonemal complex protein 1 | 1.372 | 0.620 |
| O14791 | Apolipoprotein L1 | 1.390 | 0.701 |
| P35858 | Insulin-like growth factor-binding protein complex acid labile subunit | 1.393 | 0.462 |
| P19823 | Inter-alpha-trypsin inhibitor heavy chain H2 | 1.397 | 0.528 |
| P02656 | Apolipoprotein C-III | 1.426 | 0.769 |
| O95445 | Apolipoprotein M | 1.438 | 0.483 |
| P02652 | Apolipoprotein A-II | 1.447 | 0.463 |
| P06276 | Cholinesterase | 1.452 | 0.474 |
| P05090 | Apolipoprotein D | 1.470 | 0.321 |
| P19827 | Inter-alpha-trypsin inhibitor heavy chain H1 | 1.576 | 0.582 |
| P02749 | Beta-2-glycoprotein 1 | 1.582 | 0.611 |
| P29622 | Kallistatin | 1.685 | 0.574 |
| Q9NXD2 | Myotubularin related protein 10 | 1.779 | 0.692 |
| Q04756 | Hepatocyte growth factor activator | 1.808 | 0.681 |
| Q86UV6 | Tripartite motif-containing protein 74 | 1.847 | 0.787 |
| Q6UXB8 | Peptidase inhibitor 16 | 2.028 | 0.782 |
| Q96KN2 | Beta-Ala-His dipeptidase | 2.060 | 0.931 |
| P02654 | Apolipoprotein C-I | 2.165 | 1.022 |

These proteins were identified and quantified using iTRAQ based chemistry in combination with liquid chromatography and mass spectrometry.

In one embodiment, the present invention contemplates a method comprising identifying protein pathway biomarkers of severe sepsis in patients with an infection. In one embodiment, the present invention contemplates a method comprising developing biomarkers of severe sepsis in elderly patients with an infection. In one embodiment, the present invention contemplates a method comprising developing protein pathway biomarkers of severe sepsis in non-elderly patients with an infection. Although it is not necessary to understand the mechanism of an invention it is believed that a sepsis proteomic pathway analysis may discover potential mechanisms and therapies for severe sepsis, potential mechanisms and therapies for age-related immune dysfunction, and/or potential mechanisms and therapies for age-related organ dysfunction in sepsis.

The proteins identified in this study have not been implicated and/or previously identified in the plasma of various aged elderly severe sepsis patients. For example, some interleukins were identified as differentially expressed. See, Table 4.

TABLE 4

Differential Interleukin Expression In Elderly Severe Sepsis Patients

| Interleukin 21 | YY/OY | 0.626 ± 0.169 |
| Interleukin 21 | YN/ON | 0.519 ± 0.105 |
| Interleukin 21 | YY/YN | 2.054 ± 0.105 |
| Interleukin 21 | OY/ON | 1.735 ± 0.443 |
| Interleukin 19 | YY/OY | 0.508 ± 0.046 |
| Interleukin 19 | YN/ON | 0.426 ± 0.051 |
| Interleukin 19 | YY/YN | 1.924 ± 0.185 |
| Interleukin 19 | OY/ON | 1.609 ± 0.108 |

IL-21 is believed to be homologous to IL-2, IL-4 and IL-15 and is generally considered to be a proinflammatory cytokine. IL-19 is believed to belong to the IL-10 family of cytokines along with IL-10, IL-20, IL-22. IL-19 has been reported to be up-regulated in monocytes following stimulation with LPS.

Some blood factors were also seen to be differentially expressed in elderly patients with severe sepsis. See, Table 5.

TABLE 5

Differential Blood Factor Expression In Elderly Patients With Severe Sepsis

|  | YY/OY | YN/ON | YY/YN | OY/ON |
| --- | --- | --- | --- | --- |
| Factor XIII, A Chain | 0.710 ± 0.158 | N.D. | N.D. | N.D. |
| Factor XII | 0.767 ± 0.093 | N.D. | N.D. | 1.563 ± 1.163 |
| Von Willebrand Factor | 1.161 ± 0.821 | N.D. | 2.047 ± 1.297 | N.D. |
| Fibrinogen alpha | 2.058 ± 0.577 | 0.246 ± 0.120 | 2.441 ± 0.719 | 0.597 ± 0.129 |

N.D. = Not Determined

Some lipid factors were also seen to be differentially expressed is elderly patients with severe sepsis. See, Table 6.

TABLE 6

Differential Lipid Factor Expression In Elderly Patients With Severe Sepsis

|  | YY/OY | YY/ON | YY/YN | OY/ON |
| --- | --- | --- | --- | --- |
| Lipopolysaccharide Binding Protein | 2.499 ± 0.604 | N.D. | 2.201 ± 0.502 | N.D. |
| Apolipoprotein E | 1.692 ± 0.309 | 0.522 ± 0.164 | 2.105 ± 0.301 | 0.646 ± 0.170 |
| Apolipoprotein AII | 0.426 ± 0.073 | 1.805 ± 0.685 | 0.502 ± 0.080 | 1.447 ± 0.463 |
| Apolipoprotein CIII | 0.578 ± 0.099 | 2.961 ± 1.372 | 0.690 ± 0.294 | 1.426 ± 0.769 |

The data presented herein was derived from patients exhibiting symptoms of community acquired pneumonia using a semi-quantitative plasma proteomics workflow. Cao et al., "Additions to the human plasma proteome via a tandem MARS depletion iTRAQ-based workflow" *International Journal of Proteomics* 2013 Article ID 654356 ((2013). This technique includes, but is not limited to, tandem immuno-affinity depletion, isobaric tags for relative and absolute quantitation (iTRAQ) labeling, strong cation exchange (SCX) fractionation, and nanoflow liquid chromatography (LC) coupled to high resolution mass spectrometry (MS).

In one embodiment, the present invention contemplates a sepsis proteomic expression profile comprising proteins that are differentially expressed between young adults without severe sepsis (YN), elderly adults without severe sepsis (ON), young adults with severe sepsis (YY) and/or elderly adults with severe sepsis (OY). Although it is not necessary to understand the mechanism of an invention, it is believed that many differentially-expressed proteins are unique to either younger or older adults which may explain an increased risk of severe sepsis in older adults. It is further believed that many differentially-expressed proteins that are common to the young and elderly adult groups may also be identified. The data presented herein demonstrate that the fold-change direction observed for differentially expressed proteins in common between young and elderly patients varies depending on patient age and thus may explain higher risk of severe sepsis in older adults.

The data presented herein identify fifty-nine (59) differentially-expressed proteins were identified in comparisons from both age groups (i.e., YS/YC and OS/OC). See, Table 7.

TABLE 7

List of differentially-expressed proteins in patients with severe sepsis as a function of age

| Acc. No.[a] | Protein Name | YS/YC (mean ± SD[b]) | OS/OC (mean ± SD) |
|---|---|---|---|
| O14791 | Apolipoprotein L1 | / | 1.390 ± 0.701 |
| O95445 | Apolipoprotein M | / | 1.438 ± 0.483 |
| P01008 | Antithrombin-III | 0.596 ± 0.064 | / |
| P01011[c] | Alpha-1-antichymotrypsin | 1.577 ± 0.867 | 0.683 ± 0.183 |
| P02649 | Apolipoprotein E | 2.105 ± 0.301 | 0.646 ± 0.170 |
| P02652 | Apolipoprotein A-II | 0.502 ± 0.080 | 1.447 ± 0.463 |
| P02654 | Apolipoprotein C-I | / | 2.165 ± 1.022 |
| P02656 | Apolipoprotein C-III | 0.690 ± 0.294 | 1.426 ± 0.769 |
| P02671 | Fibrinogen alpha chain | 2.441 ± 0.719 | 0.597 ± 0.129 |
| P02675 | Fibrinogen beta chain | 2.102 ± 0.579 | / |
| P02679 | Fibrinogen gamma chain | 2.077 ± 0.720 | / |
| P02735 | Serum amyloid A protein | 3.058 ± 1.088 | / |
| P02741 | C-reactive protein | 3.268 ± 1.070 | 0.521 ± 0.221 |
| P02749 | Beta-2-glycoprotein 1 | / | 1.582 ± 0.611 |
| P02750 | Leucine-rich alpha-2-glycoprotein | 2.140 ± 0.296 | / |
| P02751 | Fibronectin | / | 0.624 ± 0.314 |
| P02753 | Retinol-binding protein 4 | 0.525 ± 0.088 | / |
| P02763 | Alpha-1-acid glycoprotein 1 | 2.033 ± 0.426 | / |
| P02766 | Transthyretin | 0.440 ± 0.094 | / |
| P02774 | Vitamin D-binding protein | 0.568 ± 0.084 | / |
| P02775 | Platelet basic protein | / | 0.758 ± 0.211 |
| P04114 | Apolipoprotein B-100 | 1.523 ± 0.253 | / |
| P04259 | Keratin, type II cytoskeletal 6B | 0.521 ± 0.056 | / |
| P04275 | von Willebrand factor | 2.047 ± 0.340 | / |
| P04278 | Sex hormone-binding globulin | 0.698 ± 0.258 | / |
| P05090 | Apolipoprotein D | / | 1.470 ± 0.321 |
| P05154 | Plasma serine protease inhibitor | 0.726 ± 0.457 | / |
| P05452 | Tetranectin | 0.640 ± 0.103 | / |
| P05546 | Heparin cofactor 2 | 0.707 ± 0.255 | / |
| P06276 | Cholinesterase | / | 1.452 ± 0.474 |
| P06396 | Gelsolin | 0.546 ± 0.098 | / |
| P07996 | Thrombospondin-1 | / | 0.645 ± 0.335 |
| P08779 | Keratin, type I cytoskeletal 16 | / | 0.754 ± 0.355 |
| P10909 | Clusterin | 0.731 ± 0.297 | / |
| P13645 | Keratin, type I cytoskeletal 10 | 0.582 ± 0.064 | / |
| P15169 | Carboxypeptidase N catalytic chain | 1.312 ± 0.364 | / |
| P16070 | CD44 antigen | 1.618 ± 0.545 | / |
| P18428 | Lipopolysaccharide-binding protein | 2.201 ± 0.502 | 0.762 ± 0.321 |
| P19652 | Alpha-1-acid glycoprotein 2 | 2.169 ± 0.598 | / |
| P19823 | Inter-alpha-trypsin inhibitor heavy chain H2 | / | 1.397 ± 0.528 |
| P19827 | Inter-alpha-trypsin inhibitor heavy chain H1 | / | 1.576 ± 0.582 |
| P20061 | Transcobalamin-1 | / | / |
| P20851 | C4b-binding protein beta chain | 1.391 ± 0.460 | / |
| P29622 | Kallistatin | / | 1.685 ± 0.574 |
| P35542 | Serum amyloid A-4 protein | 0.476 ± 0.044 | / |
| P35858 | Insulin-like growth factor-binding protein complex acid labile subunit | / | 1.393 ± 0.462 |
| P61626 | Lysozyme C | 1.905 ± 0.958 | / |
| P61769 | Beta-2-microglobulin | 1.887 ± 1.020 | / |
| P80108 | Phosphatidylinositol-glycan-specific phospholipase D | 0.390 ± 0.064 | / |
| Q03591 | Complement factor H-related protein 1 | 1.312 ± 0.595 | / |

TABLE 7-continued

List of differentially-expressed proteins in patients with severe sepsis as a function of age

| Acc. No.[a] | Protein Name | YS/YC (mean ± SD[b]) | OS/OC (mean ± SD) |
|---|---|---|---|
| Q04756 | Hepatocyte growth factor activator | / | 1.808 ± 0.681 |
| Q15431 | Synaptonemal complex protein 1 | / | 1.372 ± 0.620 |
| Q6UXB8 | Peptidase inhibitor 16 | / | 2.028 ± 0.782 |
| Q86UD1 | Out at first protein homolog | / | 0.742 ± 0.193 |
| Q86UV6 | Tripartite motif-containing protein 74 | / | 1.847 ± 0.787 |
| Q96KN2 | Beta-Ala-His dipeptidase | / | 2.060 ± 0.931 |
| Q96PD5 | N-acetylmuramoyl-L-alanine amidase | 0.576 ± 0.061 | 1.347 ± 0.393 |
| Q9BXR6 | Complement factor H-related protein 5 | / | 0.716 ± 0.181 |
| Q9NXD2 | Myotubularin-related protein 10 | / | 1.779 ± 0.692 |
| Q9Y6R7 | IgGFc-binding protein | / | 0.700 ± 0.259 |

[a]Accession number provided from the Uniprothuman database(Apr. 25, 2010, 20295 sequences).
[b]Mean and SD values are calculated based on the reporter ion ratios for proteins quantified in at least 6 biological experiments.
[c]Proteins quantified in both comparisons are in bold.

The measured fold-change values reported in Table 7 include the mean and standard deviation (SD) for each protein based on the ratios averaged across all biological replicates.

As described herein, an iTRAQ-based semi-quantitative proteomics workflow was employed to identify differentially-expressed proteins in 50-65 and 70-85 year old CAP patients who developed severe sepsis as compared to those patients that did not. For example, a tandem MARS depletion was performed on a MARS Hu-6 column to effectively remove high abundance proteins. The collected data was derived from patient samples from the four groups (i.e., YC, YS, OC and OS) that were randomly assigned to one of four iTRAQ reagents in a blind fashion across ten SCX-LC-MS/MS experiments.

Figure 22A:
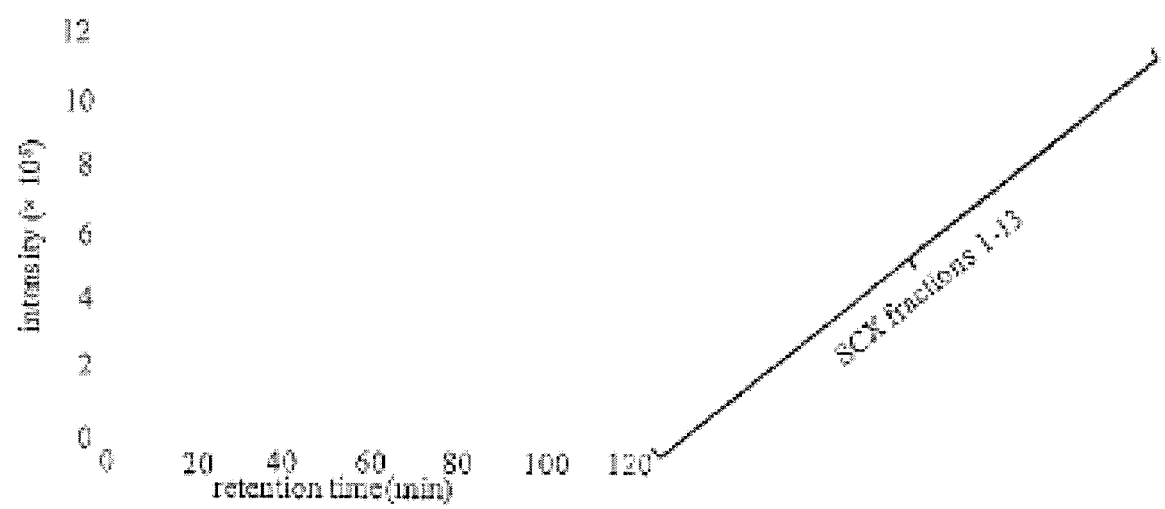
FIG. 22A-G presents an exemplary LC chromatogram subsequent to SCX fractionation.
Figure 22B:
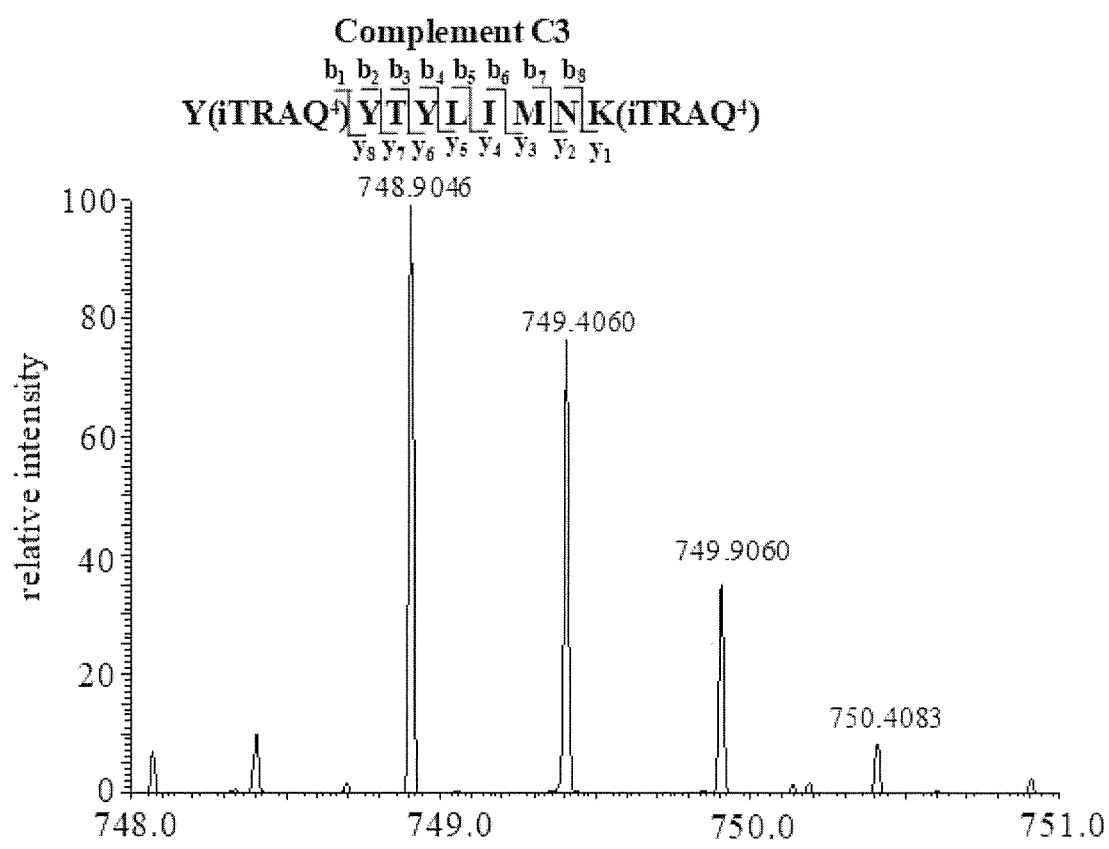
Figure 22C:
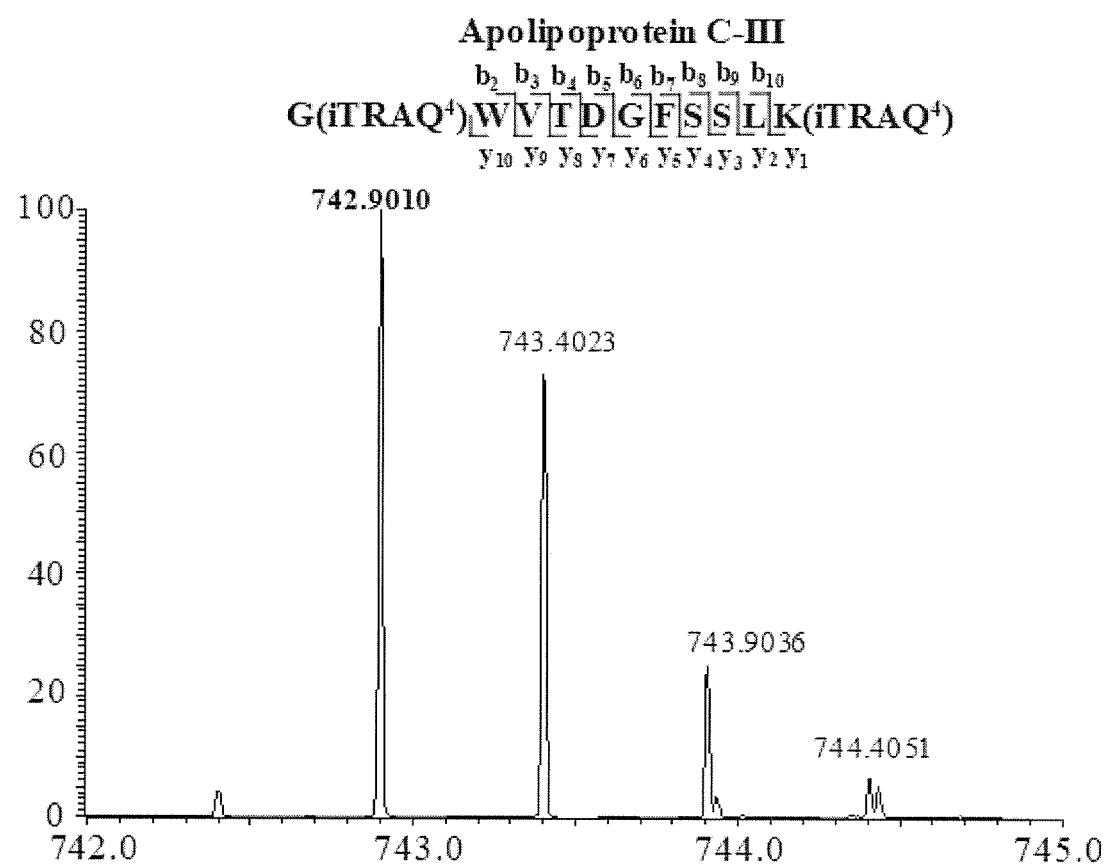
Figure 22D:
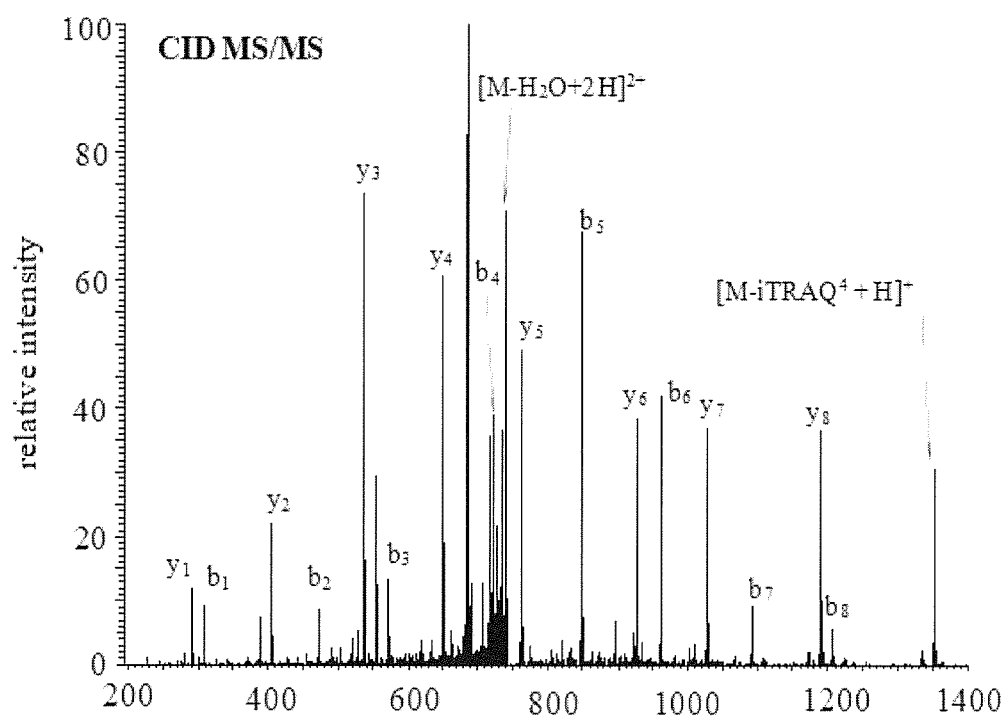
Figure 22E:
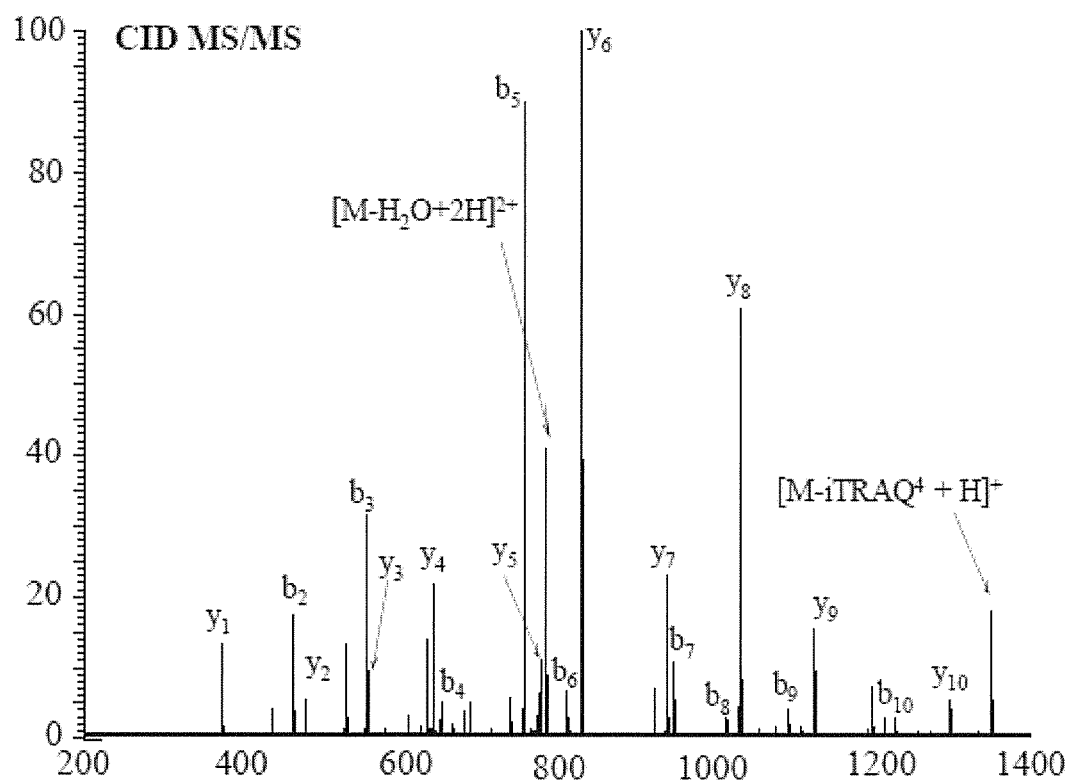
Figure 22F:
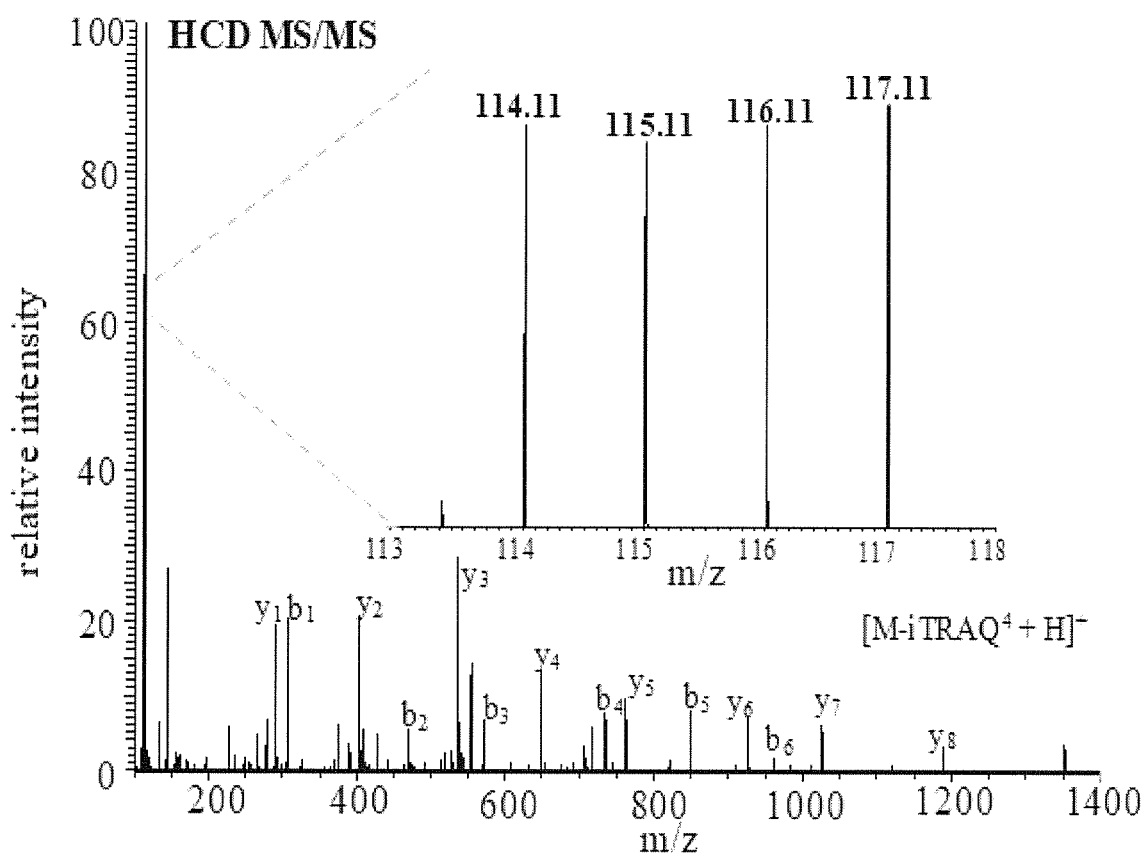
Figure 22G:
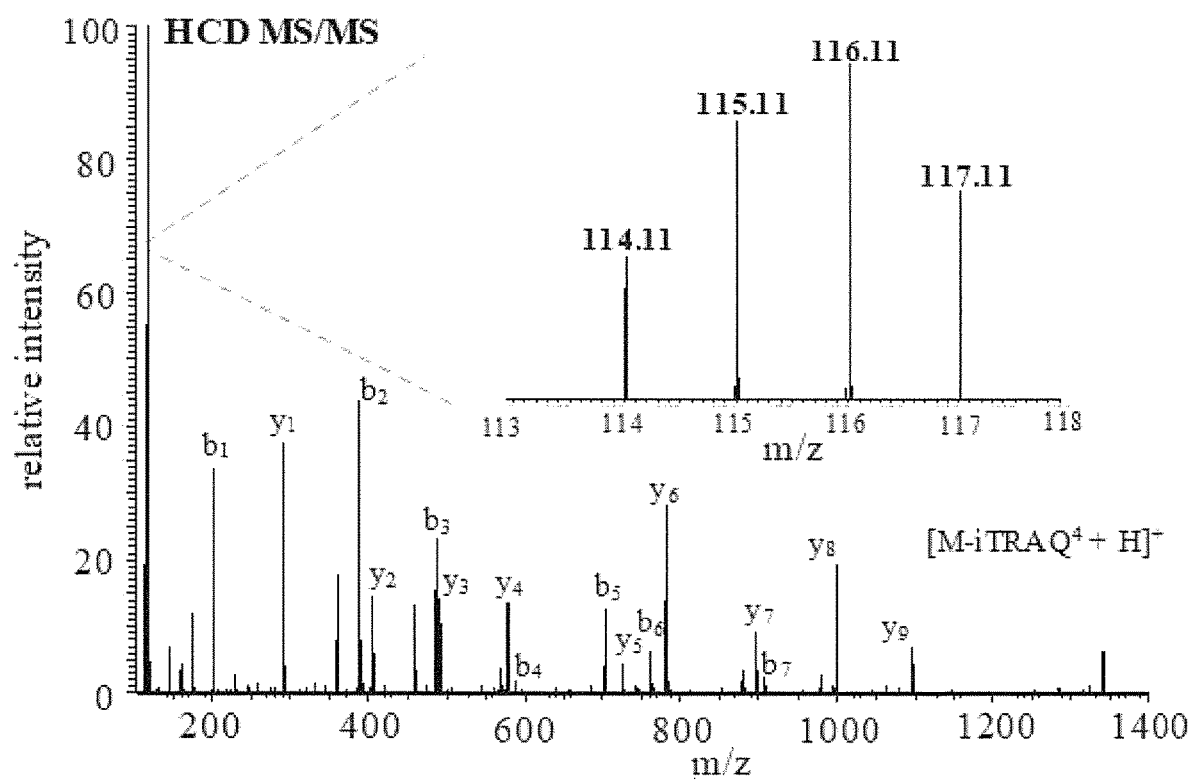

An exemplary LC chromatogram for 13 SCX fractions of pooled iTRAQ 4-plex samples is shown. See, FIG. 22A-G. Triplicate LC-MS/MS runs performed for each fraction were reproducible. Example spectra demonstrate peak isolation and fragmentation. See, FIGS. 22B-G. The data show doubly-charged peptides at m/z, 748.9046 and 742.9010 in SCX fractions 7 and 6 that were eluted from the column at $t_r$=57.20 min and 37.26 min, respectively. See, FIGS. 22B and 22C, respectively. The CID MS/MS spectra display a consecutive series of b- and y-fragment ions used to assign the peptides as $[YYTYLIMNK+2H]^{2+}$ (SEQ ID NO: 3) of protein Complement C3 and $[GWVTDGFSSLK+2H]^{2+}$ (SEQ ID NO: 4) of protein Apolipoprotein CIII, respectively. See, FIGS. 22D and 22E, respectively. A mass increase of 145 Da was observed for b1 and y1 ions for each of the two peptides, indicating iTRAQ labeling at the N-terminus and the presence of lysine at the C-terminus. HCD MS/MS spectra also contain a series of b- and y-ions used to confirm the sequence of peptides. See, FIGS. 22F and 22G, respectively. The lower m/z region of the HCD MS/MS spectra shows the intensity of the reporter ions which is used to quantify the peptides. See, inserts, FIGS. 22F and 22G, respectively. The ratios across the four groups were 1.0:0.9:1.0:1.0 and 1.0:1.3:2.5:0.5 for reporter ions 114:115:116:117 from Complement C3 and Apo CIII, respectively. See, FIGS. 22F and 22G, respectively.

Figure 23:
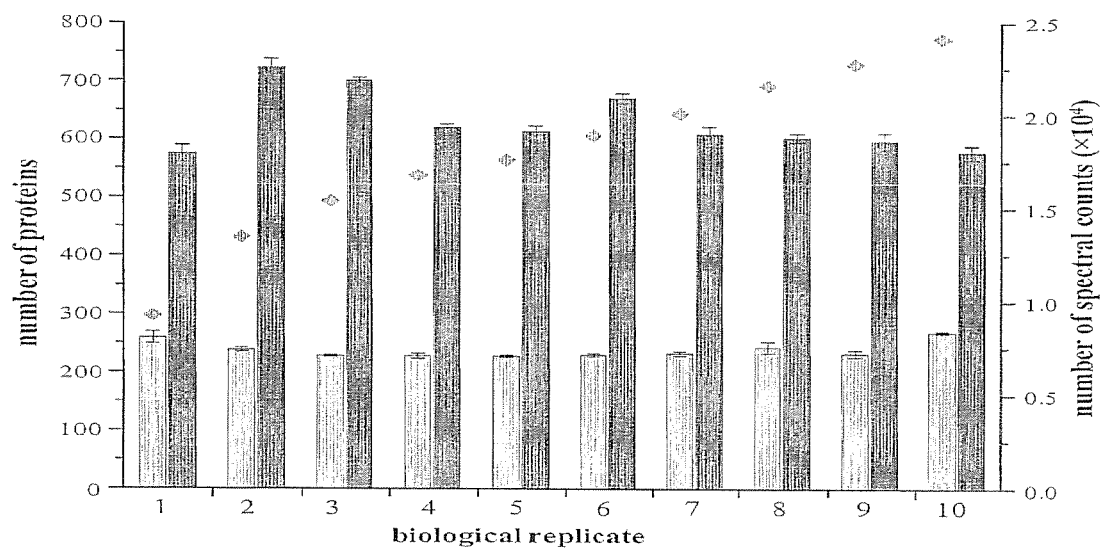
FIG. 23 presents exemplary data showing an average number±standard deviation of proteins (light bars) and spectral counts (dark bars) identified in each experiment. The cumulative number of proteins (diamonds) identified with each subsequent experiment is also shown.

The data presented herein shows an average number±standard deviation of spectral counts (SCs) and proteins identified in each of the ten biological replicate experiments. See, FIG. 23. An average of 283±14 proteins and 59,645±4129 spectral counts were identified and similar results were obtained across individual experiments. The total number of proteins identified increases with each pooled sample experiment such that a total of 772 unique proteins were identified from all plasma samples. Based on SCs, the three most abundant proteins are Complement C3 (49,749 SCs), α-2-macroglobulin (47,273 SCs) and Apolipoprotein A1 (28,261 SCs).

Figure 24A:
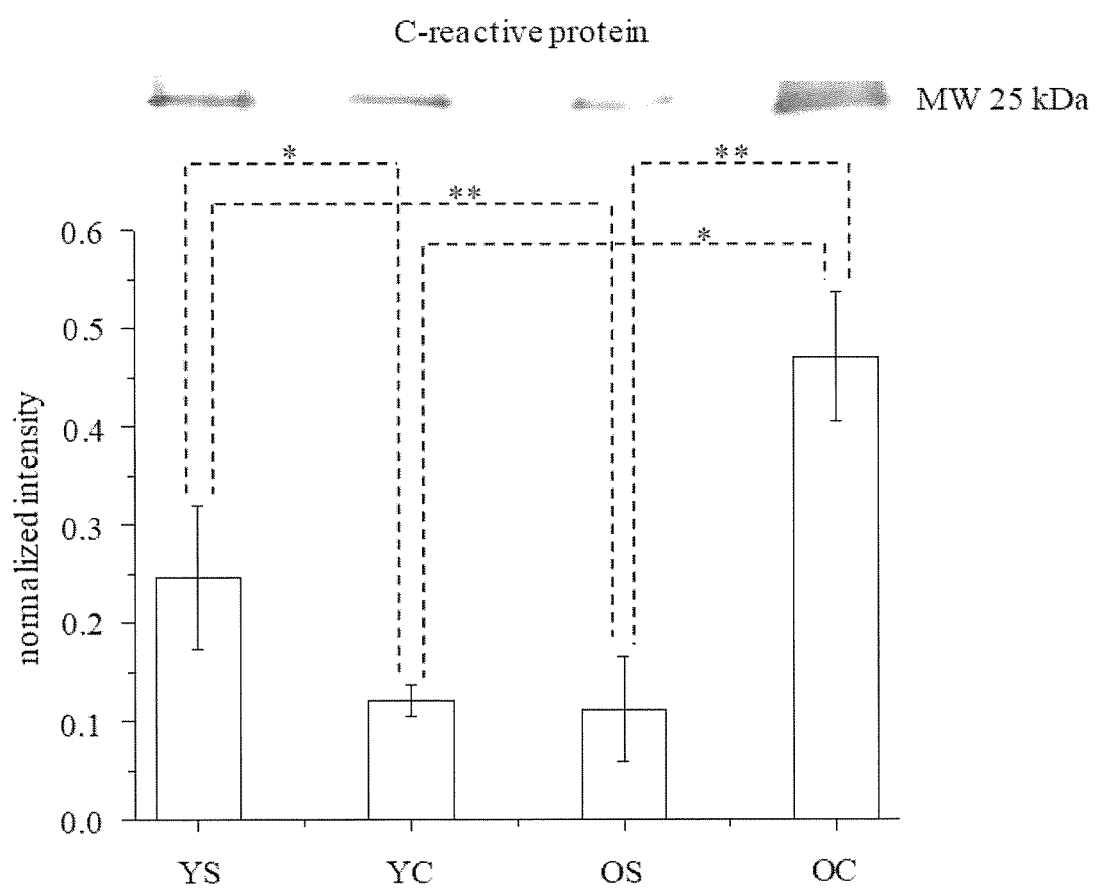
FIG. 24A-C presents exemplary data showing Western blotting images and histogram displaying a normalized intensity±standard deviation (n=6) of the proteins across each group. The intensity for each individual band is normalized to the total intensity of the blot.
Figure 24B:
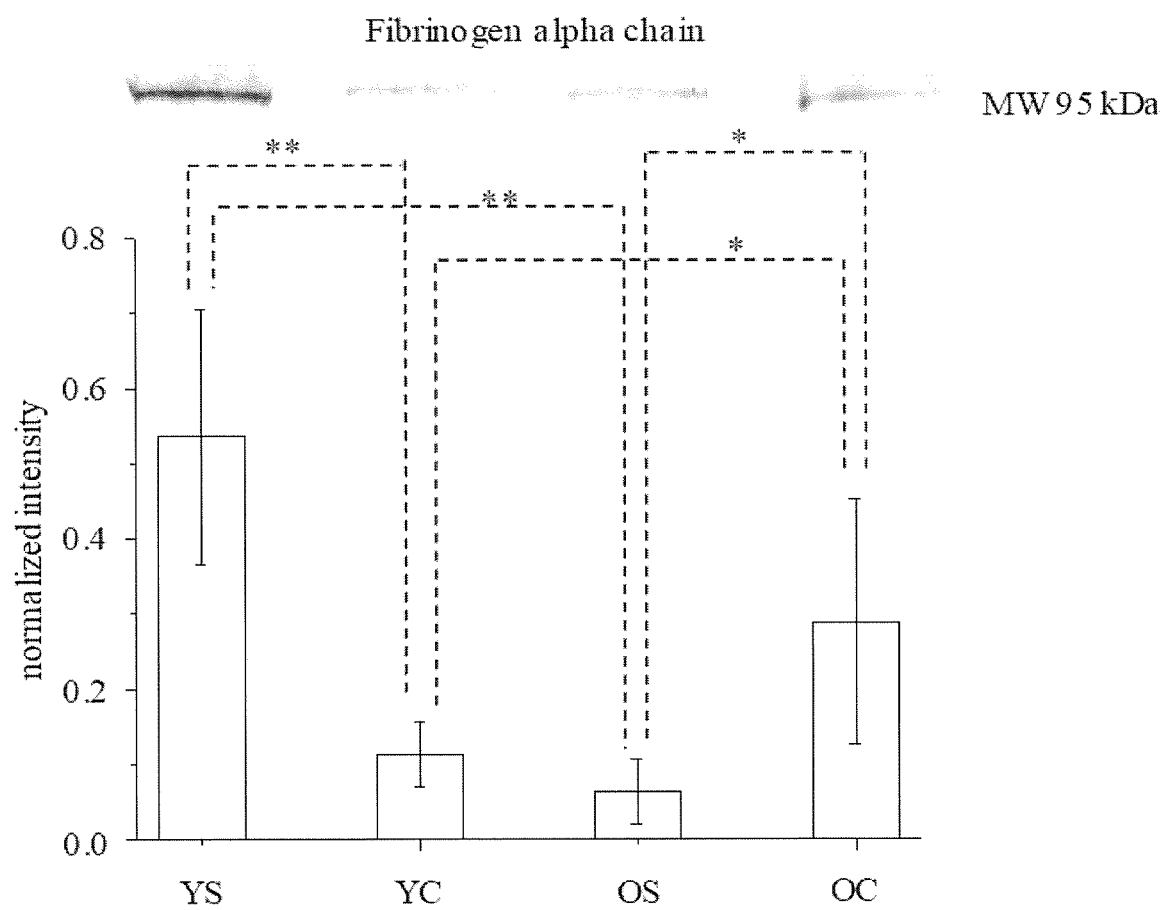
Figure 24C:
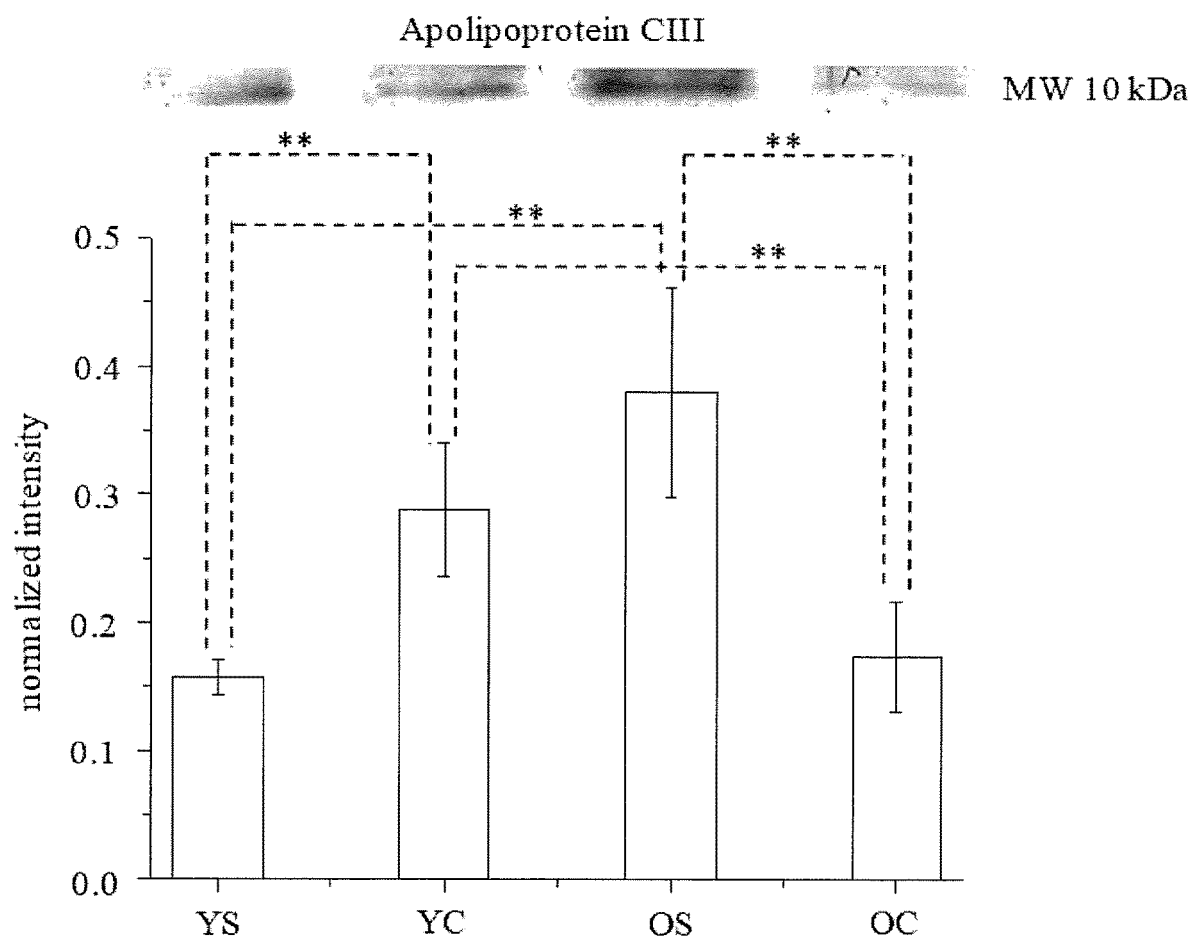

Western blotting analysis was employed to generate a secondary measurement for several differentially expressed proteins. Proteins involved in an acute phase response (i.e., CRP), coagulation pathway (i.e., FAC) pathway and lipid metabolism (i.e., ApoCIII) were selected. See, FIGS. 24A-C. The histogram plots represent the normalized intensities corresponding to the density of the band spots for each group. The relative abundance obtained from the iTRAQ-based sepsis proteomics workflow of CRP, FAC and ApoCIII were 3.27:1.00:1.74:3.34, 2.44:1.00:2.97:4.98, and 0.69:1.00:0.58:0.40, respectively.

Figure 25:
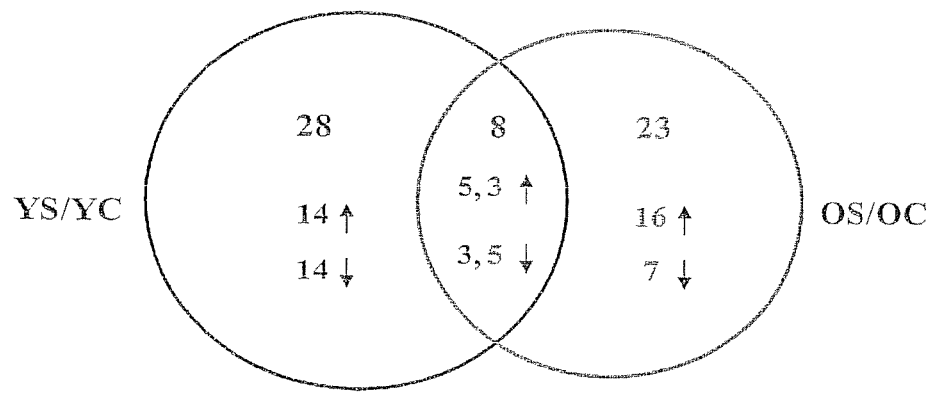
FIG. 25 presents an illustrative Venn diagram of differentially-expressed proteins for each age group (i.e., YS/YC 50-65 years old and OS/OC 70-85 years old). The number of proteins that have higher (↑) or lower (↓) fold-change values in each comparison are also shown.

These observed Western blot data are consistent with the measured iTRAQ results for the fifty-nine differentially-expressed proteins that were identified in comparisons from both age groups (i.e., YS/YC and OS/OC)(Y=young, O=elderly; S=sepsis, C=control or without sepsis). See, Table 7. The measured fold-change values reported in the table include the mean and SD for each protein based on the ratios averaged across all biological replicates. As shown, 28 proteins are differentially-expressed in the population of 50-65 year olds (i.e., YS/YC) in which 14 have higher levels and 14 have lower levels in patients with severe sepsis compared to those with CAP. See, FIG. 25. In the population of 70-85 year olds (i.e., OS/OC), 23 proteins are differentially-expressed, in which 16 and seven have higher and lower levels in patients with severe sepsis, respectively. Of the 59 total differentially-expressed proteins, eight are in common amongst both age groups. Interestingly, however the direction of the fold change differs in younger and older adults. Specifically, alpha-1-antichymotrypsin (A1ACT), apolipoprotein (Apo) E, fibrinogen a chain, C-reactive protein (CRP), and LPS binding protein (LBP) levels were higher in younger adults with severe sepsis but lower in older adults with severe sepsis relative to age-matched controls, suggesting that lower levels of these proteins is associated with increased risk and incidence of severe sepsis in older adults. On the other hand, Apo A11, Apo CIII, and N-acetylmuranoyl-L-anlanineamidase have lower and higher levels in younger and older with severe sepsis, respectively, suggesting that higher levels of these proteins may be factors for increased severe sepsis risk in older adults.

Figure 26:
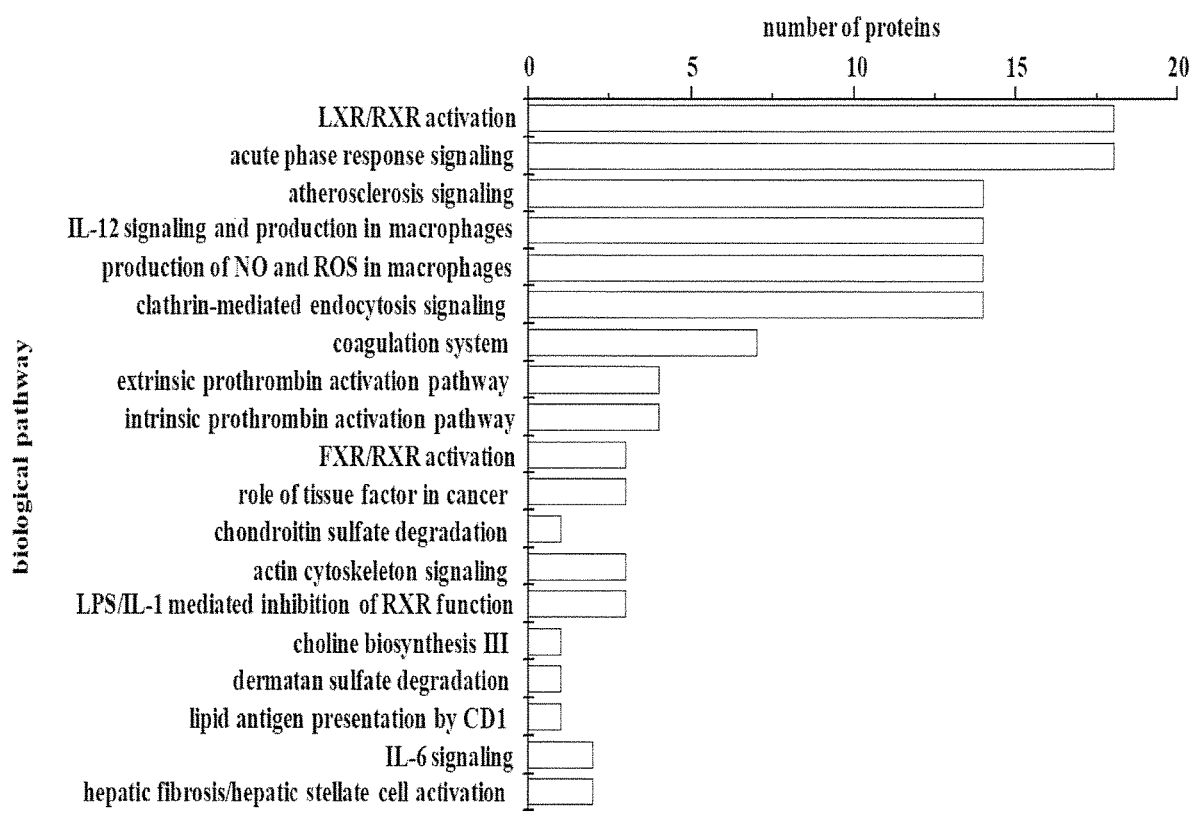
FIG. 26 presents exemplary data showing a histogram plot of biological pathways associated with differentially expressed proteins as a function of severity of sepsis (N=59). The p value cutoff for the Ingenuity Pathway Analysis (IPA) is p<0.05.

Using an Ingenuity Pathway Analysis method, nineteen (19) biological pathways were significantly over-represented (p<0.05) for the 59 identified differentially-expressed proteins. See, FIG. 26. The most represented pathways include LXR/RXR activation and acute phase response signaling whereby 18 proteins are associated with each of these pathways. Next, many differentially-expressed proteins are involved in atherosclerosis signaling, interleukin (IL)-12 signaling and production of NO and reactive oxygen species in macrophages, and endocytosis signaling. Fewer proteins are involved in the remaining biological pathways such as actin cytoskeleton and IL-6 signaling.

IV. Sepsis Proteomic Pathway Expression Profiles

In one embodiment, the present invention contemplates determining the effects of aging on severe sepsis risk by evaluating an acute plasma proteome. While sepsis can occur as early as the neonatal stage, incidence and morbidity increases with age and rises sharply after 65 years, presumably due to immunosenescence and high levels of inflammatory proteins. Martin et al., "The effect of age on the development and outcome of adult sepsis" *Critical Care Medicine* 34:15-21 (2006); and Opal et al., "The immunopathogenesis of sepsis in elderly patients" *Clinical Infectious Diseases* 41:S504-S512 ((2005); McDonald et al., "Aging is associated with impaired thrombus resolution in a mouse model of stasis induced thrombosis" *Thrombosis Research* 125:72-78 (2010); Turnbull et al., "Effects of aging on the immunopathologic response to sepsis. *Critical Care Medicine* 37, 1018-1023 (2009); Yamamoto et al., "Aging accelerates endotoxin-induced thrombosis: increased responses of plasminogen activator inhibitor-1 and lipopolysaccharide signaling with aging" *The American Journal of Pathology* 161:1805-1814 (2002); Cohen et al., "Coagulation and activation of inflammatory pathways in the development of functional decline and mortality in the elderly" *The American Journal of Medicine* 114:180-187 (2003); Downie et al., "Community-acquired neonatal and infant sepsis in developing countries: efficacy of WHO's currently recommended antibiotics—systematic review and meta-analysis" *Archives of Disease in Childhood* 98:146-154 (2013); Karumbi et al., "Topical umbilical cord care for prevention of infection and neonatal mortality" *Pediatric Infectious Disease Journal* 32:78-83 (2013); Kaplan et al., "Hospitalized community-acquired pneumonia in the elderly" *American Journal of Respiratory and Critical Care Medicine* 165:766-772 (2002); Girard et al., "Bacteremia and sepsis in older adults" *Clinics In Geriatric Medicine* 23:633-647 (2007); Fulop et al., "Role of immunosenescence in infections and sepsis in the elderly" *In: Handbook on Immunosenescence*, Fulop et al., Eds., pp. 965-977, (2009) Springer Netherlands; and Bruunsgaard et al., "Impaired production of proinflammatory cytokines in response to lipopolysaccharide (LPS) stimulation in elderly humans" *Clinical And Experimental Immunology* 118:235-241 (1999). However, none of these reports have identified significant differences with age for inflammatory and coagulation proteins and cell surface markers in patients with severe sepsis. Kale et al., "The effects of age on inflammatory and coagulation-fibrinolysis response in patients hospitalized for pneumonia" *PLoS ONE* 5:e13852 (2010).

The data presented herein provide the basis for an age-related sepsis proteomic expression profile that identified proteins involved various biological pathways including, but not limited to, acute phase signaling, coagulation pathway, and lipid/or metabolism that are differentially-expressed in an elderly population.

A. Acute Phase Response Pathways

Sepsis is believed to induce a pro-inflammatory state which can be characterized by elevated levels of pro-inflammatory cytokines, such as IL-6, IL-10 and tumor necrosis factor (TNF)-α. Cohen J., "The immunopathogenesis of sepsis" *Nature* 420:885-891 (2002). These pro-inflammatory cytokines regulate acute phase responses and the expression of acute phase proteins (APPs). Altered expression of APPs has been demonstrated in sepsis. For example, increased levels of α-1-acid glycoprotein (A1 AG), A1ACT, and LBP and decreased levels of transthyretin (TTR) are observed in 65 year old sepsis patients and cecal ligand/puncture (CLP) mouse and pig models. It also appears that acute phase response increases with the disease severity. For example, sepsis patients have higher levels of CRP and lower levels of serum amyloid A4 relative to patients with systemic inflammatory response syndrome (SIRS), another precursor to sepsis. Póvoa et al., "C-reactive protein: a valuable marker of sepsis" *Intensive Care Medicine* 28:235-243 (2002); Shen et al., "Sepsis Plasma Protein Profiling with Immunodepletion, Three-Dimensional Liquid Chromatography Tandem Mass Spectrometry, and Spectrum Counting" *Journal of Proteome Research* 5:3154-3160 (2006); Zweigner et al., "High concentrations of lipopolysaccharide-binding protein in serum of patients with severe sepsis or septic shock inhibit the lipopolysaccharide response in human monocytes" *Blood* 98:3800-3808 (2001); Kalenka et al., "Changes in the serum proteome of patients with sepsis and septic shock" *Anesthesia & Analgesia* 103:1522-1526 (2006); Ren et al., "The alterations of mouse plasma proteins during septic development" *Journal of Proteome Research* 6:2812-2821 (2007); Thongboonkerd et al., "Altered plasma proteome during an early phase of peritonitis-induced sepsis" *Clinical Science* 116:721-730 (2009).

In the data presented herein it was observed that eighteen (18) differentially-expressed proteins including, but not limited to, CRP, LBP, A1ACT, and TTR may be involved in acute phase response and the levels in younger adults are consistent with above cited studies. See, FIG. 26. For example, CRP (fold-change YS/YC 3.268±1.070), LBP (2.201±0.502), A1ACT (1.577±0.867), and A1AG (2.033±0.426) have higher concentrations while TTR (0.440±0.094) has lower concentrations in younger adults who developed severe sepsis as compared to those did not. Also evidenced in the present data is that acute phase response also varies depending on patient age. The proteins CRP (0.521±0.221), LBP (0.762±0.321), and A1ACT (0.683±0.183) have lower concentrations in older adults who later developed severe sepsis suggesting that lower expression of these proteins at older age leads to severe sepsis. CRP and LBP have protective effects by neutralizing the toxicity of pathogens, such that decreased expression of these proteins in older patients may help explain higher risk and mortality of severe sepsis. Póvoa et al., "C-reactive protein as a marker of infection in critically ill patients" *Clinical Microbiology and Infection* 11:101-108 (2005); Masiá et al., "Serum concentrations of lipopolysaccharide-binding protein as a biochemical marker to differentiate microbial etiology in patients with community-acquired pneumonia" *Clinical Chemistry* 50:1661-1664 (2004); Tschaikowsky et al., "Lipopolysaccharide-binding protein for monitoring of postoperative sepsis: complemental to C-reactive protein or redundant?" *PLoS ONE* 6:e23615 (2011); and Villar et al., "Serum lipopolysaccharide binding protein levels predict severity of lung injury and mortality in patients with severe sepsis" *PLoS ONE* 4:e6818 (2009).

Both aging and severe sepsis alter the immune system and response to infection. Sadeghi et al., "Phenotypic and functional characteristics of circulating monocytes of elderly persons" *Experimental Gerontology* 34:959-970. Taken together, these results of acute phase response imply that a hypoinflammatory response in older adults may increase risk of severe sepsis, consistent with other literature reports. Welty-Wolf et al., "Proinflammatory cytokines increase in sepsis after anti-adhesion molecule therapy" *Shock* 13:404-409 (2000); and Gustot T., "Multiple organ failure in sepsis: prognosis and role of systemic inflammatory response" *Curr. Opin. Crit. Care* 17:153-159 (2011).

B. Blood Factor Coagulation Pathways

Pro-inflammatory cytokines can also activate the coagulation pathway. Briefly, the activation of a series of coagulation factors cleave prothrombin to thrombin, which in turn converts soluble fibrinogen into fibrin, upon which cross-linked fibrin forms blood clots. In sepsis patients, pro-coagulation overwhelms fibrinolysis (or anti-coagulation) leading to the presence of more blood clots. This has been demonstrated by decreased levels of anti-coagulant proteins (e.g., antithrombin III (ATIII), and heparin cofactor II) and increased levels of pro-coagulant proteins (e.g., fibrinogen, Von Willebrand factor (VWF)) in sepsis patients. Amaral et al., "Coagulation in sepsis" *Intensive Care Medicine* 30:1032-1040 (2004); Soares et al., "Differential proteomics of the plasma of individuals with sepsis caused by *Acinetobacter baumannii*" *Journal of Proteomics* 73:267-278 (2009); Ware et al., "Significance of von Willebrand factor in septic and nonseptic patients with acute lung injury" *American Journal of Respiratory and Critical Care Medicine* 170:766-772 (2004); and Kaspereit et al., "The effect of fibrinogen concentrate administration on coagulation abnormalities in a rat sepsis model" *Blood Coagulation & Fibrinolysis* 15:39-43 (2004).

In the presently disclosed data, elevated levels of fibrinogen alpha chain (2.441±0.579), fibrinogen beta chain (2.102±0.579), fibrinogen gamma chain (2.077±0.720) and VWF (2.047±0.340) were found in younger adults who developed severe sepsis. Fibrinogen has higher concentrations and ATIII has lower concentrations in sepsis. Ren et al., "The alterations of mouse plasma proteins during septic development" *Journal of Proteome Research* 6:2812-2821 (2007); and Soares et al., "Differential proteomics of the plasma of individuals with sepsis caused by *Acinetobacter baumannii*" *Journal of Proteomics* 73:267-278 (2009).

Higher levels of VWF are associated with mortality in sepsis, while higher levels of fibrinogen and VWF may indicate the presence of more blood clots in younger patients, consistent with literature reports, whom developed severe sepsis. Ware et al., "Significance of von Willebrand factor in septic and nonseptic patients with acute lung injury" *American Journal of Respiratory and Critical Care Medicine* 170:766-772 (2004); Kaspereit et al., "The effect of fibrinogen concentrate administration on coagulation abnormalities in a rat sepsis model" *Blood Coagulation & Fibrinolysis* 15:39-43 (2004); van't Veer et al., "Keeping blood clots at bay in sepsis" *Nat Med* 14:606-608 (2008); and Sunder-Plassmann et al., "Disseminated intravascular coagulation and decrease in fibrinogen levels induced by vincristineprednisolone therapy of lymphoid blast crisis of chronic myeloid leukemia" *Ann. Hematol.* 62:169-173 (1991). This notion is further supported by decreased concentrations of ATIII (0.596±0.064) and heparin cofactor 11 (0.707±0.255) in these studies. Interestingly, fibrinogen (0.597±0.129) had lower levels in older adults who developed severe sepsis. Although it is not necessary to understand the mechanism of an invention, it is believed that the presently disclosed proteomic sepsis expression profile indicates that an acute response of reduced coagulation activity may be a contributing factor to higher incidence and mortality of severe sepsis found in older adults.

C. Lipid Metabolism Pathways

Apolipoproteins have been suggested to play a role in liver X receptor/retinoid X receptor (LXR/RXR) activation and atherosclerosis signaling. For example, activated LXR/RXR complex can enhance the process of reverse cholesterol transport and cholesterol efflux, which transfers accumulated cholesterol from the blood vessel walls to the liver for excretion. Larrede et al., "Stimulation of cholesterol efflux by LXR agonists in cholesterol-loaded human macrophages is ABCA1-dependent but ABCG1-independent" *Arteriosclerosis. Thrombosis, and Vascular Biology* 29:1930-1936 (2009); and Zhao et al., "Liver X receptor in cholesterol metabolism" *Journal of Endocrinology* 204:233-240 (2010). Additionally, activated LXR/RXR can reduce the expression of pro-inflammatory cytokines (e.g., IL-6, IL-13) by inhibition of the activity of transcription factor NF-κB. Myhre et al., "Liver X receptor is a key regulator of cytokine release in human monocytes" *Shock* 29:468-474 (2008). Interestingly, acute phase response pathway proteins, which are activated during aging and severe sepsis (supra), can inhibit LXR/RXR activation. Khovidhunkit et al., "Thematic review series: the pathogenesis of atherosclerosis, effects of infection and inflammation on lipid and lipoprotein metabolism mechanisms and consequences to the host" *Journal of Lipid Research* 45:1169-1196 (2004). Failed activation of the LXR/RXR complex may lead to atherosclerosis, which is associated with severe sepsis Brazil, M., "Macrophage LXRs inhibit atherosclerosis" *Nat Rev Drug Discov* 1:840-840 (2002); Joseph et al., "Synthetic LXR ligand inhibits the development of atherosclerosis in mice" *Proceedings of the National Academy of Sciences* 99:7604-7609 (2002); Hackam et al., "Statins and sepsis in patients with cardiovascular disease: a population-based cohort analysis" *Lancet* 367:413-418 (2006); and Podnos et al., "Intra-abdominal Sepsis in Elderly Persons" *Clinical Infectious Diseases* 35:62-68 (2002).

Altered levels of apoliproteins have been reported in sepsis, For example, elevated levels of Apo B-100 and lower concentrations of Apo CIII in response to inflammation. Phetteplace et al., "*Escherichia coli* sepsis increases hepatic apolipoprotein B secretion by inhibiting degradation" 35:1079-1085 (2000); and Lacorte et al., "Repression of apoC-III gene expression by TNFα involves C/EBPδ/NF-IL6β via an IL-1 independent pathway" *FEBS Letters* 415: 217-220 (1997). The data provided herein also shows an increased expression of Apo B-100 (1.523±0.253) and decreased expression of Apo CIII (0.690±0.294) in younger adults who developed severe sepsis. Although it is not necessary to understand the mechanism of an invention, it is believed that these changes may suggest suppressed activation of the LXR/RXR pathway and subsequent higher risk of atherosclerosis in younger adults. Higher levels of Apo E (2.105±0.301) were found in younger adults, however lower levels (0.646±0.170) were detected in older adults. Kattan et al., "Apolipoprotein E-mediated immune regulation in sepsis" *J Immunmol* 181:1399-1408 (2008). Also, higher levels of Apo C1 (2.165±1.022) and lower levels of Apo M (1.438±0.483) were detected in older adults who developed severe sepsis. Apo C1 levels correlate with survivorship in ~25 year old severe sepsis patients and may promote atherosclerosis. Berbée et al., "Plasma apolipoprotein C1 correlates with increased survival in patients with severe sepsis" *Intensive Care Medicine* 34:907-911 (2008); Westerterp et al., "Apolipoprotein C1 aggravates atherosclerosis development in ApoE-knockout mice despite mediating cholesterol efflux from macrophages" *Atherosclerosis* 195: e9-e16 (2007); and Westerterp et al., "Apolipoprotein C-1 is crucially involved in lipopolysaccharide-induced atherosclerosis development in apolipoprotein E-knockout mice" *Circulation* 116:2173-2181 (2007). Apo M has also been reported to have higher concentrations in severe sepsis patients and contributes to the anti-inflammatory response in sepsis. Christoffersen et al., "Apolipoprotein M—a new biomarker in sepsis" *Critical Care* 16:126 (2012); and Kumaraswamy et al., "Decreased plasma concentrations of apolipoprotein M in sepsis and systemic inflammatory response syndromes" *Crit Care* 16:R60 (2012). Although it is not necessary to understand the mechanism of an invention, it is believed that higher levels of Apo M in older adults who developed severe sepsis suggest that these patients have a reduced inflammatory state during acute response. It is further believed that lipid metabolism is altered in these studies points to atherosclerosis as a contributing factor of severe sepsis incidence.

D. Interleukin (IL) Pathways

Pathways involved in IL-12 and IL-6 signaling were identified in the proteomic sepsis expression provide that support observations of their involvement in hypoinflammatory response in older adults. See, Table 7. Diefenbach et al., "Requirement for type 2 NO synthase for IL-12 signaling in innate immunity:" *Science* 284:951-955 (1999).

E. Nitric Oxide/Reactive Oxygen Species Pathways

Pathways of differentially-expressed proteins were identified that involve the production of nitric oxide (NO) and reactive oxygen species (ROS) (i.e., for example, retinol binding protein 1, lysozyme C and/or clusterin). Enhanced production of nitric oxide (NO) and reactive oxygen species (ROS) in macrophages has been previously reported in aging and sepsis which support elevated oxidative stress in the elderly and severe sepsis patients. Kolls J. K., "Oxidative stress in sepsis: a redox redux" *The Journal of Clinical Investigation* 116:860-863 (2006); Berr, C., "Cognitive impairment and oxidative stress in the elderly: Results of epidemiological studies" *BioFactors* 13:205-209 (2000); Karolkiewicz et al., "Oxidative stress and antioxidant defense system in healthy, elderly men: relationship to physical activity" *The Aging Male* 6:100-105 (2003); and Macdonald et al., "Oxidative stress and gene expression in sepsis" *British Journal of Anaesthesia* 90:221-232 (2003).

In one embodiment, the present invention contemplates measuring immune-related oxidative stress. In one embodiment, the present invention contemplates determining the effects of adriamycin treatment on the proteome. In one embodiment, the present invention contemplates establishing quantitative plasma workflow for age-related sepsis outcomes.

F. Retinoid X Receptor Pathways

Different biological pathways have been identified to be associated with the age-related risk of severe sepsis among CAP patients (supra). Among these, four pathways related to retinoid X receptor (RXR) are identified: liver X receptor (LXR)/RXR activation, farnesoid X receptor (FXR)/RXR activation, LPS/IL-1 mediated inhibition of RXR function, and peroxisome proliferator-activated receptor alpha (PPARα)/RXRα activation.

RXR has been reported to play a role in the nuclear receptor superfamily because it forms heterodimers with many other nuclear receptors and therefore are involved in a variety of physiological processes including immune response. Mangelsdorf et al., *Cell* 83:841 (1995). For example, in innate immune systems, activation of RXR has been shown to prevent the apoptosis and inflammatory response of macrophages. Núñez et al., *Proceedings of the National Academy of Sciences* (2010). In the adaptive immune system, RXR has been reported to regulate the differentiation of T-cells into regulatory or helper T-cells. Takeuchi et al., "The Journal of Immunology" 191:3725 (2013). Knockout of RXR gene has been reported to result in diminished proliferation and increased apoptosis in T-cells. Stephensen et al., *Immunology* 121:484 (2007). In addition, RXR has been reported to protect human endothelial cells from oxidative stress induced by high-dose glucose. Chai et al., *Free Radical Biology and Medicine* 44:1334 (2008).

In sepsis, infection-induced damage to liver has been reported to be reduced by the activation of RXR. Chen et al., *Shock* 28:65 (2007). However, the effects of RXR on T-cells in septic infection have not examined yet. Although it is not necessary to understand the mechanism of an invention, it is believed that activation of RXR may protect T-cells from oxidative stress induced by infection (e.g., LPS stimulation). To test this hypothesis, CD4+ T-cells were isolated from the spleen harvested from wild type mice at 6-month old. These cells were cultured in the cell medium with or without LPS-stimulation for 24 hours. LPS-stimulated CD4+ T-cells have increased levels of oxidative stress compared to the controls. Increased levels of RXR are also observed in LPS-stimulated CD4+ T-cells (data not shown). These findings suggest that increased levels of RXR might be responsible for the increased protein expression induced by LPS in CD4+ T-cells. For example, gene for Apo E is one of the targets for RXR. Sureda et al., *Current Pharmaceutical Design* 17:230 (2011). The data presented herein showing an increased plasma concentration of ApoE in young severe sepsis patients (e.g., 55-65 years old) is consistent with the above suggestion, as increased ApoE may be mediated by RXR activation.

IV. Sepsis Treatment: Current State of the Art

Conventional sepsis treatment is generally supportive usually requiring intravenous antibiotic administration in a hospital or other clinical setting. Further, oxygen administration with intravenous fluid replacement is common. Secondary treatment may include, but are not limited to, medications that increase blood pressure, dialysis and/or mechanical ventilation. Although it is not necessary to understand the mechanism of an invention, it is believed that the data disclosed herein suggest that effective new sepsis therapies may be directed at alleviating the phenomenon of immunosensecence.

A broad-spectrum antimicrobial treatment is usually recommended for sepsis therapy that is initiated as soon as possible after diagnosis. This is because early and adequate antimicrobial therapy has been reported to reduced mortality rates. American Thoracic Society, "Infectious Diseases Society of America. Guidelines for the management of adults with hospital-acquired, ventilator-associated, and healthcare-associated pneumonia" *American Journal Respiratory and Critical Care Medicine* 171(4):388-416 (2005); Harbarth et al., "Inappropriate initial antimicrobial therapy and its effect on survival in a clinical trial of immunomodulating therapy for severe sepsis" *American Journal of Medicine* 115(7):529-535 (2003); Kumar et al., "Duration of hypotension before initiation of effective antimicrobial therapy is the critical determinant of survival in human septic shock" *Critical Care Medicine* 34(6):1589-1596 (2006); Micek et al., "*Pseudomonas aeruginosa* bloodstream infection: importance of appropriate initial antimicrobial treatment" *Antimicrobial Agents Chemotherapy* 49(4): 1306-1311 (2005); and Proulx et al., "Delays in the administration of antibiotics are associated with mortality from adult acute bacterial meningitis" *Quarterly Journal of Medicine* 98(4): 291-298 (2005). Unfortunately this approach can expose individuals to an overuse of antimicrobials. This is mainly because of emerging resistant pathogens, which increase the risk of inappropriate therapy. Leone et al., "Ventilator-associated pneumonia: Breaking the vicious circle of antibiotic overuse" *Critical Care Medicine* 35(2):379-385 (2007); and Niederman et al., De-escalation therapy in ventilator-associated pneumonia. Current Opinion in Critical Care 12(5):425-427 (2006).

Standard antimicrobial therapy comprises the maintenance of an initial empirical broad-spectrum antimicrobial therapy independent of whether the antimicrobial therapy was a combination or a single agent. Alternatively, de-escalation antimicrobial therapy comprises changing an initially appropriate antimicrobial therapy from an empirical broad-spectrum characteristic to a narrower-spectrum one by either changing the antimicrobial agent or by discontinuing an eventual antimicrobial combination, or both, according to culture results or clinical conditions.

In one embodiment, the present invention contemplates a method for treating a sepsis patient using a therapy including, but not limited to, fluid therapy, vasopressor therapy, inotropic support, antibiotics, albumin and red blood cell transfusion in patients with sepsis. In one embodiment, the vasopressor comprises norepinephrine and/or dopamine. Ibsen et al., "Perioperative treatment of patients with sepsis" *Curr Opin Anaesthesiol.* 26(3):348-353 (2013).

As discussed above, the clinical process of severe sepsis may be characterized by extreme inflammation interlinked with potent stimulation of the coagulation cascade often followed by a state of relative immune paralysis. In some embodiments, the present invention contemplates treating a patient with sepsis with a therapy directed at least one inflammatory cascade step. In one embodiment, the cascade step comprises modulating inflammatory mediators eliciting the immune response. In one embodiment, the cascade step comprises altering the host's immune response in both a stimulatory and depressive manner. In one embodiment, the cascade step comprises taming an overexuberant coagulation response triggered by a coagulation-inflammation cycle. Bernard et al., "The Immune Response: Targets for the Treatment of Severe Sepsis" *Int J Inflam.*, epub 2012; 697592 (2012).

A. Antibiotic Therapy

In one embodiment, the present invention contemplates a method of treating a sepsis patient by the administration of a broad-spectrum antibiotic. In one embodiment, a broad spectrum antibiotic includes, but is not limited to, ampicillin, amoxicillin, carbapenems, imipenem, meropenem, ertapenem, piperacillin, tazobactam, levofloxacin, gatifloxacin, moxifloxacin, ciprofloxacin, streptomycin, tetracycline, chloramphenicol and/or ticarcillin. Although it is not necessary to understand the mechanism of an invention a broad-spectrum antibiotic is believed to be an antibiotic that acts against a wide range of disease-causing bacteria. For example, a broad-spectrum antibiotic acts against both Gram-positive and Gram-negative bacteria, in contrast to a narrow-spectrum antibiotic, which is effective against specific families of bacteria.

Early, appropriate antibiotic therapy is usually recommended for the treatment of the septicemic patient. The degree of organ dysfunction, underlying medical conditions, and physiologic abnormalities are prognostic factors but are not necessarily prognostic for initial antibiotic selection. Initial empiric therapy should be directed against the resident flora of the organ, which is primarily involved in the infectious process. Blood cultures should be obtained in all patients for the initiation of antibiotic therapy, and methods should be employed for the early detection of septicemia. Other conditions that mimic sepsis, e.g., pseudosepsis, should be ruled out initially to avoid an incorrect diagnosis and unnecessary antibiotic therapy. Monotherapy and fully recommended doses of antimicrobial drugs delivered by the intravenous route as soon as the diagnosis is established remain the cornerstone of therapy in treating the septic patient. Monotherapy with an antibiotic of the appropriate spectrum is more than adequate to treat the great majority of septicemic patients. Double-drug therapy is recommended to treat febrile leukopenic compromised hosts, serious *P. aeruginosa* infections, and selected cases of intra-abdominal sepsis. Cunha B A., "Antibiotic treatment of sepsis" *Med Clin North Am.* 1995 May; 79(3):551-558.

Antibiotic selection made within the first hour of recognition of severe sepsis and septic shock has been shown to decrease mortality. Methods of determining what antibiotics should be prescribed and identification of factors influencing ineffective antibiotic coverage in patients with severe sepsis or septic shock have been reported. For example, a retrospective review of emergency department (ED) patients admitted to an intensive care unit (ICU) over a 12-month period with a culture-positive diagnosis of either severe sepsis or septic shock was performed. Appropriate antibiotic therapy was defined as effective coverage of the offending organism based on final culture results. Of the 1400 patients admitted to the ICU, 137 patients were culture positive and met the criteria for severe sepsis or septic shock. Effective antibiotic coverage was prescribed by emergency physicians in 82% (95% confidence interval [C1]0.74-0.88) of cases. Of the 25 patients who received ineffective antibiotics, the majority had infections caused by resistant Gram-negative organisms. Health care-associated pneumonia guidelines were applied to all patients, regardless of the source of infection, and were 100% sensitive (95% CI 0.93-1.0) for selecting patients who had infections caused by highly resistant organisms. Emergency physicians achieved 82% effective antibiotic coverage in patients with severe sepsis or septic shock. The gap seems to be in coverage of highly resistant Gram-negative organisms. An alternative approach to antibiotic prescription, utilizing a set of guidelines for community- and health care-associated infections, was found to be 100% sensitive in selecting patients who had infections caused by the more resistant organisms. Capp et al., "Effective antibiotic treatment prescribed by emergency physicians in patients admitted to the intensive care unit with severe sepsis or septic shock: where is the gap?" *J Emerg Med.* 2011 41(6):573-580.

Antibiotics are generally used to treat bacterial sepsis because it is believed that they reduce the bacterial burden. The impact of bacterial resistance has recently been studied and found to be important in a range of conditions. Resistance to antibiotics can be defined genotypically, phenotypically and clinically through pharmacokinetic/pharmacodynamic studies and their correlations with clinical outcomes. Although the kinetics of antibiotics has been shown to be favourably altered in sepsis, a range of studies in sepsis has revealed that for most pathogens resistance contributes to significant increases in mortality. This has been demonstrated in bacteraemia, including community- and hospital-acquired infection, and with bacteraemia caused by vancomycin-resistant enterococci, methicillin-resistant staphylococci and extended-spectrum producing Gram-negative bacteria. Significant mortality increases have also been seen with ventilator-associated pneumonia and serious infections requiring admission to intensive care. Gentotypic and phenotypic resistance in coagulase-negative staphylococci causing bacteraemia, and in invasive pneumococcal disease has not shown differences in mortality. In the latter case, dosage regimens have to date been adequate to overcome laboratory-defined resistance. Early indications are that de-escalating therapy from broad-spectrum initial coverage after results of cultures and susceptibility tests become available does not jeopardize outcomes, and further prospective studies are warranted. There is now convincing evidence that broad-spectrum initial therapy to cover the likely pathogens and their resistances pending culture results is useful in sepsis to minimize adverse outcomes. Turnidge J., "Impact of antibiotic resistance on the treatment of sepsis" *Scand J Infect Dis.* 2003; 35(9):677-682.

B. Inflammatory Mediator Inhibitor Therapy

Decades ago, unfruitful attempts were made to create antibodies with the potential to bind and to prevent inflammatory bacterial components from triggering the hyperinflammatory response of sepsis. Lipopolysaccharide (LPS), a primary mediator in gram-negative sepsis, was the target of researchers as early as the 1980s. Clinicians tested E5 and HA1A, both anti-LPS monoclonal antibodies, as treatments for septic patients. In initial studies, both antibodies showed encouraging results in small subsets of patients. Fink showed improvement in mortality in patients with culture-proven gram-negative bacteremia when treated with HA1A. Fink M P. "Adoptive immunotherapy of gram-negative sepsis: use of monoclonal antibodies to lipopolysaccharide" *Critical Care Medicine* 21 (supplement 2):S32-S39 (1993). Ziegler et al. showed improved mortality with the use of HA-1A therapy in 200 patients with proven gram-negative sepsis. The 343 septic patients without culture proven gram-negative bacteremia showed no treatment benefit. Ziegler et al., "Treatment of gram-negative bacteremia and septic shock with HA-1A human monoclonal antibody against endotoxin. A randomized, double-blind, placebo-controlled trial" *New England Journal of Medicine.* 1991; 324(7):429-436. Greenman et al. evaluated E5 in 1991 and showed improved mortality and resolution of organ failure in a subgroup of patients not in shock at the time of study entry. Greenman et al., "A controlled clinical trial of E5 murine monoclonal IgM antibody to endotoxin in the treatment of gram-negative sepsis" *Journal of the American Medical Association.* 1991; 266(8): 1097-1102. In a follow-up study, Bone et al. evaluated 530 patients with suspected or proven gram-negative sepsis and did not find a difference in mortality but demonstrated improvement of organ failure resolution in those treated with E5 as well as prevention of adult respiratory distress syndrome and central nervous system organ failure. Bone et al., "A second large controlled clinical study of E5, a monoclonal antibody to endotoxin: results of a prospective, multicenter, randomized, controlled trial" *Critical Care Medicine.* 1995; 23(6):994-1006. Unfortunately, further studies of these therapies in larger clinical trials including more than 1,000 patients each were unable to confirm efficacy. Alejandria et al., "Intravenous immunoglobulin for treating sepsis and septic shock" *Cochrane Database of Systematic Reviews.* 2002; (1):p.CD001090; Angus et al., "E5 murine monoclonal antiendotoxin antibody in gram-negative sepsis: a randomized controlled trial" *Journal of the American Medical Association.* 2000; 283 (13): 1723-1730; McCloskey et al., "Treatment of septic shock with human monoclonal antibody HA-1A: a randomized, double-blind, placebo-controlled trial" *Annals of Internal Medicine.* 1994; 21(1): 1-5.

More recently, this approach has been revisited with the concept of inhibiting toll-like receptor 4 (TLR-4) which is expressed on the surface of immune cells and binds LPS and other ligands to initiate an intracellular signaling cascade resulting in the release of proinflammatory cytokines. Salomao et al., "TLR signaling pathway in patients with sepsis" *Shock,* 2008; 30 (supplement 1):73-77. The therapy, TAK-242, functions as a signal inhibitor of the TLR-4 pathway acting after TLR-4 binds with LPS. In septic animal models an improved survival associated with decreased levels of inflammatory cytokines has been shown with the use of this therapy. Furthermore, its use in healthy volunteers prior to instillation of LPS also resulted in decreased levels of inflammatory cytokines when these patients were given an LPS challenge. In 2010, Rice et al. evaluated TAK-242 in a randomized, placebo-controlled trial of patients with severe sepsis and shock or respiratory failure. High-dose and low-dose treatment regiments were compared to placebo with primary endpoints of change in IL-6 level and 28-day mortality rate. This trial was terminated after enrollment of 274 patients failed to show suppression of IL-6 levels. Evaluation of the treated patients showed no difference in 28-day mortality compared to placebo, however, there was a trend toward improved survival in those with both shock and respiratory failure who were in the higher treatment dose cohort. Rice et al., "A randomized, double-blind, placebo-controlled trial of TAK-242 for the treatment of severe sepsis" *Critical Care Medicine.* 2010; 38(8):1685-1694. It may be that this therapy could be effective in patients with a higher severity of illness, as suggested by the trend towards improved survival of the patients with both respiratory failure and shock. Furthermore, the mean time from onset of shock or respiratory failure to initiation of TAK-242 therapy was 19 hours. The dynamic nature of the immune response has been well described and it could be postulated that the delay of 19 hours is too long for the treatment to have the ability to suppress the immune response.

C. Steroid Therapy

Steroids are believed to act early in the inflammatory cascade eliciting a wide range of effects via broad suppression of the immune system and are hypothesized to provide benefit as a supplementary treatment of sepsis. Steroids function by inhibiting production of compounds including, but not limited to, proinflammatory cytokines (i.e., for example, TNF-α, IL-1, IL-2, IL-6, and IFN-gamma), chemokines, bradykinins, and eicosanoids. Simultaneously, they may increase anti-inflammatory mediators (IL-10, IL-1 receptor antagonists, and TNF receptor antagonists), inhibit inducible nitric oxide synthase, decrease migration of inflammatory cells to sites of inflammation, and reduce the function of inflammatory cells. Rice et al., "Therapeutic intervention and targets for sepsis" *Annual Review of Medicine.* 2005; 56:225-248. It is further postulated that steroids increase the expression of adrenergic receptors in the vasculature. These receptors are downregulated in septic shock and, theoretically, increasing their expression allows the vasculature to respond to the high levels of circulating cortisol. Hotchkiss et al., "The pathophysiology and treatment of sepsis" *New England Journal of Medicine.* 2003; 348(2): 138-150.

Initially, studies were done using high-dose steroids (e.g., 30 mg/kg methylprednisolone) with the goal of broad suppression of the body's overreactive inflammatory response. Annane et al., "Corticosteroids in the treatment of severe sepsis and septic shock in adults: a systematic review" *Journal of the American Medical Association.* 2009; 301 (22):2362-2375; Batzofin et al., The use of steroids in the treatment of severe sepsis and septic shock. Best Practice & Research. 2011; 25(5):735-743; Cronin et al., "Corticosteroid treatment for sepsis: a critical appraisal and meta-analysis of the literature" *Critical Care Medicine.* 1995; 23(8): 1430-1439. These studies failed to show benefit and even showed a trend towards harm including increased mortality due to secondary infections in those treated with steroids, thus, causing steroid therapy use to decrease in the early 1990s. The use of steroids was revived in the mid 1990s with the target of treating relative adrenal insufficiency with the use of replacement, low-dose glucocorticoids. The treatment with low-dose steroids is thought to improve vascular response to endogenous and exogenous catecholamines via the upregulation of adrenergic receptors in the vasculature. While avoiding the substantial immune system blockade, this lower dose is thought to maintain some anti-inflammatory effects via preventing release of proinflammatory cytokines and activation of endothelial cells and neutrophils to decrease sepsis triggered clotting disorders.

Small studies done in the late 1990s showed trends toward improvement in hypotension and mortality with the low-dose steroid treatment strategy. However, these studies were underpowered to detect clinically significant effects. More recently, two large randomized, controlled trials have been published that further evaluated the effectiveness of steroid therapy. In 2002, a study completed by Annane et al. evaluated 300 patients with septic shock and showed improvement of refractory hypotension and a decrease in absolute mortality in patients with relative adrenal insufficiency treated with 7 days of hydrocortisone and fludrocortisone. This study also showed that adrenal-sufficient patients as defined as displaying a response to ACTH gained no benefit and trended towards harm from glucocorticoids. Annane et al., "Effect of treatment with low doses of hydrocortisone and fludrocortisone on mortality in patients with septic shock" *Journal of the American Medical Association.* 2002; 288(7):862-871.

Subsequently, the CORTICUS study published in 2008 by Sprung et al. compared the treatment of 499 septic patients with 11 days of hydrocortisone versus placebo. Contrary to the Annane study, the CORTICUS trial failed to show an improvement in mortality or reversal of shock in treated patients, regardless of ACTH response. They did, however, show a faster resolution of shock in those patients who had shock resolution and were treated with hydrocortisone. Interestingly, they did show an increased incidence of superinfection in those treated with steroids. Sprung et al., "Hydrocortisone therapy for patients with septic shock" *New England Journal of Medicine.* 2008; 358(2):111-124. The differences in the outcomes of these trials may be linked to several key differences between them. The populations studied included different timing of patient enrollment. The Annane study took patients up to 8 hours after onset of shock while the CORTICUS study extended their enrollment up to 72 hours after the onset of shock. Furthermore, the CORTICUS trial included all patients in shock while the Annane study restricted their study to only those who were both fluid and vasopressor refractory. Similarly, the patients in the Annane study were significantly more ill at baseline with a higher SAPS score and a higher mortality rate in the placebo groups than the CORTICUS trial (65% Annane trial versus 32% CORTICUS trial). It could be postulated that their conflicting results are a product of their differing patient populations as the Annane study evaluated a group of patients with a higher degree of illness and more refractory shock.

Furthermore, the Annane and CORTICUS trials differed regarding the utility of the ACTH stimulation test. The Annane study showed that ACTH nonresponders were more likely to benefit from steroid therapy while the CORTICUS trial failed to replicate this finding. Given the challenges of measuring cortisol levels and the finding that the Annane trial showed an overall trend toward benefit of steroid therapy, regardless of ACTH responsiveness, the 2008 Surviving Sepsis Guidelines recommended that the ACTH stimulation test not to be used as a tool to guide the use of steroid therapy. Known side effects of steroids including hyperglycemia, gastrointestinal bleeding, myopathy, and secondary infection have tempered the enthusiasm for steroid use. The CORTICUS trial, showing no efficacy of steroids reinforced these reservations when it also demonstrated an increase in episodes of superinfection with new sepsis and septic shock in those treated with steroids.

Currently, the adult literature has not developed a standard of care in regards to steroid therapy. The Surviving Sepsis Guidelines recommend the use of steroids only in fluid and vasopressor refractory shock and do not recommend the use of the ACTH stimulation test based on low-grade and moderate-grade evidence, respectively. Furthermore, they advise tapering the steroids when the state of shock resolves. Less data exists in regards to the pediatric population and the Surviving Sepsis Guidelines base recommendations on a retrospective review, done by Markovitz et al., "A retrospective cohort study of prognostic factors associated with outcome in pediatric severe sepsis: what is the role of steroids?" *Pediatric Critical Care Medicine.* 2005; 6(3): 270-274. Consequently, it is possible that corticosteroid use in children with severe sepsis represents an independent predictor of mortality. However, the nature of the study design does not allow for causal inference and the Surviving Sepsis Guidelines cite a weak recommendation based on low-grade evidence for the use of hydrocortisone only in children with catecholamine resistant shock and suspected or proven adrenal insufficiency. Ideally, what is needed is a better means of determining the population of septic patients which have the best chance to benefit from steroid treatment while having the least risk of harm due to the side effects of the therapy.

D. Proinflammatory Cytokine Inhibitor Therapy

Knowledge of the inflammatory cascade and, more specifically, proinflammatory cytokines has allowed specific targets for immunosuppression including TNF-α and IL-1. TNF-α injection into animals has been shown to trigger a sepsis-like syndrome including hypotension, activation of the clotting cascade, significant organ dysfunction, and even death. Furthermore, increasing and persistently elevated levels of TNF-α are associated with nonsurvival in humans. Qiu et al., "The evolving experience with therapeutic TNF inhibition in sepsis: considering the potential influence of risk of death" *Expert Opinion on Investigational Drugs.* 2011; 20(11): 1555-1564; and Reinhart et al., "Anti-tumor necrosis factor therapy in sepsis: update on clinical trials and lessons learned" *Critical Care Medicine.* 2001; 29 (supplement 7):S121-S125.

Downstream effects of TNF-α include augmentation of the inflammatory cascade via elevation of multiple cytokine levels and upregulation of adhesion molecules on leukocytes, platelets, and endothelial cells. TNF-α also stimulates the coagulation system via activation of thrombotic and fibrinolytic pathways. Despite the deleterious effects of this overstimulation, it is evident that TNF-α plays a crucial role in the immune system because blockage of its activity in animal models has led to a worsened ability of the animal's immune system to clear microbes. Due to its pivotal position in the inflammatory and coagulation systems that are known to cause the demise in sepsis, TNF-α has been targeted as a treatment of sepsis in many clinical trials. Although no trial has succeeded in showing an overall improvement using this therapy, several studies have identified populations and/or characteristics of these patients that may direct future trials.

The first large trial, NORASEPT, was done by Abraham et al. in 1995 and included 900 patients with sepsis or septic shock. The NORASEPT trial evaluated an anti-TNF-α monoclonal antibody and failed to show an overall mortality benefit. However, the subset of patients with septic shock showed a significant improvement in mortality 3 days after drug infusion. In following the patients further, the 28-day mortality continued to show a trend towards improvement but was no longer significant. Abraham et al., "Efficacy and safety of monoclonal antibody to human tumor necrosis factor α in patients with sepsis syndrome: a randomized, controlled, double-blind, multicenter clinical trial" *Journal of the American Medical Association.* 1995; 273(12):934-941. The INTERSEPT study, published in 1996, focused on evaluation of 420 patients with septic shock. This study showed more rapid reversal of shock and fewer patients with at least one organ failure in survivors who were treated with the anti-TNF-α monoclonal antibody as compared with the placebo group. However, this trial failed to show a difference in mortality. Cohen et al., "INTERSEPT: an international, multicenter, placebo-controlled trial of monoclonal antibody to human tumor necrosis factor-α in patients with sepsis" *Critical Care Medicine.* 1996; 24(9):1431-1440. This drug was tested in a third trial, NORASEPT II, which also failed to show an improvement in mortality. Abraham et al., "Double-blind randomised controlled trial of monoclonal antibody to human tumour necrosis factor in treatment of septic shock" *The Lancet.* 1998; 351(9107):929-933.

A trial of an anti-TNF-α antibody fragment, afelimomab, was done by Reinhart et al. and published in 1996 that suggested a benefit of treatment in patients with baseline elevation of IL-6. Reinhart et al., "Assessment of the safety and efficacy of the monoclonal anti-tumor necrosis factor antibody-fragment, MAK 195 F, in patients with sepsis and septic shock: a multicenter, randomized, placebo-controlled, dose-ranging study" *Critical Care Medicine.* 1996; 24(5):733-742. Physiologically, this association is plausible as IL-6 levels are considered to be a surrogate for overall TNF-α activity due to the longer half-life of IL-6 compared to the rapidly cleared TNF-α. This hypothesis was tested in a prospective, randomized placebo-controlled trial, the RAMSES study of 446 patients with elevated IL-6 levels. It showed a nonsignificant trend towards improved survival in those treated with afelimomab. Reinhart et al., "Randomized, placebo-controlled trial of the anti-tumor necrosis factor antibody fragment afelimomab in hyperinflammatory response during severe sepsis: the RAMSES study" *Critical Care Medicine.* 2001; 29(4):765-769. A later study, the MONARCS trial, tested the same antibody fragment in 998 patients with elevated IL-6 levels and found a trend towards improved survival in treated patients as compared to placebo. The risk-adjusted reduction in mortality was 5.8% and corresponded to a relative risk reduction for mortality of 11.9%. This study also found a greater reduction in IL-6 levels and multiorgan dysfunction score in those treated with afelimomab. The results are also encouraging because patients with higher IL-6 levels had significantly higher mortality rates in the placebo group than those with lower IL-6 levels. Thus, this showed that afelimomab had a greater effect in patients at higher risk of mortality. Panacek et al., "Efficacy and safety of the monoclonal anti-tumor necrosis factor antibody F(ab')2 fragment afelimomab in patients with severe sepsis and elevated interleukin-6 levels" *Critical Care Medicine.* 2004; 32(11):2173-2182. In a similar investigation, cytofab, a preparation of polyclonal ovine anti-TNF Fab IgG fragments, was tested in a phase 11 placebo-controlled randomized clinical trial in 81 septic patients with shock or two organ dysfunctions. While this study did not show a difference in mortality, the investigators were able to show an increase in ventilator-free days, ICU-free days, and a decrease in serum and BAL levels of TNF-α and downstream effects on IL-6 in patients treated with CytoFab. Rice et al., "Safety and efficacy of affinity-purified, anti-tumor necrosis factor-α, ovine fab for injection (CytoFab) in severe sepsis" *Critical Care Medicine.* 2006; 34(9):2271-2281. The persistent trends toward improved survival in the above studies are encouraging that some patients have the ability to benefit from immunotherapies. The difficulty lies in determining which patients are most likely to benefit.

With a similar mechanism of action, IL-1 is also a target of immunotherapies. This proinflammatory cytokine works together with TNF-α to propagate the hyperimmune response of sepsis. Macrophages and other cells naturally produce IL-1 receptor antagonist (IL-1ra) in response to IL-1, endotoxin, and various other microbial elements. The IL-1ra reversibly binds and competitively inhibits IL-1 receptors. Fisher et al., "Recombinant human interleukin 1 receptor antagonist in the treatment of patients with sepsis syndrome: results from a randomized, double-blind, placebo-controlled trial" *Journal of the American Medical Association.* 1994; 271(23):1836-1843. In 1994, Fisher et al. published a study evaluating the use of IL-1ra in the treatment of 893 patients with sepsis. This study failed to show an overall increase in survival in those treated as compared to placebo. However, retrospective and secondary analyses identified a trend of increased survival among patients with sepsis as well as an organ dysfunction and/or a predicted risk of mortality ≥24%. Subsequently, Opal et al. published a trial in 1997 focusing on IL-1ra treatment in patients with severe sepsis and/or septic shock. Disappointingly, this study was halted when just over half of the proposed enrollment was completed and analysis revealed a low likelihood of showing a statistical difference in their primary endpoint, 28-day mortality. Secondary endpoints showed that those patients treated with IL-1ra displayed a nonsignificant trend towards improvement of organ dysfunction. The authors postulate that they may have had greater success if they were able to identify a more homogenous population. They were also concerned that their treatment was unable to maintain the necessary 100-10,000 fold excess of IL-1ra relative to IL-1 as it is known that stimulation of as few as 5% of the IL-1 receptors triggers an inflammatory response. Opal et al., "Confirmatory interleukin-1 receptor antagonist trial in severe sepsis: a phase 111, randomized, double-blind, placebo-controlled, multicenter trial" *Critical Care Medicine.* 1997; 25(7):1115-1124. Perhaps further evaluation of this drug with the monitoring of levels to ensure complete E. Statin Therapy It is believed that there are many ways which statins have the ability to affect the immune response in sepsis, however, the exact mechanism of their action is unknown. Statins can inhibit the reduction of hydroxymethyl-glutaryl-CoA to mevalonate which plays a role in synthesis of bile acids, some steroid hormones, and vitamin D. Statins may inhibit various other pathways involved in pathophysiology of sepsis including inhibition of the production of cyclo-oxygenase-2 protein, biosynthesis of ubiquinone which functions in the electron transport chain of mitochondria, heme-A used in oxygen transport, and prenylation of small G proteins. It is likely that the alteration of the G-protein pathways has the most influential effect as this significantly alters inflammatory cell activation and protein production. Among other proteins, it is known to inhibit the production of subunits necessary for the GTP binding protein Rho. This inhibition has the downstream effect of production of a decreased amount of inflammatory cytokines such as IL-6 and IL-1. Furthermore, HMGCoA-reductase also induces caspase-dependent apoptosis in smooth muscle cells that may result in less inflammation due to avoidance of necrotic cell death. Bernard G R., "Statins for acutely hospitalized patients: randomized controlled trials are long overdue" *Critical Care.* 2010; 14(2):p. 141.

Data from prospective, randomized-controlled trials evaluating the use of statin therapy in sepsis is lacking. However, multiple observational studies show encouraging effects. A large cohort study of more than 12,000 critically ill patients was published by Christensen et al. in 2010. Results showed that patients on statin therapy immediately prior to ICU admission had a decreased risk of mortality within 30 days and up to 1 year after ICU admission. Given the design of this study, the authors are unable to infer causation but the results stimulate excitement for further evaluation of the effects of statin use. Christensen et al., "Preadmission statin use and one-year mortality among patients in intensive care—a cohort study" *Critical Care.* 2010; 14(2):p. R29 A large meta-analysis done by Bjorkhem-Bergrnan et al, published in 2010, evaluated the potential use of statin therapy in bacterial infection. It showed that patients on statin therapy seemed to have better outcomes including decreased mortality. However, when the 15 observational studies were adjusted for publication bias the association failed to reach statistical significance. Björkhem-Bergman et al., "Statin treatment and mortality in bacterial infections—a systematic review and meta-analysis" *PloS one.* 2010; 5(5):p. e10702. During that same year, Janda et al. focused the evaluation further when they published a meta-analysis evaluating statin therapy in severe infections and sepsis. This study included 20 trials, mostly cohort studies and one randomized-controlled trial that demonstrated a protective effect associated with statin use. The positive outcomes evaluated included 30-day mortality, in-hospital mortality, pneumonia-related mortality, bacteremia-related mortality, sepsis-related mortality, and mixed infection related morality. Again, this study was limited due to the inclusion of mostly cohort studies and significant heterogeneity of trials. Janda et al., "The effect of statins on mortality from severe infections and sepsis: a systematic review and meta-analysis" *Journal of Critical Care.* 2010; 25(4):656-e7. The one randomized controlled trial in this data set was completed by Tseng et al. and included 80 patients with aneurysmal subarachnoid hemorrhages. While this study did show an improvement in sepsis-associated mortality, it cautioned that this finding was a secondary outcome. Tseng et al., "Effects of acute pravastatin treatment on intensity of rescue therapy, length of inpatient stay, and 6-month outcome in patients after aneurysmal subarachnoid hemorrhage" *Stroke.* 2007; 38(5):1545-1550. Due to the promising effects of statins, both based on physiologic knowledge and on the current observational data, phase II and phase III studies are currently in progress to evaluate the role of statins in the treatment of sepsis.

F. Coagulation Cascade Inhibitor Therapy

The extreme activation of the inflammatory system in severe sepsis is accompanied by a potentially equal stimulation of the coagulation system. From an adaptive perspective, this interaction is logical as the activation of the coagulation system can be envisioned as an effort to isolate the infection with the goal of limiting its spread throughout the body.

Various steps of the coagulation pathway have been targeted in the treatment of sepsis. Tissue factor (TF), a cell surface receptor whose expression by endothelial cells and monocytes occurs in the presence of inflammatory mediators, acts to initiate the extrinsic coagulation pathway. A TF inhibitor was tested in the Phase III trial, OPTIMIST, evaluating its use in 1,754 patients with severe sepsis and this trial failed to show an improvement in mortality. More concerning, it showed a trend towards harm in those treated concurrently with heparin. Abraham et al., "Efficacy and safety of tifacogin (recombinant tissue factor pathway inhibitor) in severe sepsis: a randomized controlled trial" *Journal of the American Medical Association.* 2003; 290(2): 238-247. Similarly, antithrombin III (AT III), an anticoagulant, was the subject of sepsis therapy as well due to the finding of decreased AT III levels in severe sepsis and the hypothesis that this deficiency contributes to the hypercoagulation pathophysiology in sepsis. Multiple small studies published in the 1990s showed promising results. However, in a phase II trial of 2,314 septic patients, they were unable to show a difference in overall mortality. However, in subgroup analysis, patients not treated concomitantly with heparin showed a significant decrease in mortality at 90 days while those treated with heparin showed a significantly increased risk of bleeding. Warren et al., "Caring for the critically ill patient. High-dose antithrombin III in severe sepsis: a randomized controlled trial" *Journal of the American Medical Association.* 2001; 286(15): 1869-1878. Future investigation of AT III as a treatment for sepsis will need to carefully select their target population to ensure minimal risks for bleeding.

To date, the only drug that has been approved for the treatment of severe sepsis is recombinant human activated protein C (rhaPC). It was investigated due to its anti-apoptotic, anti-inflammatory, and anticoagulant effects. It acts via inhibition of factors Va and VIIIa which results in the prevention of thrombin generation. Downstream, this decreases inflammation by reducing mast cell degranulation, platelet activation, and neutrophil recruitment. Bernard et al., "Efficacy and safety of recombinant human activated protein C for severe sepsis" *New England Journal of Medicine.* 2001; 344(10):699-709. The PROWESS trial, published in 2001 spurred great excitement due to its absolute reduction in 28-day mortality by 6.1% in septic patients treated with rhaPC and it was subsequently approved for use in the most severely ill septic patients with APACHE scores greater than 25 as this subgroup seemed to derive the most benefit from treatment. Unfortunately, these results were not replicated in the PROWESS-SHOCK study and the treatment was voluntarily removed from the market by the manufacturer Ranieri et al., "Drotrecogin alfa (activated) in adults with septic shock" *New England Journal of Medicine.* 2012; 366(22):2055-2064. The use of rhaPC is not recommended for use in children based on a study published in 2007 that evaluated 477 septic children and failed to show an improvement in mortality. Nadel et al., "Drotrecogin alfa (activated) in children with severe sepsis: a multicentre phase III randomised controlled trial" *The Lancet.* 2007; 369(9564):836-843

Thrombomodulin (TM), another naturally occurring pathway in the coagulation system, is currently being targeted in the treatment of sepsis. TM, produced by endothelial cells, acts upstream in the activated protein C pathway to sensitize the thrombin receptor leading to activation of protein C. Yamakawa et al. "Treatment effects of recombinant human soluble thrombomodulin in patients with severe sepsis: a historical control study" *Critical Care.* 2011; 15(3):p. R123. It has been shown that the serum concentration of TM parallels the severity of coagulopathy and organ failure in sepsis and decreases as DIC and ARDS improves. Lin et al., "Serum thrombomodulin level relates to the clinical course of disseminated intravascular coagulation, multiorgan dysfunction syndrome, and mortality in patients with sepsis" *Critical Care Medicine.* 2008; 36(3):683-689. A control study of 20 patients with severe sepsis-induced DIC treated with rhTM compared to 45 historical controls showed improved 28-day mortality and improved organ dysfunction in those treated with rhTM. Ongoing phase II studies are in progress to evaluate the efficacy of rhTM.

G. Immunostimulator Therapy

Due to the recognition that sepsis is characterized by a combination of hyperimmune response and relative immunoparalysis, further investigations have pursued immunostimulatory strategies. A controversial and widely studied therapy is treatment with the use of pooled serum polyclonal immunoglobulin preparations, IVIG. Although the exact mechanism remains in question, it is thought that the immunoglobulins coat bacteria, which improves phagocytosis and enhances neutralization and opsonization causing inactivation of bacterial endotoxins and exotoxins. Furthermore, it is hypothesized that the treatment alters the release of cytokines and cytokine antagonists by endotoxin and interacts with the complement cascade causing an improved immune response in sepsis. Further supporting this strategy is a recent study which evaluated 62 adult septic patients and revealed decreased levels of immunoglobulins particularly IgG and IgM early in sepsis as compared to age-matched controls. This was followed by normalization of levels after 7 days in the majority of patients. Decreased level of immunoglobulins was associated with decreased levels of plasma proteins but was not associated with a difference in mortality. Venet et al., "Assessment of plasmatic immunoglobulin G, A and M levels in septic shock patients" *International Immunopharmacology.* 2011; 11(12):2086-2090. In 2007 and 2008, three meta-analyses were published that evaluated the efficacy of polyclonal IVIG in adult patients with sepsis. All three concluded that this therapy improved survival but, due to small study sizes, heterogeneity, and methodologic limitations of the individual studies, the three authors recommended large randomized, controlled trials to verify therapeutic efficacy. Kreymann et al., "Use of polyclonal immunoglobulins as adjunctive therapy for sepsis or septic shock" *Critical Care Medicine.* 2007; 35(12):2677-2685: Laupland et al., "Polyclonal intravenous immunoglobulin for the treatment of severe sepsis and septic shock in critically ill adults: a systematic review and meta-analysis" *Critical Care Medicine.* 2007; 35(12):2686-2692; and Turgeon et al., "Meta-analysis: intravenous immunoglobulin in critically ill adult patients with sepsis" *Annals of Internal Medicine.* 2007; 146(3):193-203.

A subsequent Cochrane review published in 2010 evaluated 17 trials of polyclonal IVIG in adult patients with sepsis. This review was in agreement with the prior meta-analyses and showed a reduction in less than 30-day mortality in treated patients. However, the authors recommended cautious interpretation of their findings as the majority of studies had a small sample size and there was concern for poor methodologic quality. Furthermore, when the trials were restricted to those with low risk of bias, no reduction in mortality was shown and the studies that evaluated long-term mortality (greater than 60 days) did not show an effect. The Cochrane review went on to specify their agreement with the Kreymann et al. meta-analysis findings that the IgM-enriched formulation of immunoglobulin is also beneficial and even trended toward a greater effectiveness in the treatment of sepsis. It was concluded that polyclonal immunoglobulins appear to be beneficial as adjuvant therapy for sepsis.

The pediatric population stands to reap greater benefit from IVIG due to the immaturity of B-cells in patients less than 5 years old. In 2005, a prospective case-controlled trial of 100 pediatric patients showed a significant improvement in length of stay, development of complications, and mortality in septic pediatric patients 1 month-24 months old treated with IVIG. El-Nawawy et al., "Intravenous polyclonal immunoglobulin administration to sepsis syndrome patients: a prospective study in a pediatric intensive care unit" *Journal of Tropical Pediatrics.* 2005; 51(5):271-278. Based on the findings of this study, the Surviving Sepsis Guidelines recommend consideration of IVIG treatment of pediatric patients with severe sepsis. However, this recommendation is supported only by weak evidence due to low trial quality. IVIG in the neonatal population is equally as controversial as the Cochrane review found no reduction in mortality in septic neonates treated with IVIG while the Surviving Sepsis Guidelines cite that there is evidence to support improved mortality in neonates treated with IVIG. A study published by Brocklehurst et al. in 2011, after the publication of the Surviving Sepsis Guidelines and Alejandria's Cochrane review, evaluated over 3,000 neonates with sepsis and found no difference in the primary outcomes of mortality or major disability up to two years of age. Brocklehurst et al., "Treatment of neonatal sepsis with intravenous immune globulin" *New England Journal of Medicine.* 2011; 365(13):1201-1211.

Other immunostimulatory strategies include cytokine stimulation with granulocyte-colony stimulating factor (G-CSF), granulocyte-macrophage colony stimulating factor (GM-CSF), and IFN-gamma. The hypothesized mechanism of these therapies in nonneutropenic patients is stimulation of bactericidal activity via increased leukocytosis and increased activity of granulocytes. Bo et al. published a meta-analysis of 21 randomized-controlled trials evaluating G-CSF and GM-CSF in the treatment of sepsis. This evaluation of a combined 2,380 septic patients showed no change in mortality but did show a positive effect of this therapy on the rate of reversal of infection. They found no difference in adverse events between the groups and recommended further studies to evaluate the efficacy of this therapy. Bo et al., "Granulocyte-colony stimulating factor (G-CSF) and granulocyte-macrophage colony stimulating factor (GM-CSF) for sepsis: a meta-analysis" *Critical Care.* 2011; 15(1):p. R58.

G-CSF and GM-CSF may differ in that GM-CSF has additional monocytic and macrocytic stimulatory affects, inducing monocytic cytokine expression and antigen presentation via increased expression mHLA-DR theoretically resulting in improved adaptive immunity. In the meta-analysis by Bo et al., the data evaluating these two therapies were combined despite their differing mechanisms of action. Furthermore, the studies differed significantly on dose as well as on the route of administration and failed to stratify the patients based on their immunologic state. Given the immune-stimulatory mechanism of this therapy, it would be important to know if the patients being studied are in the hyper or hypoimmune phase of sepsis as this may affect the drug's efficacy. Furthermore, new data has shown that it is possible to track the efficacy of immunostimulatory therapies by measurement of mHLA-DR expression on monocytes which is decreased in patients with sepsis-associated immune cell dysfunction. Meisel et al. recently showed that patients with sepsis-associated immunosuppression, defined as low monocytic HLA-DR expression, who were treated with GM-CSF had improvement of monocytic HLA-DR expression when compared to placebo patients. Although this trial included only 38 patients, they were able to show shorter duration of mechanical ventilation as well as shorter ICU and hospital lengths of stay. Schefold J C., "Immunostimulation using granulocyte- and granulocyte-macrophage colony stimulating factor in patients with severe sepsis and septic shock" *Critical Care.* 2011; 15(2):p. 136; Meisel et al., "Granulocyte-macrophage colony-stimulating factor to reverse sepsis-associated immunosuppression: a double-blind, randomized, placebo-controlled multicenter trial" *American Journal of Respiratory and Critical Care Medicine.* 2009; 180(7):640-648.

IFN-gamma has shown similar ability to restore monocytic HLA-DR expression in septic patients with evidence of monocyte deactivation. A small study done by Docke et al. showed that IFN-gamma treatment in septic patients with low monocytic HLA-DR expression resulted in restoration of monocyte function as measured by improved TNF-α secretion resulting in clearance of sepsis in 8 of 9 patients. Docke et al., "Monocyte deactivation in septic patients: restoration by IFN-gamma treatment" *Nature Medicine.* 1997; 3(6):678-681.

The results of these studies are encouraging that immunostimulation may be an effective way to treat the subset of septic patients who are in the immunoparalysis phase of their disease.

V. Sepsis Proteomic Expression Profiles: Age-Related Treatment

In one embodiment, the present invention contemplates a method for developing efficient therapeutic strategies for patients with sepsis to slow inflammatory response and reduce mortality rates. As detailed above, antimicrobial treatments and early goal-directed therapy are used in the management of sepsis. Carvalho et al., *Journal of Pediatrics* 79:S195 (2003); and Hotchkiss et al., *New England Journal of Medicine* 348:138 (2003). However, these strategies in clinical practice are limited. For example, the choice of a specific antimicrobial treatment can be influenced by the infection site and molecules released from microorganisms may exacerbate inflammatory response. Other therapies, including but not limited to, glucocorticoids, recombinant human-activated protein C, steroids, intravenous Ig, continuous renal replacement therapy, proinflammatory cytokine inhibitors, antioxidant supplementation have failed to provide an effective treatment for sepsis. Overall, more than forty (40) clinical trials of therapies targeted at septic patients have failed to lead to a current FDA-approved drug for the universal treatment of sepsis. Annane et al., *British Medical Journal* 329: 480 (2004); Casserly et al., *Critical Care Medicine* 40:1417 (2012); Patel et al., *American Journal of Respiratory and Critical Care Medicine* 185:133 (2012); Turgeon et al., *Annals of Internal Medicine* 146:193 (2007); Joannidis, M., *Seminars in Dialysis* 22:160 (2009); Berger et al., *Critical Care Medicine* 35:S584 (2007): Ward et al., *Critical Care Research and Practice* 2012:8 (2012); Hotchkiss et al., *The Lancet Infectious Diseases* 13:260 (2013); Wu et al., *Shock* 21:210 (2004).

The lack of current universal treatment for sepsis can be understood due to the many challenges associated with this condition. Diagnosis of sepsis is complicated by its differential presentation between patients (i.e., degree and nature of clinical symptoms can vary tremendously). In addition to patient heterogeneity, there is also temporal heterogeneity within individual patients. An et al., *Critical Reviews in Biomedical Engineering* 40:341 (2012). The timing of the diagnosis plays a role regarding the initiation of therapy, however, this is difficult because cell culture determination assays can take as long as 48 h and some patients have symptoms for a day prior to hospital admission. Rivers et al., *Shock* 39:127 (2013). Furthermore, in more than half of sepsis cases, clinical symptoms may persist without a positive culture. Carrigan et al., *Clinical Chemistry* 50:1301 (2004).

Monitoring of specific biomarkers (e.g., tumor necrosis factor (TNF)-α, interleukin (IL)-1, IL-6, IL-8, and IL-10, procalcitonin, C-reactive protein, and others) have yielded conflicting results with regards to sensitivity, specificity, and effectiveness in both adults and neonates. Rivers et al., *Shock* 39:127 (2013). Furthermore, in more than half of sepsis cases, clinical symptoms may persist without a positive culture. Carrigan et al., *Clinical Chemistry* 50:1301 (2004). Because many of these molecules also play a role in immune response and inflammation, a single readout of any specific biomarker can be misleading. Biomarker readouts are heavily time-dependent as at least one acute proinflammatory response occurs within the first 24 h after infection. Rivers et al., *Shock* 39:127 (2013). Although it is not necessary to understand the mechanism of an invention, it is believed that these challenges to developing new therapeutics and treatment strategies regarding sepsis diagnosis, prognosis, and real-time response to treatment of sepsis can be best facilitated by understanding the molecular mechanisms of this condition.

Although it is not necessary to understand the mechanism of an invention, it is believed that the sepsis proteomic expression profiled disclosed herein imply that age is an important factor affecting a patient response to sepsis. For example, hyper- and hypo-inflammatory response is found in the younger and older severe sepsis patients, respectively. These findings suggest that doctors need to be cautious when interpreting clinical data from sepsis patients at different ages. For example, high plasma concentrations of CRP may lead to the development of severe sepsis in younger CAP patients but low CRP concentrations may indicate poor outcome in older CAP patients. These observations also suggest that different treatments need to be performed based on the ages of sepsis patients.

This differential strategy to treat sepsis may be related to a phenomenon termed immunosensence. Immunosenescence usually refers to a gradual deterioration of the immune system during aging. It is widely accepted that immunosenescence is characterized by diminished immune response, low-grade inflammation, and increased propensity for autoimmunity. These changes in the immune system increase the risk and mortality of diseases among the elderly. Poor response to immunotherapies as a result of immunosenescence can further worsen this situation. In particular, vaccination is an important intervention for disease control and has been used effectively in children and younger adults. Goronzy et al., *Nature Immunology* 14:428 (2013). A fundamental understanding of immunosenescence would be helpful for the prevention and treatment of aging-related diseases. For example, genomics, transcriptomics, proteomics, and metabolomics can give insight to molecular mechanisms of immunosenescence and its contribution to developing proper and effective treatments for age-related diseases (e.g., for example, severe sepsis).

The data presented herein show that there are specific protein pathways that are differentially expressed between younger and older patients with sepsis. Consequently, this may explain the above described failure of those in the art to identify conclusive sepsis biomarkers. For example, tests of sepsis or to predict sepsis severity have been limited. In one report, an AUC of about 0.73 for prediction of mortality using a 6-marker panel. Wong et al., "A Multibiomarker-Based Outcome Risk Stratification Model for Adult Septic Shock" *Critical Care Medicine* 42(4):781-789 (2014). Procalcitonin is approved for risk assessment in sepsis but its performance isn't much better. Although it is not necessary to understand the mechanism of an invention, it is believed that sepsis may have different biomarker patterns between older as compared to younger adults leading to different biomarker patterns.

In one embodiment, the present invention contemplates that the differentially expressed protein pathways between older and younger sepsis patients represent age-specific drug targets. Although it is not necessary to understand the mechanism of an invention, it is believed that giving young and old the same therapies could harm one or the other.

In one embodiment, the present invention contemplates specific drug targets for the treatment of an older sepsis patient. In one embodiment, the drug target comprises a hepatic stellate cell activation pathway. In one embodiment the drug target comprises an actin cytoskeleton signaling pathway. In one embodiment, the method further comprises a combination treatment of the specific drug target with a conventional sepsis treatment. In one embodiment, the conventional treatment includes, but is not limited to, antibiotics, inflammatory mediator inhibitors, steroids, proinflammatory cytokine inhibitors, statins, coagulation cascade inhibitors and/or immunostimulators.

In one embodiment, the present invention contemplates specific drug targets for the treatment of a younger sepsis patient. In one embodiment, the drug target comprises a blood factor coagulation pathway. In one embodiment, the drug target comprises an extrinsic prothrombin activation pathway. In one embodiment, the drug target comprises an intrinsic prothrombin activation pathway. In one embodiment, the method further comprises a combination treatment of the specific drug target with a conventional sepsis treatment. In one embodiment, the conventional treatment includes, but is not limited to, antibiotics, inflammatory mediator inhibitors, steroids, proinflammatory cytokine inhibitors, statins, coagulation cascade inhibitors and/or immunostimulators.

VI. Pharmaceutical Compositions/Formulations

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 µg to 100 g per kg of body weight, once or more daily, to once every 20 years.

EXPERIMENTAL

Example I

Expression Profile Patent Population

The data presented herein was collected during a nested case-control study using patients enrolled in the GenIMS study. Kellum et al., "Understanding the Inflammatory Cytokine Response in Pneumonia and Sepsis: Results of the Genetic and Inflammatory Markers of Sepsis (GenIMS) Study" *Arch Intern Med* 167:1655-1663 ((2007).

A total of 39 patients comprised the four experimental groups:
1) patients 50-65 years old who did not develop severe sepsis (YC);
2) patients 70-85 years old who did not develop severe sepsis (OC);
3) patients 50-65 years old who developed severe sepsis (YS), and
4) patients 70-85 years old who developed severe sepsis (OS).
To ensure that differences in immune response are attributed to age and not to ethnic differences or underlying chronic diseases, only whites and matched patients according to chronic disease burden were included. Approval for the participation of human patients was obtained by the Institutional Review Board of the University of Pittsburgh and other participating sites.

Example II

Blood Sample Collection and Processing

Plasma samples were obtained from patients at initial presentation and prior to most interventions to ensure that differences in immune response are not affected by therapeutic strategies. Crude human plasma was prepared and analyzed as described in FIG. 1A-D.

Multiple Affinity Removal System (MARS) columns were used to deplete high-abundance proteins. Unbound proteins on the MARS column were subject to trypsin digestion and modified with an iTRAQ reagent. The Hu 6 MARS column (Agilent; Santa Clara, Calif.) depletes serum albumin, IgG, α1-antitrypsin, IgA, transferrin, and haptoglobin proteins. An injection amount of 60 µL of crude plasma was applied to the MARS column and after the initial depletion flow-through fractions were concentrated with a 5K molecular weight cutoff concentrator (Agilent) at 4695 g for 1.5 hours.

Modified peptides were combined, fractionated with Strong Cation Exchange (SCX), and thirteen fractions were collected and analyzed by LC-MS/MS on a linear ion trap-Orbitrap Velos MS. Collision induced dissociation (CID) and high energy C-trap dissociation (HCD) were used for gas-phase fragmentation of peptides. Proteome Discoverer 1.2 was used to process data files, perform SEQUEST searches, and extract iTRAQ information. Plasma from CAP patients was used to optimize the workflow.

Samples were then stored at −80° C. or re-injected onto the MARS column for tandem MARS depletion. The second flow-through fractions (hereafter referred to as TMD) were concentrated and protein concentrations were measured using the BCA protein assay.

TABLE 8

Protein amounts recovered from crude plasma in the unbound fractions from $MD^1$ and $TMD^2$

| Sample | Protein mass, µg | % depletion | EF[#], -fold* |
|---|---|---|---|
| Crude | 4416 | / | / |
| MD | 527 ± 52 | 88.1 | 8.4 |
| TMD | 343 ± 54 | 92.2 | 12.8 |

[#]enrichment factor,
*relative to crude plasma,
[1]MARS-Depletion,
[2]Tandem MARS-Depletion Example III Protein Digestion Protein was denatured with an extraction buffer (0.2 M Tris, 8 M urea, 10 mM CaCl2, pH 8.0), reduced with 1:40 molar excess of dithiothreitol (DTT) for 2 h at 37□C, and then alkylated with 1:80 molar excess of iodoacetamide (IAM) for 2 h on ice. The alkylation reaction was quenched by adding 1:40 molar excess of Cysteine and the mixture was incubated at room temperature for 30 min. Tris buffer (0.2 M Tris, 10 mM CaCl2, pH 8.0) was added to dilute the urea concentration to 2 M. Each sample was incubated with bovine TPCK-heated trypsin at 1:50 substrate:enzyme ratio for 24 h at 37° C.

Example IV iTRAQ Labeling

Digested samples were desalted with an HLB cartridge (Waters; Milford, Mass.) and dried by centrifugal evaporation. Each sample was labeled with an iTRAQ reagent following the manufacturer's protocol (Applied Biosystems; Foster City, Calif.) with slight modifications. Briefly, each iTRAQ reagent was solubilized with 70 µL ethanol and transferred to peptide mixtures. After 1.5 h of incubation, the reaction was quenched with water. Labeled samples were mixed in 1:1:1:1 ratios for iTRAQ reagents that generate reporter ions at m/z 114:115:116:117, respectively.

Example V

SCX Fractionation

SCX fractionation was carried out on a PolySulfoethyl A 100 mm×2.1 mm, 5 µm, 200 Å column (The Nest Group, Inc.; Southborough, Mass.) with buffers as follows: mobile phase A was 5 mM monopotassium phosphate (25% v/v acetonitrile, pH 3.0), and mobile phase B was 5 mM phosphate, 350 mM potassium chloride, (25% v/v acetonitrile, pH 3.0). Dried iTRAQ labeled samples were resuspended in 300 µL of mobile phase A and injected onto the SCX column. The gradient for SCX was: 0-3 min, 0% B; 3-45 min, 0-75% B; 45-50 min, 75-100% B; 50-55 min, 100% mobile phase B; 55-56 min, 100-0% B; 56-106 min, 0% B. Thirteen SCX fractions were collected and each fraction was desalted with an HLB cartridge (Waters).

Example VI

LC-MS/MS Analysis

Online desalting and reversed phase chromatography was performed with a Nano-2D-LC system equipped with an autosampler (Eksigent; Dublin, Calif.). Mobile phase A and B for these analyses were 3% (v/v) acetonitrile with 0.1% formic acid and 100% (v/v) acetonitrile with 0.1% formic acid, respectively. SCX fractions (5 µL) were loaded onto a trapping column (100 µm i.d.×2 cm), which was packed in-house with C18 200 Å 3 µm stationary phase material (Michrom Bioresource Inc.; Auburn, Calif.) at 3 µL-min$^{-1}$ in 3% mobile phase B for 3 min. After desalting, the sample was loaded onto an analytical column (75 µm i.d.×13.2 cm), which was packed in-house with C18 100 Å 3 µm stationary phase material (Michrom Bioresource Inc.). The gradient was as follows: 0-5 min, 10% mobile phase B; 5-75 min, 10-30% B; 75-95 min, 30-60% B; 95-100 min, 60-90% B; 100-105 min, 90-10% B; 110-120 min, 10% B. The LC eluent was analyzed with positive ion nanoflow electrospray using a LTQ-Orbitrap Velos mass spectrometer (Thermo-Fisher Scientific, Waltham, Mass.). Data-dependent acquisition parameters were as follows: the MS survey scan in the Orbitrap was 60,000 resolution over 300-1800 m/z; the top six most intense peaks in the MS survey scan were isolated and fragmented with CID and HCD; CID was performed in the ion trap with normalized collision energy 35%; HCD was recorded in the Orbitrap with normalized collision energy 45% and 7,500 resolution; dynamic exclusion was enabled for 61 seconds and a repeat count of 2 for a duration of 60 seconds was allowed and selected ions were placed on an exclusion list for 61 seconds. Each SCX fraction was subject to triplicate LC-MS/MS analysis.

Example VII

Data Analysis

".RAW" files were analyzed with Proteome Discoverer 1.2 software (Thermo). Both CID and HCD spectra were used to obtain sequence information against the Uniprot human database (Apr. 25, 2010, 20,295 sequences). Sequest search parameters were as follows: two maximum trypsin miscleavages; precursor mass tolerance 10 ppm; fragment mass tolerance 0.8 Da; static modifications were iTRAQ-4plex/+144.102 Da (N-terminus, Lys), and carbamidomethyl modification/+57.021 Da (Cys); dynamic modification of iTRAQ-4plex/+144.102 Da (Tyr). Decoy database searching was employed to generate medium (p<0.05) and high (p<0.01) confidence peptide lists. All the peptides with medium and high confidence were used to identify and quantify proteins. Only proteins with at least two spectral counts in a technical replicate were considered for further analysis.

Example VIII

Statistics

Coefficient of variation (CV) values were calculated for reporter ion ratios (e.g., 115/114, 116/114, and 117/114) of proteins quantified in at least six iTRAQ experiments. The mean CV value across the iTRAQ experiments was calculated and used as the total biological variation, Sb. The technical variation, St, was calculated for proteins quantified in at least two LC-MS/MS analyses within an individual iTRAQ experiment. The relation between the fold change (F), random variation (S), biological variation (Sb), and technical variation St is expressed by the formula:

$$n = 2\frac{(Z+T)^2 S^2}{(F-1)^2} \quad (1)$$

$$S = 2\left(\frac{S_b^2}{n} + \frac{S_t^2}{nm}\right) \quad (2)$$

Horgan, G. W., "Sample size and replication in 2D gel electrophoresis studies" *Journal of Proteome Research* 6:2884-2887 ((2007). The quantities Z and T depend on the power of the test (i.e., 0.8) and the significance level (i.e., 0.05), respectively. n and m, the number of biological and technical replicates, respectively, were set to 10 and 3 for these studies, such that formula (1) and (2) approximates to:

$$10 = 20 \frac{S^2}{(F-1)^2} \quad (3)$$

$$S^2 = \frac{S_b^2}{10} + \frac{S_t^2}{30} \quad (4)$$

Solve formulas (3) and (4), $$F = \left(\frac{3S_b^2 + S_t^2}{15}\right)^{1/2} + 1 \quad (5)$$

Based on this power analysis, the calculated fold-change cutoff that was applied to these data is ~1.30. Filter criteria were applied to generate a list of statistically significant differentially-expressed proteins as follows: 1) proteins identified and quantified in at least six experiments, 2) CV values ≤0.60, and 3) fold-change cutoff ≥1.30 or ≤0.77.

Example IX

Western Blotting Analyses

The changes in the expression of C-reactive protein (CRP), apolipoprotein CIII (Apo CIII), and fibrinogen alpha chain (FAC) were subject to Western blot analysis. Twenty µg of protein was denatured in an appropriate sample buffer and electrophoretically separated on a Criterion precast gel (Biorad Laboratories; Hercules, Calif.) at 140 V. Proteins from the gel were transferred onto a nitrocellulose membrane paper using a Fast-Transfer Blot System (Biorad). Blots were washed three times in Wash blot. BSA blocking solution (3%) was added to the membrane and incubated on a rocker for 2 h. A 1:5000 dilution of mouse monoclonal anti-CRP primary antibody (Sigma Aldrich; St. Louis, Mo.), 1:5000 dilution of rabbit polyclonal anti-Apo CIII primary antibody (Abeam; Cambridge, Mass.), or 1:2500 dilution of rabbit monoclonal anti-FAC primary antibody (Abeam) was added and incubated at 4° C. overnight. The blot was rinsed and incubated with a 1:7500 dilution of anti-mouse or anti-rabbit IgG alkaline phosphatase secondary antibody (Sigma Aldrich) for 1 h on a rocker. The blot was rinsed and colorometrically developed using 0.51 mM 5-bromo-4-chloro-3'-indolyphosphate p-toluidine salt (BCIP) and 0.24 mM nitrotetrazolium blue (NBT). The dried blot was scanned using a Canon scanner, saved as a ".TIFF" file, and densitometry analyses carried out with Scion Image Software. Within each experiment, the intensity for the sample from each group was normalized to the total blot intensity and used to generate mean and standard deviation values.

Example X

Ingenuity Pathway Analysis

Differentially-expressed proteins were analyzed using Ingenuity Pathway Analysis (IPA, www.ingenuity.com) to generate a list of pathways that are statistically relevant (p<0.05).

We claim:

1. A method for treating sepsis development, comprising:
   a) providing;
      i) at least one biological sample derived from an elderly patient suspected of having an intra-abdominal infection;
      ii) at least one peptide isolated from said at least one biological sample, wherein said at least one isolated peptide comprises at least one isobaric tag for relative and absolute quantitation (iTRAQ) reporter ion;
      iii) a system comprising a liquid chromatography column and a mass spectrometer;
      iv) a control proteomic pathway expression profile; and
      v) a sepsis proteomic pathway expression profile;
   b) contacting said at least one iTRAQ-peptide with said system to create at least one iTRAQ-peptide analysis spectrum;
   c) processing said at least one iTRAQ-peptide analysis spectrum to create a patient proteomic pathway expression profile,
   d) comparing said patient proteomic pathway expression profile to said control proteomic pathway expression profile and said sepsis proteomic pathway expression profile wherein at least one protein pathway of said patient proteomic pathway expression profile has an overexpression ratio when compared with said control proteomic pathway expression profile and does not have an overexpression ratio when compared with said sepsis pathway expression profile; and
   e) treating said patient for sepsis development.

2. The method of claim 1, wherein said elderly patient is of an age ranging between seventy (70 and eight-five (85) years.

3. The method of claim 1, wherein said at least one protein pathway is a liver retinoid X receptor activation pathway.

4. The method of claim 3, wherein said liver retinoid X receptor activation pathway is about ten-fold over-expressed as compared to said control proteomic pathway expression profile.

5. The method of claim 1, wherein said at least one protein pathway is an acute phase response signaling pathway.

6. The method of claim 5, wherein said acute phase response signaling pathway is about eight-fold over-expressed as compared to said control proteomic pathway expression profile.

7. The method of claim 1, wherein said at least one protein pathway is an atherosclerosis signaling pathway.

8. The method of claim 7, wherein said atherosclerosis signaling pathway is about evenfold over-expressed as compared to said control proteomic pathway expression profile.

9. The method of claim 1, wherein said at least one protein pathway is an interleukin-2 signaling pathway.

10. The method of claim 9, wherein said interleukin-2 signaling pathway is about seven-fold over-expressed as compared to said control proteomic pathway expression profile.

11. The method of claim 1, wherein said at least one protein pathway is a nitric oxide/oxygen reactive species pathway.

12. The method of claim 11, wherein said nitric oxide/oxygen reactive species pathway is about seven-fold over-expressed as compared to said control proteomic pathway expression profile.

13. The method of claim 1, wherein said at least one protein pathway is a clathrin-mediated endocytosis signaling pathway.

14. The method of claim 13, wherein said clathrin-mediated endocytosis signaling pathway is about seven-fold over-expressed as compared to said control proteomic pathway expression profile.

15. The method of claim 1, wherein said over-expressed protein pathway is an lipopolysaccharide/interleukin-1 retinoid X receptor inhibition pathway.

16. The method of claim 15, wherein said lipopolysacharride-interleukin-1 retinoid X receptor inhibition pathway is about three-fold over-expressed as compared to said control proteomic pathway expression profile.

17. The method of claim 1, wherein said at least one protein pathway is a farnesoid X receptor activation pathway.

18. The method of claim 17, wherein said farnesoid X receptor activation pathway is about two-fold over-expressed as compared to said control proteomic pathway expression profile.

19. The method of claim 1, wherein said at least one protein pathway is a hepatic stellate cell activation pathway.

20. The method of claim 19, wherein said hepatic stellate cell activation pathway is about two-fold over-expressed as compared to said control proteomic pathway expression profile.

21. The method of claim 1, wherein said at least one protein pathway is an actin cytoskeleton signaling pathway.

22. The method of claim 21, wherein said actin cytoskeleton signaling pathway is about twofold over-expressed as compared to said control proteomic pathway expression profile.

23. The method of claim 1, wherein said treating comprises a therapy selected from the group consisting of fluid therapy, vasopressor therapy, inotropic support, antibiotics, albumin and red blood cell transfusion.

24. The method of claim 1, wherein said treating comprises a broad spectrum antibiotic selected from the group consisting of ampicillin, amoxicillin, carbapenems, imipenem, meropenem, ertapenem, piperacillin, tazobactam, levofloxacin, gatifloxacin, moxifloxacin, ciprofloxacin, streptomycin, tetracycline, chloramphenicol and ticarcillin.

25. The method of claim 1, wherein said treating comprises a therapy selected from the group consisting of a steroid therapy, a statin therapy, an anticoagulant therapy, a thrombomodulin therapy and an immunostimulator therapy.

* * * * *